US007705203B2

(12) United States Patent
Hodges et al.

(10) Patent No.: US 7,705,203 B2
(45) Date of Patent: Apr. 27, 2010

(54) BENZOATE INDUCIBLE PROMOTERS

(75) Inventors: Thomas K. Hodges, Claiborne, MD (US); Mauricio S. Antunes, West Lafayette, IN (US); Nicholas Carpita, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 160 days.

(21) Appl. No.: 10/534,405

(22) PCT Filed: Nov. 12, 2003

(86) PCT No.: PCT/US03/35810

§ 371 (c)(1),
(2), (4) Date: Dec. 27, 2005

(87) PCT Pub. No.: WO2004/043885

PCT Pub. Date: May 27, 2004

(65) Prior Publication Data

US 2006/0277620 A1    Dec. 7, 2006

Related U.S. Application Data

(60) Provisional application No. 60/426,060, filed on Nov. 13, 2002, provisional application No. 60/425,760, filed on Nov. 12, 2002.

(51) Int. Cl.
*C12N 15/82* (2006.01)
(52) U.S. Cl. .................... 800/298; 800/278; 435/320.1; 435/419
(58) Field of Classification Search ........................ None
See application file for complete search history.

(56) References Cited

U.S. PATENT DOCUMENTS

| 5,034,323 A | 7/1991 | Jorgensen et al. |
| 5,107,065 A | 4/1992 | Shewmaker et al. |
| 5,283,184 A | 2/1994 | Jorgensen et al. |
| 5,352,605 A | 10/1994 | Fraley et al. |
| 6,765,129 B1 * | 7/2004 | Lichtenthaler et al. ...... 800/282 |
| 6,803,224 B2 * | 10/2004 | Ramirez et al. ........ 435/252.33 |

FOREIGN PATENT DOCUMENTS

| WO | WO 93/07277 | * | 4/1993 |
| WO | WO 95/14098 | | 5/1995 |
| WO | WO 95 19443 | * | 7/1995 |
| WO | WO 98 03536 | * | 1/1998 |
| WO | WO 2004/043885 A3 | | 5/2004 |

OTHER PUBLICATIONS

Bell, et al, (1991) J. Bacteriology 173:6657-6664.*
Federspiel N.A. et al: Database EMBL, Feb. 7, 2000, '*Arabidopsis thaliana* chromosome I BAG T14P4 genomic sequence, complete sequence.' Database accession No. AC022521.*
Hauschild, et al (1998) Isolation and analysis of the gene bbe1 encoding the berberine bridge enzyme from the California poppy *Eschscholzia californica* Plant Molec. Biol. 36:473-478.*
Hannenhalli et al., (2001) Promoter prediction in the human genome. Bioinformatics 17: S90-S96.*
Kim et al., (1994) A 20 nucleotide upstream element is essential for the nopaline synthase (nos) promoter activity. Plant Molecular Biology 24: 105-117.*
van Gorcom et al (1990, Mol. Gen. Genet. 223:192-197).*
Antunes, Mauricio S., Characterizing a benzoic acid inducible promoter system from the fungus *Aspergillus niger*, (2003), Dissertation from Purdue Univ., West Lafayette, IN, USA.*
Benfrey et al, 1990, Science 250:959-966.*
Kessler et al., A general system to integrate lacZ fusions into the chromosomes of gram-negative eubacteria: regulation of the Pm promoter of the TOL plasmid studied with all controlling elements in monocopy, Mol Gen Genet (1991) 233:292-301.
van den Brink et al., "Regulation of expression of the *Aspergillus niger* benzoate para-hydroxylase cytochrome P450 system," (2000) Mol. Gen. Genet. 263: 601-609.
Garbarino and Belknap, "Isolation of a ubiquitin-ribosomal protein gene (ubi3) from potato and expression of its promoter in transgenic plants," Plant Mol. Biol. 24:119-127 (1994).
Lee et al., "A retinoic acid response element that overlaps an estrogen response element mediates multihormonal sensitivity in transcriptional activation of the lactoferrin gene," (1995) Mol. Cell. Biol. 15: 4194-4207.
Zelhof et al., "Identification and characterization of a Drosophila nuclear receptor with the ability to inhibit the ecdysone response," (1995) Proc. Natl. Acad. Sci. USA 92: 10477-10481.
Yin et al., "Promoter elements required for phloem-specific gene expression from the RTBV promoter in rice," (1997) Plant J. 12: 1179-1188.
González-Pérez et al., "Critical Nucleotides in the Upstream Region of the XylS-dependent TOL meta-Cleavage Pathway Operon Promoter as Deduced from Analysis of Mutants," (1999) J. Biol. Chem. 274: 2286-2290.
Park et al., "Molecular cloning and biological activity of ecdysis-triggering hormones in Drosophila melanogaster," (1999) FEBS Letters 463: 133-138.
Yu et at., " Sequence-specific DNA Recognition by the Myb-like Domain of Plant Telomeric Protein RTBP1," (2000) J. Biol. Chem. 275: 24208-24214.
Risoen et al., "Regulation of bacteriocin production in *Lactobacillus plantarum* depends on a conserved promoter arrangement with consensus binding sequence," (2001) Mol. Gen. Genom. 265: 198-206.
Gossen and Bujard, "Tight control of gene expression in mammalian cells by tetracycline-responsive promoters," (1992) Proc. Natl. Acad. Sci. USA 89: 5547-5551.
Shockett and Schatz, "Diverse strategies for tetracycline-regulated inducible gene expression," (1996) Proc. Natl. Acad. Sci. USA 93, 5173-5176.
Aoyama and Chua, "A glucocorticoid-mediated transcriptional induction system in transgenic plants," (1997) Plant J. 11: 605-612.

(Continued)

*Primary Examiner*—Anne R Kubelik
(74) *Attorney, Agent, or Firm*—Brinks Hofer Gilson & Lione

(57) ABSTRACT

Benzoate inducible promoters and promoter systems are disclosed, and uses thereof. Polynucleotides disclosing Benzoate Response Elements are also disclosed.

16 Claims, 21 Drawing Sheets

OTHER PUBLICATIONS

Kunkel et al., "Inducible isopentenyl transferase as a high-efficiency marker for plant transformation," (1999) Nature Biotech. 17: 916-919.

Mett et al., "Copper-controllable gene expression system for whole plants," (1993) Proc. Natl. Acad. Sci. USA 90: 4567-4571.

Caddick et al., "An ethanol inducible gene switch for plants used to manipulate carbon metabolism," (1998) Nature Biotech. 16: 177-180.

Salter et al., "Characterisation of the ethanol-inducible alc gene expression system for transgenic plants," (1998) Plant J. 16: 127-132.

De Veylder et al., "Herbicide safener-inducible gene expression in *Arabidopsis thaliana*," (1997) Plant Cell Physiol. 38: 568-57.

Jepson et al., "Chemical-Inducible Gene Expression Systems for Plants-a Review," (1998) Pestic. Sci. 54: 360-367.

Kang et al., "A glucocorticoid-inducible transcription system causes severe growth defects in *Arabidopsis* and induces defense-related genes, " (1999) Plant J. 20: 127-133.

Sahasrabudhe and Modi, "Hydroxylation of benzoate and its chlorinated derivatives in *Aspergillus niger*," (1985) Biochem. Intl. 10: 525-529.

Schultz and Haughn, "LEAFY, a Homeotic Gene That Regulates Inflorescence Development in *Arabidopsis*," (1991) Plant Cell 3, 771-781.

Weigel et al., "LEAFY controls floral meristem identity in *Arabidopsis*," (1992) Cell 69, 843-859.

Kardailsky et al., "Activation tagging of the floral inducer FT," (1999) Science 286: 1962-1965.

Bell, "Pseudomonas aeruginosa outer membrane protein OprH: expression from the cloned gene and function in EDTA and gentamicin resistance," J Bacteriol. Nov. 1991;173(21):6657-64.

Herrero et al., "A T7 RNA polymerase-based system for the construction of Pseudomonas strains with phenotypes dependent on TOL-meta pathway effectors," 134:103 (1993).

Cuskey, "Benzoate-dependent induction from the OP2 operator-promoter region of the TOL plasmid pWWO in the absence of known plasmid regulatory genes," J Bacteriol. Aug. 1988;170(8):3742-6.

* cited by examiner

Fig. 1

A. SEQ ID NO:1

```
-1847      CGTGTCC  GTTCTACAAG  ATCATCCCTG  GATTCTCCCT  CTGTGTGGAT
-1800    GCATTTCGAT  ACGGAGCCGT  AGAGGGATGT  AATGCGTACT  TCCTTAGTCA
-1750    CTTCCACAGC  GACCATTACA  TCGGCCTGAC  GGGGTCGTGG  CGCCATGGAC
-1700    CAATCTACTG  CAGCAGACCT  ACGGCCAACT  TGGTGTGCCA  GCAACTGAAG
-1650    GTCGACCGGA  AGTGGCTTGT  ACCACTTGAG  TTCGAGCGGA  AGACGGAAAT
-1600    CCCGGATACA  GGAGGAGCGC  AGGTGACTTT  GATCGAGGCT  AATCATTGTC
-1550    CTGGGAGCGC  CATCTTTCTC  TTCGAGAAAT  CAATGGGATC  GGGTCCCTCG
-1500    CAGAGAACAC  ATCGTGTCCT  CCACTGTGGT  GACTTTCGCG  CCTCGCCGCT
-1450    TCATGTGCAA  CATGCCCTTC  TCCGCCCGGA  GATTGCTGAC  CCCGCAACCG
-1400    GCAAGGCTCG  CCAGCAACGA  ATCGATGCCT  GCTATCTGGA  CACTACATAT
-1350    TTGAGCCCCA  AGTATGCATT  CCCTGGCCAG  GAAGATGTCA  TACAAGCCTG
-1300    CGCAGAACTT  TGCGTTGAGC  TCGATGGGGA  CGCCAACGAC  ACAAATGGAC
-1250    GAGCATTTGG  ACGACCAGTC  AATGGAAAAA  GCGGAATGCT  GAGCAAGTTT
-1200    GTTACGGCTG  TGACTGGATC  CCGCCCGTCT  CCGACGCAAG  ACAGCCGCCC
-1150    CCCTGGCCGG  CTATTGGTAG  TAATAGGGAC  GTACAGCATC  GGCAAAGAAC
-1100    GCATCTGTCT  GGGGATCGCA  CGGGCATTGA  AGAGCAAGAT  CTACGCGACG
-1050    CCAGCTAAGC  AGCGCGTCTG  TGCGTGCCTC  GAGGATGCTG  AGCTGTCATC
-1000    GCTGCTGACA  GACGATCCCA  CGGAGGCGCA  GGTGCATATG  CAAACGCTAT
 -950    TCGAGATCCG  GGCGGAAACG  CTGGCGGATT  ACCTGGACTC  GATGAAGCCG
 -900    CACTTCACGC  GGGTGGTGGG  ATTTCGACCA  ACCGGGTGGA  CGTATCGCCC
 -850    GCCAGCTGGC  CGAATGCTGG  ACAACCCACC  GGTGTCGGTG  GTGCTCAATT
 -800    CGGCACATTG  GAAGACGCCC  TTTTCTGCGA  AAGACCTGGT  GCCACAGCGA
 -750    GGGAGTACGC  GGGAAAGCGC  ATGCTTTGGA  GTGCCGTACA  GTGAGCACAG
 -700    CTCATTTCGG  GAGTTGAGCA  TGTTCTGCTG  CGCACTCCGG  ATCGGACGGG
 -650    TGATCCCGAC  AGTGAACGTA  GGTAGCCGGA  AAAGTCGGGA  GCGCATGAAG
 -600    GCGTGGATTG  AGCGATGGGA  GGCGGAGAAG  CGGAAGAATG  GGTTCTACCG
 -550    CGTGGAGGGG  AATAGCTGGT  AGGGAAGGGA  ATAGATGGCT  CTACCAATGT
 -500    CCAAAGTACT  GGTGGAACAG  AAGGATCAGA  AGGATTGCGA  AAGACGGGTC
 -450    GGAACATGAT  GCCTAATAGA  GTAAGTAAGG  AGTTGGTGCT  GTAACTAGTC
 -400    ACAAGTTACG  AGTTGTGTAC  ATAACATCAT  TAGTCATGAA  GATCAATTGC
 -350    CTTTATGCTT  CCGTAACTCT  CGCCTCCCCG  GAGTCACGAG  ATCAATAGAA
 -300    ACCACCGCCG  TTGACCATTC  GCGATGCTCT  CACTGGCTGT  ATGCTGTCGA
 -250    TAGCCATGGA  GCCATTCAAA  GTATGGACCC  TTTGGGTGAG  GATCTCCCTC
 -200    CAACCCCACG  GGACGTACAC  GAACAACCGA  GCAGAGGCGG  GGGAGGGCAA
 -150    AGAGGCCGGC  GCTGCAAATC  GGCTGGCAGA  TCAGTCGCGG  CTCAGCAGAG
 -100    ACTCCGATT   TTCCCTTCCG  TTGCCTGGCT  TTGCCTCGGG  GTTCGAGAGG
  -50    AGCCCGTCTG  CCATAAATAA  GCCTGCACTT  CAACTCAAAA  AAAAGGGAGA
```

Fig. 1 (cont.)

B. A 0.4 kbp sequence comprising positions −119 to −521 of SEQ ID NO:1 (SEQ ID NO:2)
```
                             A ATAGATGGCT CTACCAATGT
-500 CCAAAGTACT GGTGGAACAG AAGGATCAGA AGGATTGCGA AAGACGGGTC
-450 GGAACATGAT GCCTAATAGA GTAAGTAAGG AGTTGGTGCT GTAACTAGTC
-400 ACAAGTTACG AGTTGTGTAC ATAACATCAT TAGTCATGAA GATCAATTGC
-350 CTTTATGCTT CCGTAACTCT CGCCTCCCCG GAGTCACGAG ATCAATAGAA
-300 ACCACCGCCG TTGACCATTC GCGATGCTCT CACTGGCTGT ATGCTGTCGA
-250 TAGCCATGGA GCCATTCAAA GTATGGACCC TTTGGGTGAG GATCTCCCTC
-200 CAACCCCACG GGACGTACAC GAACAACCGA GCAGAGGCGG GGGAGGGCAA
-150 AGAGGCCGGC GCTGCAAATC GGCTGGCAGA TC
```

C. a 200 bp fragment (SEQ ID NO:3), comprising positions −331 to −531 of SEQ ID NO:1
```
                           T AGGGAAGGGA ATAGATGGCT CTACCAATGT
-500 CCAAAGTACT GGTGGAACAG AAGGATCAGA AGGATTGCGA AAGACGGGTC
-450 GGAACATGAT GCCTAATAGA GTAAGTAAGG AGTTGGTGCT GTAACTAGTC
-400 ACAAGTTACG AGTTGTGTAC ATAACATCAT TAGTCATGAA GATCAATTGC
-350 CTTTATGCTT CCGTAACTCT
```

D. BREF51 (SEQ ID NO:4), a 51 bp sequence comprising positions −357 to −407 of SEQ ID NO:1
```
                                                     ACTAGTC
-400 ACAAGTTACG AGTTGTGTAC ATAACATCAT TAGTCATGAA GATC
```

E. BRE6 (SEQ ID NO:5), a 6 bp sequence TAGTCA, positioned −365 to −370 within SEQ ID NO:1

F. SEQ ID NO:6, a 531 bp sequence from −1 to −531 in SEQ ID NO:1
```
                           T AGGGAAGGGA ATAGATGGCT CTACCAATGT
-500 CCAAAGTACT GGTGGAACAG AAGGATCAGA AGGATTGCGA AAGACGGGTC
-450 GGAACATGAT GCCTAATAGA GTAAGTAAGG AGTTGGTGCT GTAACTAGTC
-400 ACAAGTTACG AGTTGTGTAC ATAACATCAT TAGTCATGAA GATCAATTGC
-350 CTTTATGCTT CCGTAACTCT CGCCTCCCCG GAGTCACGAG ATCAATAGAA
-300 ACCACCGCCG TTGACCATTC GCGATGCTCT CACTGGCTGT ATGCTGTCGA
-250 TAGCCATGGA GCCATTCAAA GTATGGACCC TTTGGGTGAG GATCTCCCTC
-200 CAACCCCACG GGACGTACAC GAACAACCGA GCAGAGGCGG GGGAGGGCAA
-150 AGAGGCCGGC GCTGCAAATC GGCTGGCAGA TCAGTCGCGG CTCAGCAGAG
-100 ACTCCCGATT TTCCCTTCCG TTGCCTGGCT TTGCCTCGGG GTTCGAGAGG
 -50 AGCCCGTCTG CCATAAATAA GCCTGCACTT CAACTCAAAA AAAAGGGAGA
```

Fig. 10

BREF51 (SEQ ID NO:4):
5'-AC<u>TAGTCA</u>CAAGTTACGA|GTTGTGTACATAAC|ATCA<u>TTAGTCA</u>TGAAGATC-3'

Modified Fragments:

```
     1   ACAAATCACAAGTTACGAGTTGTGTACATAACATCATTAGTCATGAAGATC   SEQ ID
NO:9
     2   ACTAGAAACAAGTTACGAGTTGTGTACATAACATCATTAGTCATGAAGATC   SEQ ID
NO:10
     3   ACTAGTCACAAGTTACGAGTTGTGTACATAACATCATAAATCATGAAGATC   SEQ ID
NO:11
     4   ACTAGTCACAAGTTACGAGTTGTGTACATAACATCATTAGAAATGAAGATC   SEQ ID
NO:12
     5   ACTAGTCACAAGTTACGAGTTGTGTACATAACATCATTAGTCATAAAGATC   SEQ ID
NO:13
     6   ACTAGTCACAAGTTACGAGTTGTGTACATAACATCATATTAATTGAAGATC   SEQ ID
NO:14
```

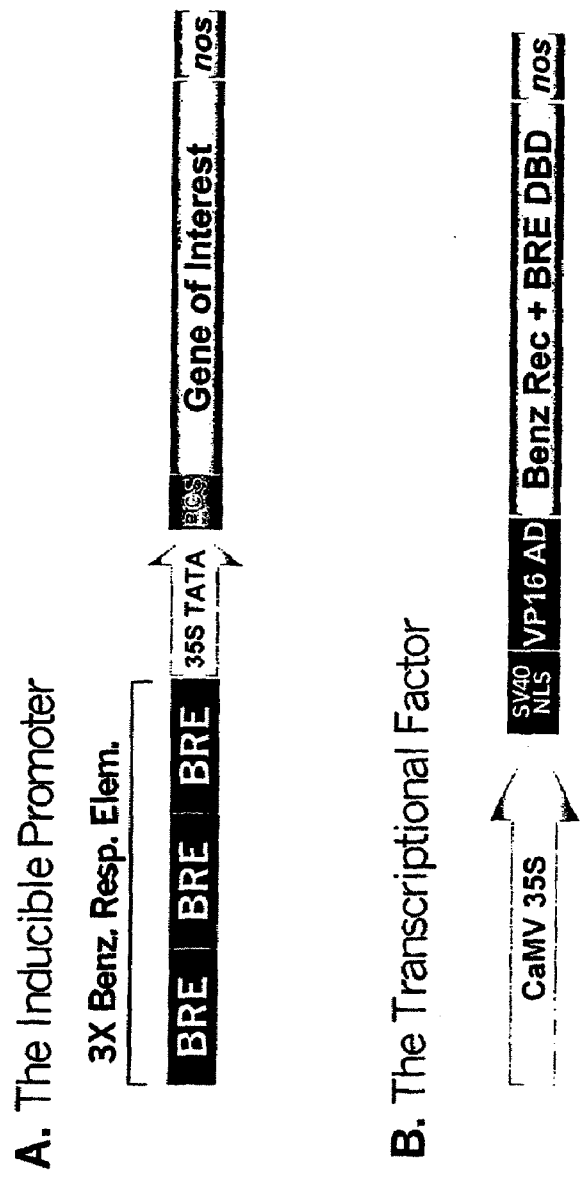

Fig. 16

**GAD1 *A. niger* (full cDNA clone)**
Amino Acid Sequence is SEQ ID NO:15
Nucleic Acid Sequence is SEQ ID NO:16

```
atggtctccttcaagtctcttctgaccgccaccaccctggccaccgccgttctggccatc
 M  V  S  F  K  S  L  L  T  A  T  T  L  A  T  A  V  L  A  I
cctcatagtggccacggccatggcagccacaagcaccgttccacccatgtcgcctccaag
 P  H  S  G  H  G  H  G  S  H  K  H  R  S  T  H  V  A  S  K
cggacctcttcctccaagcgtggcgctgcctacaactctgcttccagcgttcacacgctg
 R  T  S  S  S  K  R  G  A  A  Y  N  S  A  S  S  V  H  T  L
acctccggctcctccggcaacggtaccgtctcctgggcctacgactggaacatgtacgcc
 T  S  G  S  S  G  N  G  T  V  S  W  A  Y  D  W  N  M  Y  A
gacggcaccctccccagtaacgtcgaatacgtgcccatgctgtggggcagcaagatgttt
 D  G  T  L  P  S  N  V  E  Y  V  P  M  L  W  G  S  K  M  F
ggaggctggttgaccgccatcgagactgccctggacagcggtagcaattacatcatggga
 G  G  W  L  T  A  I  E  T  A  L  D  S  G  S  N  Y  I  M  G
ttcaacgagcctgactcctcctcccaagcctcgatgactgcttccgaggccgccagctcc
 F  N  E  P  D  S  S  S  Q  A  S  M  T  A  S  E  A  A  S  S
tacaagaattacatcactccttactctggcaaggctaagctcgtcacccggccgtgacc
 Y  K  N  Y  I  T  P  Y  S  G  K  A  K  L  V  T  P  A  V  T
agtagcaccacggaaggcgagggtctcagctggatgaagtccttcctgtccgaatgcagc
 S  S  T  T  E  G  E  G  L  S  W  M  K  S  F  L  S  E  C  S
gagtgtgacatgtcggtgctggcagtccactggtacggcacctcggccgatgagttcaag
 E  C  D  M  S  V  L  A  V  H  W  Y  G  T  S  A  D  E  F  K
tccttcgtgcaggaggccatgcaggtggcggacgacaacggattggacgagacctgggtg
 S  F  V  Q  E  A  M  Q  V  A  D  D  N  G  L  D  E  T  W  V
acagaattcgccctcaccagcgacgagtctgccggcggcgatgagagttcagcggcggac
 T  E  F  A  L  T  S  D  E  S  A  G  G  D  E  S  S  A  A  D
ttccttgacgaaggcgtgggacggtatgcgtattacatgtgtgcagatgggtatctgctc
 F  L  D  E  G  V  G  R  Y  A  Y  Y  M  C  A  D  G  Y  L  L
agcggggaggagttgagctcgagtggaaaggtctacgttgcatag
 S  G  E  E  L  S  S  S  G  K  V  Y  V  A  -
```

Fig. 17

**GAD11 *A. niger* (partial cDNA clone)**
Amino Acid Sequence is SEQ ID NO:17
Nucleic Acid Sequence is SEQ ID NO:18

```
gactcggctgaatctcggtttagccttcactctcaaggatcagtgccaccggcgccttcg
 D   S   A   E   S   R   F   S   L   H   S   Q   G   S   V   P   P   A   P   S
acggctaccaaacacatgacccctcacaatcacacaataaccacggtggtccactaccg
 T   A   T   K   H   M   T   P   H   N   H   T   N   N   H   G   G   P   L   P
tcgaaacctggatcggaagggcctcgaataatggcacccagatcactggtcctcatgag
 S   K   P   G   S   E   G   A   S   N   N   G   T   Q   I   T   G   P   H   E
tccaatctcatcgagcagttccgtgagcgggaagacaagctgtgggcttatgtccgctcg
 S   N   L   I   E   Q   F   R   E   R   E   D   K   L   W   A   Y   V   R   S
gtgcacgaagaattaaatggacttcggacggaagttgccgctctaagggcccaacttgca
 V   H   E   E   L   N   G   L   R   T   E   V   A   A   L   R   A   Q   L   A
tcagctaacgtcaacgcgctagcaatgtcaagccaaagtgcacctcagtctcaacccgag
 S   A   N   V   N   A   L   A   M   S   S   Q   S   A   P   Q   S   Q   P   E
acaaacgctgctggtacatccaacggtga
 T   N   A   A   G   T   S   Q   -
```

Fig. 18

**GAD1 Homolog from *A. nidulans***
Amino Acid Sequence is SEQ ID NO:34
Nucleic Acid Sequence is SEQ ID NO:35

```
atggtctccttcaagtcgcttgccgctctggccttcttgccagctctgcgctcgccgct
 M  V  S  F  K  S  L  A  A  L  A  L  L  A  S  S  A  L  A  A
cccatggccatgctcacactaccttgcacaagctcgagcccgtcaagcgcgcgtccaac
 P  H  G  H  A  H  T  T  L  H  K  L  E  P  V  K  R  A  S  N
acgacgaccttcctccaagcgcggcgccgcttacaacgatgcctcctcgtcgaggccctc
 T  T  T  S  S  K  R  G  A  A  Y  N  D  A  S  L  V  E  A  L
gcttcctccggcaccatctcctgggcctacgattggaacatgtacaccatgggcgatctc
 A  S  S  G  T  I  S  W  A  Y  D  W  N  M  Y  T  M  G  D  L
cccagcaatgtcgagttcgtgccgatgctctggggtacaaagatgttcaccggctggttc
 P  S  N  V  E  F  V  P  M  L  W  G  T  K  M  F  T  G  W  F
gccgcgatccagacgctcttgaactctggaaacaactacatccttggtttcaacgagccg
 A  A  I  Q  T  L  L  N  S  G  N  N  Y  I  L  G  F  N  E  P
gacatggcgtctcaggccgcgatgtcctcgtccgatgctgccaaatactataagaactat
 D  M  A  S  Q  A  A  M  S  S  S  D  A  A  K  Y  Y  K  N  Y
atcagcaccttcgccggcaagtcaaagctcgtctcgcccgcggtcaccaacggcgaggga
 I  S  T  F  A  G  K  S  K  L  V  S  P  A  V  T  N  G  E  G
gacgacgtcggtctcaactggatgcgcaacttcctgaactcctgtacagactgcgacgtc
 D  D  V  G  L  N  W  M  R  N  F  L  N  S  C  T  D  C  D  V
gatgctcttgctgtccactggtacggtgactcggcagacgacttcaaggccttcgttgaa
 D  A  L  A  V  H  W  Y  G  D  S  A  D  D  F  K  A  F  V  E
aaggccaccgcgctggctgacgagttcggtctcagcgaaacctgggttacggagtttgcg
 K  A  T  A  L  A  D  E  F  G  L  S  E  T  W  V  T  E  F  A
ctcaactcggatttgtccggctccgcggatgccagcacttcggcggacttcttgagcgag
 L  N  S  D  L  S  G  S  A  D  A  S  T  S  A  D  F  L  S  E
gtgctgccttggttggatgaacatgacaaggtcagccgctatgcgtacttcatgtgctcg
 V  L  P  W  L  D  E  H  D  K  V  S  R  Y  A  Y  F  M  C  S
gatggccatctgctcagtggaaacagcttgagcgtgagtggaaaggcgtatgtttcttga
 D  G  H  L  L  S  G  N  S  L  S  V  S  G  K  A  Y  V  S  -
```

Fig. 19

**GAD11 homolog *A. nidulans***
Amino Acid Sequence is SEQ ID NO:36
Nucleic Acid Sequence is SEQ ID NO:37

```
atgacttcgatctatctagctcttggccaccatcatccatcgtttcgaggtagcgtgaaa
 M  T  S  I  Y  L  A  L  G  H  H  H  P  S  F  R  G  S  V  K
gacccggtaccatggccgcgttgatgcagtcaaacaacgagcccgtcgccatctcaacc
 D  P  V  P  M  A  A  L  M  Q  S  N  N  E  P  V  A  I  S  T
cctttgaccgcctcatcggacccgattgcctcgagttccccgggatctgctaccttttta
 P  L  T  A  S  S  D  P  I  A  S  S  P  G  S  A  T  F  L
aaacagtctaaacctgactcgaacctcacctccattgccaacgcggggttaaacgtgacg
 K  Q  S  K  P  D  S  N  L  T  S  I  A  N  G  L  N  V  T
cgatcaaaagactccttaccggcgatgtcaacaacagcagtgccaaactctggctccgcg
 R  S  K  D  S  L  P  A  M  S  T  T  A  V  P  N  G  S  A
gagcggcagctcgaatctcatagagatgcggaccaggatagctctcaggttgcgcgcgaa
 E  R  Q  L  E  S  H  R  D  A  D  Q  D  S  S  Q  V  A  R  E
gcgctcggcgctagtgagaaacatcagtctagctctgtcggcgactcactagccatacac
 A  L  G  A  S  E  K  H  Q  S  S  S  V  G  D  S  L  A  I  H
tccgaccaaatgcaggtcgactctcatcctggtcccggtgaagcgggcgatccggttttc
 S  D  Q  M  Q  V  D  S  H  P  G  P  G  E  A  G  D  P  V  F
aacactgctgagaacggaacttctttaataaacagctcgactgtagcaagccccggaccc
 N  T  A  E  N  G  T  S  L  I  N  S  S  T  V  A  S  P  G  P
atagaagattctgtctctcaggacggtgaccaaccgcgtcatcgagacgacggcgacttg
 I  E  D  S  V  S  Q  D  G  D  Q  P  R  H  R  D  D  G  D  L
catcaagaaaataataacaaagctttctcatacccatgcctacaggggcgttcaacgac
 H  Q  E  N  N  N  K  A  F  S  Y  P  M  P  T  G  A  F  N  D
ccccggcgtggtctcagcttaccaagctccggcctccacaaggctggtcaacggtctcca
 P  R  R  G  L  S  L  P  S  S  G  L  H  K  A  G  Q  R  S  P
tccgctaagaagcatagatgcccctattgcgcaacggagttcacacgacatcacaacctc
 S  A  K  K  H  R  C  P  Y  C  A  T  E  F  T  R  H  H  N  L
aaaagccacctcctcacacatagtcaagagaagccgtttgtatgcacgacctgtcagtca
 K  S  H  L  L  T  H  S  Q  E  K  P  F  V  C  T  T  C  Q  S
cgcttccggcgacttcatgacctcaaaagacaccaaaagcttcatactggtgagcgaccc
 R  F  R  R  L  H  D  L  K  R  H  Q  K  L  H  T  G  E  R  P
catatatgtccgaagtgcggacgcaggtttgctcgcggtgatgcccttgcgcgtcataat
 H  I  C  P  K  C  G  R  R  F  A  R  G  D  A  L  A  R  H  N
aagggccaaggtggctgtgctggtcgtagggccagcatgggaagttacgcacccgaagat
 K  G  Q  G  G  C  A  G  R  R  A  S  M  G  S  Y  A  P  E  D
gagtatggtgatgccgcagctgctggtgccgacgaggctatggatgggctagtttacgcc
 E  Y  G  D  A  A  A  A  G  A  D  E  A  M  D  G  L  V  Y  A
gagccggaacgcatggatgaagatgatgaacgacgttacaacatgccgagcataaagaag
 E  P  E  R  M  D  E  D  D  E  R  R  Y  N  M  P  S  I  K  K
catgatgtgccctcggattctgccgttcgctcaaacagcgtaagcagctatcaagcgcgt
 H  D  V  P  S  D  S  A  V  R  S  N  S  V  S  S  Y  Q  A  R
caacctagcacttaccctccaattgccgcgagcagaccgtcgcctggcgggcttttccct
 Q  P  S  T  Y  P  P  I  A  A  S  R  P  S  P  G  G  L  F  P
cctcctacaagtcatggcggttctagtgcctcccttctcccatatctcagtccggcaat
 P  P  T  S  H  G  G  S  S  A  S  P  S  P  I  S  Q  S  G  N
```

Fig. 19 (cont.)

```
atggcgttcccctcgacaaaccagccatctggctcctctgcttttgcgccttcaaacatg
 M  A  F  P  S  T  N  Q  P  S  G  S  S  A  F  A  P  S  N  M
gctgaaagtccaagaccgctctcaccgaacgcactatcttcccaccaattaggacacggg
 A  E  S  P  R  P  L  S  P  N  A  L  S  S  H  Q  L  G  H  G
ccggaaaacggtctacaaatgcaccatcgcgcccactctgctggaatctcacatccattc
 P  E  N  G  L  Q  M  H  H  R  A  H  S  A  G  I  S  H  P  F
cctcaacaatcatacaatcgtacaggcccctctcaggcttctctttccaaccacactgca
 P  Q  Q  S  Y  N  R  T  G  P  S  Q  A  S  L  S  N  H  T  A
ccgagcttaggccttccaccacctcagcccggggcccctcaacttccgccgccacctggc
 P  S  L  G  L  P  P  P  Q  P  G  A  P  Q  L  P  P  P  P  G
ttggggtcttctgagcctcgttttccctccactcgcaaagctccgtacaggcttccggt
 L  G  S  S  E  P  R  F  S  L  H  S  Q  S  S  V  Q  A  S  G
tccgccgctaaacatacgccatcacatagccactcgagtaatcacggtggttctttgact
 S  A  A  K  H  T  P  S  H  S  H  S  S  N  H  G  G  S  L  T
tccaagacaatccccgaagcagcatcaacgcataacgtccatacctctcacgatccgagc
 S  K  T  I  P  E  A  A  S  T  H  N  V  H  T  S  H  D  P  S
gtcttcgatcagcaacgggaacgggaggaaaagctctgggagtacattcgctcagttcat
 V  F  D  Q  Q  R  E  R  E  E  K  L  W  E  Y  I  R  S  V  H
gaggaactaaatggactcaagtcggaggtagccaccctcagggcacaagtggcatcgtcg
 E  E  L  N  G  L  K  S  E  V  A  T  L  R  A  Q  V  A  S  S
agtgtgaacgcatcgactacgtctggttctagtgttacacaatcatcagttgagacgggc
 S  V  N  A  S  T  T  S  G  S  S  V  T  Q  S  S  V  E  T  G
accacaaatacggtgcaacggtga
 T  T  N  T  V  Q  R
```

BENZOATE INDUCIBLE PROMOTERS

The present Application claims priority to U.S. Provisional Application Ser. No. 60/426,060 filed Nov. 13, 2002 and U.S. Provisional Application Ser. No. 60/425,760 filed Nov. 12, 2002, both of which are herein incorporated by reference.

FIELD OF THE INVENTION

Benzoate inducible promoters and promoter systems are disclosed, and uses thereof. Polynucleotides disclosing Benzoate Response Elements are also disclosed.

BACKGROUND OF THE INVENTION

The application of genetic engineering techniques to plants promises to revolutionize plant agriculture. One result of this revolution would be the ability to control gene expression in plants. For example, pests and diseases have been controlled by applying pesticides or biocides to crop plants; however, application of chemicals to plants affects more than the plant pests or diseases whose control is desired, and poses a general risk to the environment, often with deleterious consequences. In an effort to ameliorate these risks, transgenic plants have been recently developed to constitutively express insect resistance genes or disease resistance genes. However, constitutive expression means that these resistance genes are always expressed, not just when and where and to what level they are needed; such general expression can represent a metabolic drain on a plant, with consequent decreased productivity, or it can be too low to be effective. Moreover, constitutive expression of a protein may not be desirable, particularly if this protein interferes with the early stages of plant development. In other instances, high protein levels cause toxicity to the plant.

Thus, in the last few years, there has been increasing interest among plant scientists on means to precisely control the location, timing and level of expression of transgenes in plants, as well as of endogenous genes. Controlling the location of gene expression, or a more precise control of transgene expression in a specific plant tissue, has been accomplished by means of using one of several different tissue-specific promoters. Controlling the timing and level of gene expression, or temporal and quantitative control of expression, could be accomplished by inducing gene expression upon the application of a specific stimulus. Such inducible gene expression would have numerous practical applications; for example, turning on engineered plant defense genes only upon attack of a pathogen or insect predator could save millions of dollars in pesticide application, as well as decrease unwanted adverse environmental effects. Inducing gene expression would also be a powerful research tool, where it could be used in studies ranging from examining phenotypes associated with specific gene expression to investigations of gene interactions in plants.

One type of inducible promoter is a chemically inducible promoters. These are synthetic promoter systems often constructed by combining known regulator elements whose activity is modulated by the presence of chemical effectors.

A chemically inducible promoter preferably satisfies several criteria to be useful in an agricultural application. Such criteria include sufficient stability and relative non-toxicity of chemical inducers. Chemically-induced gene promoters have been isolated, but none of these are suitable for practical application because of the nature of the chemical inducers. The chemicals are either too volatile (such as ethanol) or toxic to the environment or the plants to which it is applied (such as copper ions, antibiotics, or steroids).

Thus, what is needed are inducible promoters that are activated by chemicals which are sufficiently stable and non-toxic to the environment, including the plants to which they are applied. Preferably such chemical inducers can also be easily applied to large acreages of crop plants; even more preferably, such chemical inducers are inexpensive.

SUMMARY OF THE INVENTION

The present invention provides inducible promoters that are activated by chemicals that are stable and non-toxic to the environment, including the organisms, and in particular to plants, to which they are applied. The present invention also provides chemically inducible promoters where the chemical inducers can also be easily applied to large acreages of crop plants, and further where the chemical inducers are inexpensive.

The present invention provides novel chemically inducible promoters, promoter response elements, and promoter systems, modification of the promoters for use in host cells, and use of the promoters and/or modified promoters and promoter response systems in host cells to control gene expression, where the inducing chemical is both stable and non-toxic. An exemplary inducible promoter was isolated from *Aspergillus niger*. Specifically, a novel chemically inducible promoter and promoter system identified in *Aspergillus niger* is induced by benzoate and related compounds.

Thus, the present invention provides novel benzoate inducible promoters, promoter response elements, modified or hybrid benzoate inducible promoters, and promoter systems. In some embodiments, the present invention provides an isolated nucleic acid sequence of a benzoate inducible promoter region, where the promoter region is induced by the presence of benzoate and/or related chemicals (e.g., benzoate mimetics). In particular embodiments, the present invention provides an isolated nucleic acid sequence of a benzoate inducible promoter region from a fungus; in further particular embodiments, the benzoate inducible promoter region is from *Aspergillus niger*. In other particular embodiments, the benzoate inducible promoter region is from a bphA gene; in further particular embodiments, the bphA gene is from *Aspergillus niger*.

In particular embodiments, the present invention provides an isolated DNA molecule selected from the group consisting of the nucleic acid sequence comprising positions −1 to −531 of SEQ ID NO: 1 (SEQ ID NO:6), a 0.32 kb fragment (SEQ ID NO:2), comprising positions −199 to −521 of SEQ ID NO:1), a 200 bp fragment (SEQ ID NO:3), comprising positions −331 to −531 of SEQ ID NO:1, BREF51 (SEQ ID NO:4), comprising positions −357 to −407 within SEQ ID NO:1, BRE6 (SEQ ID NO:5) comprising a 6 bp sequence TAGTCA, repeated twice in BREF51 but shown most active at position −365 to −370, any fragment of SEQ ID NO:4 that is at least about 20, or 30 base pairs in length and that also comprises a correctly positioned SEQ ID NO:5; any fragment of SEQ ID NO:6 that is at least about 20 base pairs in length and that also comprises at least one benzoate response element (SEQ ID NO:5) (FIG. 1).

In some embodiments, the present invention provides compositions comprising: a) a benzoate inducible promoter comprising; i) a benzoate response element comprising at least one copy of BRE6 sequence TAGTCA (or complement thereof); and ii) a heterologous gene promoter, and b) a nucleic acid sequence of interest, wherein the nucleic acid sequence of interest is operably linked to the benzoate inducible promoter (e.g. linked such that the benzoate inducible promoter can drive expression of the nucleic acid sequence of interest when exposed to benzoate type compound such as benzoic acid or similar compound).

In certain embodiments, the heterologous gene promoter comprises a minimal gene promoter (e.g. at least a minimal plant promoter). In particular embodiments, the benzoate response element comprises a fragment of SEQ ID NO:6 or SEQ ID NO:1, wherein the fragment is at least 15 or at least 20 or at least 30 base pairs in length. In certain embodiments, the nucleic acid sequence of interest comprises a heterologous gene sequence.

In particular embodiments, the benzoate response element comprises at least two copies of the BRE6 sequence TAGTCA (e.g. two copies, three copies or ten copies). In certain embodiments, the benzoate response element comprises a first BRE6 sequence (TAGTCA) and a second BRE6 sequence (TAGTCA), and said first and second BRE6 sequence are separated by 29 bases (e.g. any 29 bases, or the 29 bases between the two BRE6s shown in FIG. 8). In other embodiments, the benzoate response element further comprises palidromic sequence GTTGTGTACATAAC (SEQ ID NO:7). In some embodiments, the benzoate response element comprises a sequence selected from SEQ ID NO:2, SEQ ID NO:3, SEQ ID NO:4, SEQ ID NO:5, SEQ ID NO:6, and SEQ ID NO:8, or the complement thereof.

In additional embodiments, the heterologous gene promoter is a plant promoter (e.g. a plant minimal promoter, or a CaMV 35S promoter). In other embodiments, the benzoate inducible promoter and the nucleic acid sequence of interest are located on a vector. In some embodiments, the vector further comprises a nucleic acid sequence encoding a transcription factor (e.g. a transcription needed in order for the benzoate response element to function as a benzoate inducible promoter). In some embodiments, the compositions of the present invention comprise a transcription factor or a vector encoding a transcription factor. In certain embodiments, the transcription factor is GAD1 (see FIG. 16), GAD11 (see FIG. 17), a GAD1 homolog (see FIG. 18), a GAD11 homolog (see FIG. 19), or a functional fragment of any one of these. In certain embodiments, the benzoate inducible promoter is a benzoate inducible hybrid promoter.

In some embodiments, the present invention provides a transgenic plant comprising: a) a benzoate inducible promoter comprising; i) a benzoate response element comprising at least one copy of BRE6 sequence TAGTCA; and ii) a heterologous gene promoter, and b) a nucleic acid sequence of interest, wherein the nucleic acid sequence of interest is operably linked to the benzoate inducible promoter. In certain embodiments, the plant, when contacted with a benzoate type compound such as benzoic acid is configured to express said nucleic acid sequence of interest (e.g. a disease or pest resistance gene). In certain embodiments, the transgenic plants of the present invention are growing in a field and benzoic acid or similar compound is sprayed on the plants (e.g. to induce the expression of the nucleic acid sequence of interest).

In certain embodiment, the present invention provides a transgenic seed comprising: a) a benzoate inducible promoter comprising; i) a benzoate response element comprising at least one copy of BRE6 sequence TAGTCA; and ii) a heterologous gene promoter, and b) a nucleic acid sequence of interest, wherein the nucleic acid sequence of interest is operably linked to the benzoate inducible promoter.

In some embodiments, the present invention provides methods of transfecting a cell comprising; a) providing: i) a vector comprising; A) a benzoate inducible promoter comprising; I) a benzoate response element comprising at least one copy of BRE6 sequence TAGTCA; and II) a heterologous gene promoter, and B) a nucleic acid sequence of interest, wherein the nucleic acid sequence of interest is operably linked to the benzoate inducible promoter; and ii) a target cell; and b) contacting the vector with the vector under conditions such that the target cell is transfected and expresses the nucleic acid sequence of interest when the target cell is contacted with benzoate type compound such as benzoic acid or similar compound. In certain embodiments, the target cell is part of a plant.

In certain embodiments, the present invention provides nucleic acid sequences selected from the group consisting of SEQ ID NOs:16, 18, 35 and 37 (See FIGS. 16-19). In other embodiments, the present invention provides fragments or variants of SEQ ID NOs:16, 18, 35, and 37. In some embodiments, the present invention provides amino acid sequences selected from SEQ ID NOs:15, 17, 34 and 36 (See FIGS. 16-19). In additional embodiments, the present invention provides fragments and variants of SEQ ID NOs:15, 17, 34, and 36.

In other embodiments, the present invention provides an isolated DNA molecule comprising a benzoate inducible promoter which hybridizes under high stringency to any of the isolated DNA molecules described above.

In other embodiments, the present invention provides an isolated DNA molecule comprising a promoter, wherein the promoter is a benzoate inducible promoter and comprises any of the DNA molecules described above. In further embodiments, the DNA molecule further comprises a heterologous gene is operably linked to the benzoate promoter. In further embodiments, the DNA molecule further comprises a termination sequence.

In other embodiments, the present invention provides an isolated DNA molecule comprising a benzoate inducible hybrid promoter, which hybrid promoter comprises at least one benzoate response element within a heterologous gene promoter region. In some further embodiments, the heterologous gene promoter region is a minimal gene promoter. In particular embodiments, the at least one benzoate response element comprises SEQ ID NO:5.

In other embodiments, the present invention provides an expression vector comprising an isolated DNA molecule comprising a promoter, wherein the promoter is a benzoate inducible promoter and comprises any of the benzoate inducible promoters or benzoate inducible hybrid promoters above. In some further embodiments, the expression further comprises a cloning site such that a nucleic acid sequence of interest can be inserted into the vector and operably linked to the promoter or hybrid promoter. In other further embodiments, the vector further comprises a heterologous gene operably linked to the benzoate promoter or benzoate inducible hybrid promoter. In yet other embodiments, any of the vectors described above further comprises a termination sequence.

In another aspect, the present invention provides a transgenic cell comprising a heterologous benzoate inducible promoter, where the promoter region is induced by the presence of benzoate and/or related chemicals. In particular embodiments, the benzoate inducible promoter is from a fungus; in further particular embodiments, the benzoate inducible promoter region is from *Aspergillus niger*. In other particular embodiments, the benzoate inducible promoter region is from a bphA gene; in further particular embodiments, the bphA gene is from *Aspergillus niger*. In yet other embodiments, the present invention provides a transgenic cell comprising any of the DNA molecules described above. In other embodiments, the present invention provides a transgenic cell comprising any of the benzoate inducible promoters or benzoate inducible hybrid promoters described above, which promoters comprise any of the DNA molecules described above. In some embodiments, the cell is a eukaryotic cell; in other embodiments, the cell is a prokaryotic cell. In yet other embodiments, the cell is a plant cell or an animal cell.

In another aspect, the present invention provides a transgenic plant or plant seed comprising a heterologous benzoate inducible promoter region, where the promoter region is induced by the presence of benzoate and/or related chemicals. In particular embodiments, the benzoate inducible promoter is from a fungus; in further particular embodiments, the benzoate inducible promoter region is from *Aspergillus niger*. In other particular embodiments, the benzoate inducible promoter region is from a bphA gene; in further particular embodiments, the bphA gene is from *Aspergillus niger*. In yet other embodiments, the present invention provides a transgenic plant or plant seed comprising any of the DNA molecules described above. In other embodiments, the present invention provides a transgenic plant or plant seed comprising any of the benzoate inducible promoters or benzoate inducible hybrid promoters described above, which promoters comprise any of the DNA molecules described above.

The present invention also provides a purified molecule, wherein the molecule is a transacting factor necessary and sufficient to induce any of the benzoate inducible promoters or benzoate inducible hybrid promoters as described above. In some embodiments, the factor is a transcription factor (e.g. GAD1, a GAD1 homolog, GAD11, or a GAD11 homolog; see FIGS. 16-19).

The present invention also provides a composition comprising a benzoate inducible promoter system, wherein the benzoate inducible promoter system comprises: a benzoate inducible promoter or benzoate inducible hybrid promoter as described above; and at least one additional nucleic acid sequence encoding a factor necessary and sufficient for induction of the benzoate inducible promoter by benzoate and/or related chemicals. In some further embodiments, the inducible promoter or inducible hybrid promoter is linked to a cloning site such that a nucleic acid sequence of interest can be inserted into the cloning site and operably linked to the promoter or hybrid promoter. In other further embodiments, the inducible promoter or inducible hybrid promoter is operably linked to a heterologous gene. In other embodiments, the at least one additional nucleic acid sequence encoding a factor is operably linked to a promoter. In further embodiments, the promoter operably linked to the at least one additional nucleic acid sequence encoding a factor is a constitutive promoter. In other embodiments, the factor is a transcription factor. In other embodiments, the benzoate inducible promoter or benzoate inducible hybrid promoter and the at least one additional nucleic acid sequence encoding a factor of the benzoate inducible promoter system as described above are part of an expression vector; in some embodiments, the promoter and the at least one coding sequence are part of separate expression vectors; in other embodiments, the promoter and the at least one coding sequence are part of the same expression vector.

In another aspect, the present invention provides a method of expressing a nucleic acid sequence of interest in a cell, comprising: providing a transgenic cell comprising a nucleic acid sequence of interest operably linked to any of the benzoate inducible promoters or benzoate inducible hybrid promoters described above; and growing the cell under conditions such that the nucleic acid sequence of interest is expressed in the cell. In some embodiments, the nucleic acid sequence of interest operably linked to any of the benzoate inducible promoters or benzoate inducible hybrid promoters is in an expression vector. In other embodiments, the cell further comprises at least one additional nucleic acid sequence encoding a factor necessary and sufficient for induction of the benzoate inducible promoter by benzoate and/or related chemicals; in some further embodiments, the at least one additional nucleic acid sequence is in an expression vector. In yet other embodiments, the cell is a plant cell.

In another aspect, the present invention provides a method of expressing a nucleic acid sequence of interest in a cell, comprising: providing a transgenic cell comprising a nucleic acid sequence of interest operably linked to any of the benzoate inducible promoters or benzoate inducible hybrid promoters described above; and exposing the cell to benzoate or a related chemical such that the nucleic acid sequence of interest is expressed in the cell. In some embodiments, the nucleic acid sequence of interest operably linked to any of the benzoate inducible promoters or benzoate inducible hybrid promoters is in an expression vector. In other embodiments, the cell further comprises at least one additional nucleic acid sequence encoding a factor necessary and sufficient for induction of the benzoate inducible promoter by benzoate and/or related chemicals; in some further embodiments, the at least one additional nucleic acid sequence is in an expression vector. In yet other embodiments, the cell is a plant cell.

In yet another aspect, the present invention provides a method of inducing expression of a nucleic acid sequence of interest in a cell, comprising: providing a transgenic cell comprising a nucleic acid sequence of interest operably linked to any of the benzoate inducible promoters or benzoate inducible hybrid promoters described above; and exposing the cell to benzoate or a related chemical such that the nucleic acid sequence of interest is expressed in the cell. In some embodiments, the nucleic acid sequence of interest operably linked to any of the benzoate inducible promoters or benzoate inducible hybrid promoters is in an expression vector. In other embodiments, the cell further comprises at least one additional nucleic acid sequence encoding a factor necessary and sufficient for induction of the benzoate inducible promoter by benzoate and/or related chemicals; in some further embodiments, the at least one additional nucleic acid sequence is in an expression vector. In yet other embodiments, the cell is a plant cell.

In another aspect, the present invention provides a method of controlling expression of flowering in a flowering plant, comprising: providing a transgenic plant comprising a gene necessary and sufficient to control flowering operably linked to any of the benzoate inducible promoters or benzoate inducible hybrid promoters described above, wherein the gene regulatory region is a plant gene regulatory region; and exposing the plant to benzoate or a related chemical such that the gene necessary and sufficient to control flowering is expressed in the plant.

In yet another aspect, the present invention provides a method of controlling expression of flowering in a flowering plant, comprising: providing a transgenic plant comprising a gene necessary and sufficient to inhibit flowering operably linked to any of the benzoate inducible promoters or benzoate inducible hybrid promoters described above, wherein the gene regulatory region is a plant gene regulatory region; and exposing the plant to benzoate or a related chemical such that the gene necessary and sufficient to inhibit flowering is expressed in the plant.

In certain embodiments, the present invention provides kits comprising; a) one or more of the compositions described above; and b) a benzoate type chemical or instructions on how to use the compositions of the present invention to transform plant cells (or other cell types) such that they express a sequence of interest when exposed to a benzoate type chemical.

DESCRIPTION OF THE FIGURES

FIG. 1 shows: A. DNA sequence of 1.8 kbp from the *A. niger* bphA gene promoter region (SEQ ID NO:1). Probable TATA Box sequence is underlined. Numbers to the left refer to nucleotide position relative to the transcription start point. Italicized bases correspond to the conserved putative ORF identified by ORF Finder. BREF51 (SEQ ID NO:4) is shaded in gray. The TAGTCA sequence (SEQ ID NO:5) within BREF51 shown to be involved in factor binding in EMSA is double underlined. The proposed Benzoic Acid Response Element from van den Brink et al. (2000), which is situated within an open-reading frame of an adjacent gene that is not induced by benzoate, is boxed. FIG. 1B shows positions −119 to −521 (SEQ ID NO:2) of the bphA gene promoter region. FIG. 1C shows positions −331 to −531 (SEQ ID NO:3) of the bphA gene promoter region. FIG. 1D shows positions −357 to −407 (SEQ ID NO:4; BREF51) of the bphA gene promoter region. FIG. 1E shows positions −365 to −370 (SEQ ID NO:5; BRE6) of the bphA gene promoter region. FIG. 1F shows positions −1 to −531 (SEQ ID NO:6) of the bphA gene promoter region.

Figure 9:
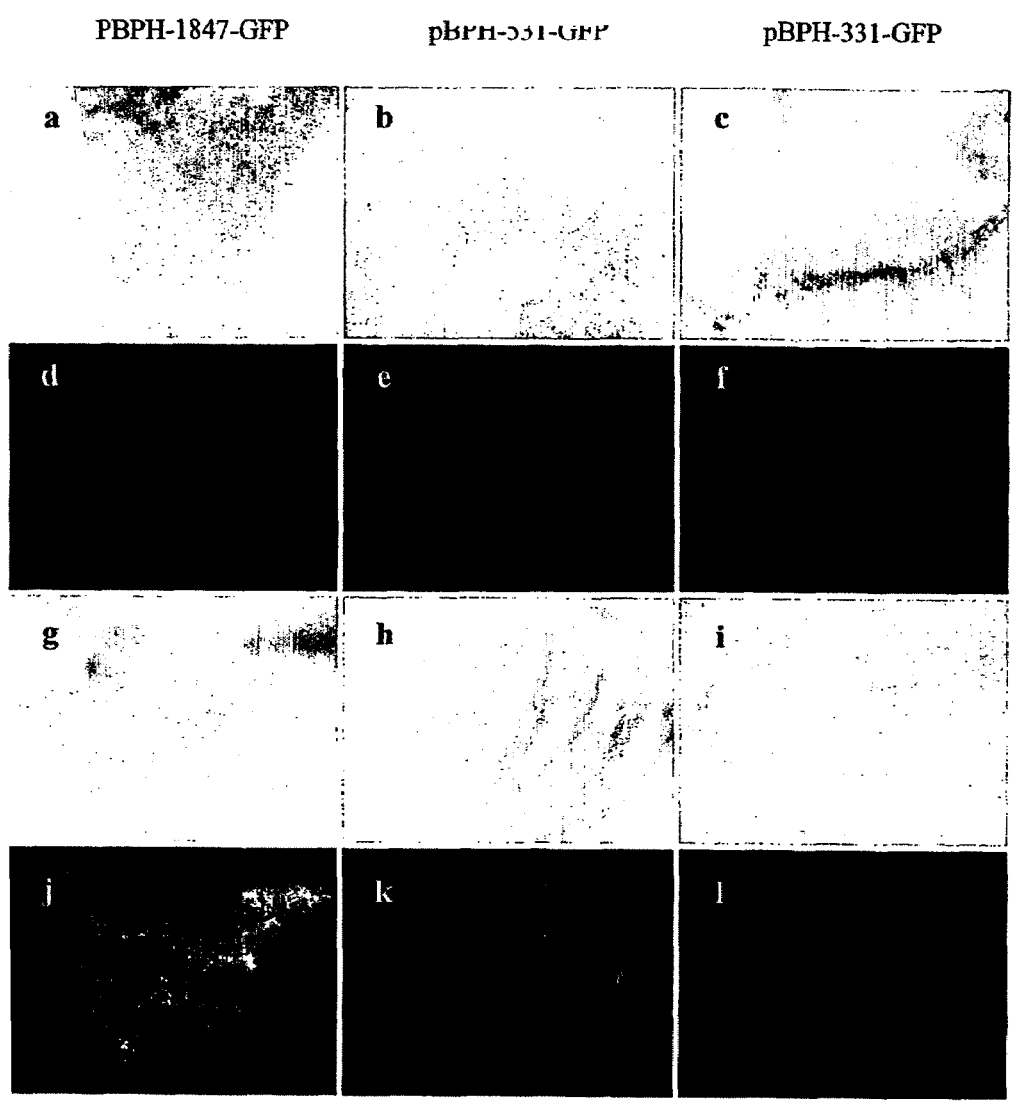
FIG. 9 shows the benzoic acid-dependent GFP expression in *A. nidulans* GR5 strain carrying bphA promoter deletions.

Panels a, b, c, g, h, and are bright field images of the fungal mycelia, and panels d, e, f, j, k, and l are corresponding images of GFP fluorescence; panels a, d, g, and j correspond to −1 to −1847 promoter sequence (SEQ ID NO:1)-GFP strain, panels b, e, h, and k correspond to −1 to −531 promoter sequence (SEQ ID NO:6)-GFP, panels c, f, i, and l correspond to −1 to −331 promoter sequence-GFP; a to f, control, uninduced mycelia; g to l, mycelia induced with 8 mM benzoic acid for 5 h. This experiment shows that not only transcriptional factor binding, but actual gene expression requires the BRE6 within BREF51, and included 200 bp from −332 to −531 (FIG. 9).

FIG. 10 shows an Electrophoretic Mobility Shift Assay (EMSA) of modified BREF51 sequences (SEQ ID NO:4) in which site-directed mutagenesis was used to change either of the two TAGTCA sequences, delete the sequence entirely or modify sequences flanking the downstream TAGTCA. The − and + symbols indicate labeled modified fragments incubated in the absence (−) or in the presence (+) of total protein extracts from *A. niger* cells. Control, indicates labeled BREF51 incubated in the absence (−) or in the presence (+) of total protein extracts. The almost perfect palindromic sequence (SEQ ID NO:7) is boxed. The EMSA shows clearly that only changes to downstream TAGTCA (−364 to −369) abolish the vast majority of the binding.

Figure 11:
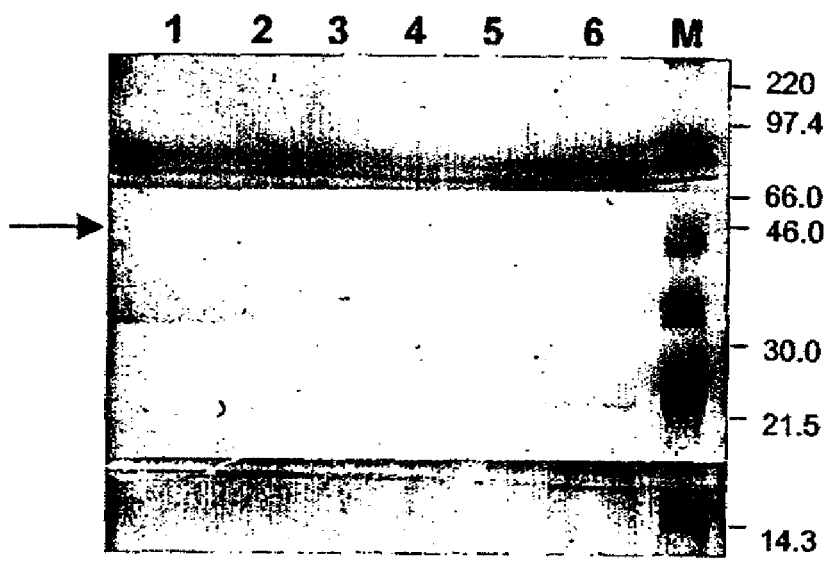

FIG. 11 shows the results of an SDS-PAGE analysis of the fractions obtained from an Affinity Chromatography experiment using BRE as the affinity ligand. The gel was silver stained, and a protein of approximately 46 kD can be observed in the eluted fraction (arrow). Lanes: 1, supernatant fraction; 2, $1^{st}$ wash fraction; 3, $2^{nd}$ wash fraction; 4, $3^{rd}$ wash fraction; 5, $4^{th}$ wash fraction; 6, eluted fraction; M, molecular weight marker (kDa).

Figure 12:
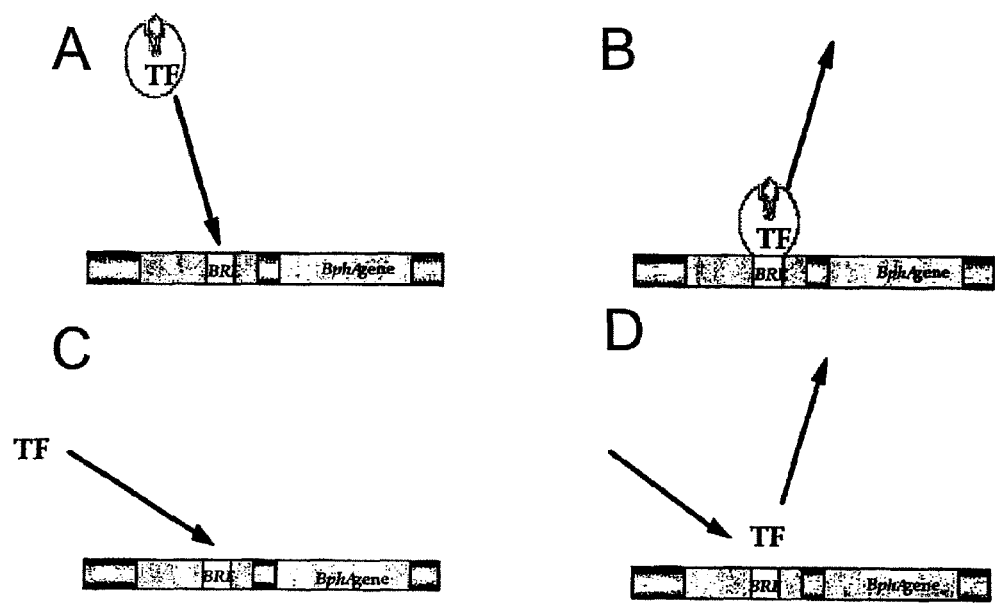

FIG. 12 shows proposed working models for the mechanism of benzoate induction of the bphA gene. It is noted that it is not necessary to understand what mechanism causes benzoate induction of the bphA gene to practice the present invention. In the model shown in panel A, benzoate first binds to a constitutive transcription factor (TF), and the complex binds to the Benzoate Responsive Element (BRE) in the promoter region to activate transcription. In the model shown in panel B, benzoate binds to a transcriptional repressor and induces dissociation. In the model shown in panel C, the benzoate binds to a membrane surface receptor that initiates the release of a specific TF that induces the bphA gene along with other genes required for benzoate uptake and metabolism. In the model shown in panel D, the activation of the membrane surface receptor results in release of a factor that induces dissociation of a repressor element.

Figure 13:
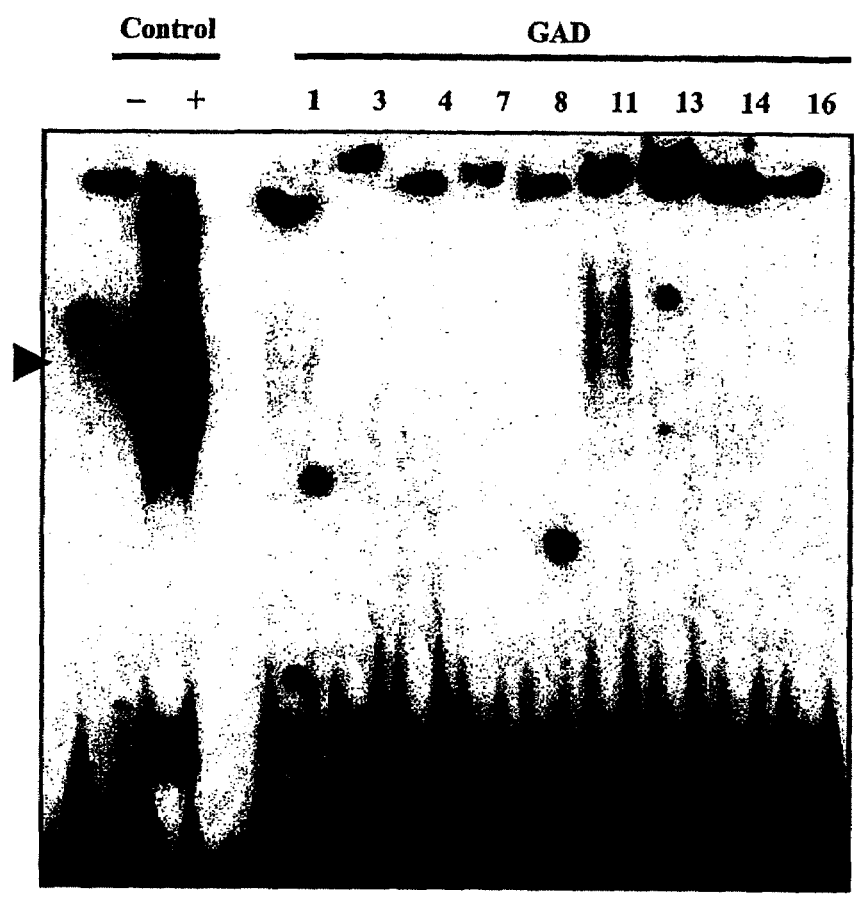

FIG. 13 shows an EMSA of BREF51 (SEQ ID NO:4) in the presence of total protein extracts from nine (of 17 total) selected yeast GAD clones. Lanes, Control−, labeled BREF51 only; Control+, labeled BREF51 plus 1 mg of total protein extracts from *A. niger*; GAD, labeled BREF51 plus 5 mg of total protein extracts from GAD clones (numbers refer to clones as described on Table 1). Arrowhead points to control mobility shifted band. Of the total of 17 clones, only two clones (GAD1 and GAD11), gave positive mobility shifts, and they were in the size range observed with the total protein extracts. The low binding was the result of very small amounts of recombinant protein available. The function of the protein of the GAD1 gene or its homologs in the *A. nidulans* and *Neurospora crassa* genomes is not known. GAD1 (see FIG. 16) is rich in serine residues and predicted by PSORTII to contain a nuclear localization signal. Thus, the protein has the essential characteristics of a transcriptional regulator. GAD11 (see FIG. 17) is weakly similar to a *Drosophila melanogaster* homeotic gene regulator and to a *Caenorhabditis elegans* nuclear-targeted protein.

Figure 14:
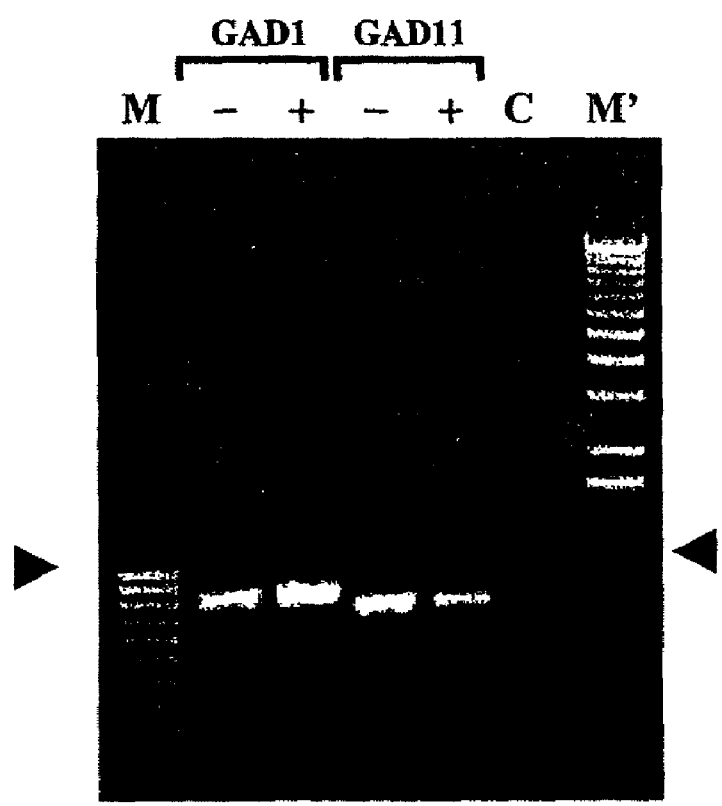

FIG. 14 shows the expression of GAD1 and GAD11 genes in response to benzoic acid. Total RNA samples isolated from uninduced (−) and induced for 5 h in the presence of 8 mM benzoic acid (+) were reverse transcribed using Oligo (dT) primers, and cDNAs amplified using GAD1 and GAD11 gene-specific primers. M, 100 bp molecular weight marker; M', 1 kbp molecular weight marker. C, negative control of RT-PCR. The expression of GAD1 is constitutive, whereas the expression of GAD11 is slightly down-regulated. Expression of a benzoate-activation regulator in the absence of the inducing molecule is expected, but the down-regulation of GAD11 suggests that it functions as a repressor, although an understanding of this is not necessary to practice the present invention.

FIG. 15 shows an embodiment of the benzoate inducible hybrid promoter system. The first DNA construct is the Inducible Promoter itself (panel A), with 3 or more copies of a BRE of the present invention (e.g. BREF51 or other BRE containing a first and/or second copy of BRE6 (SEQ ID NO:5), fused to the TATA-box of the Cauliflower Mosaic Virus 35S promoter (35S TATA). A polycloning site is engineered between the 35S TATA promoter sequence and the Nopaline Synthase (nos) terminator for ease of manipulation. This hybrid promoter drives expression of any downstream gene of interest in a benzoate inducible manner. The nos terminator is placed downstream of the coding region and, in addition to stop codons in every reading frame, contains a polyadenylation signal sequence. The second DNA construct encodes the Transacting Factor or Transcriptional Factor (panel B), which is constitutively expressed by using a full-length CaMV35S promoter. A chimeric transcription factor construct may also be employed that consists of a combination of modules. The first module is the Nuclear Localization Signal (NLS) from the 5V40 viral protein. The Activation Domain (AD) of the Herpes Simplex Viral Protein 16 (VP16) constitutes the second module. The third and final module have the BREF51 DNA binding domain (BRE DBD) fused to the benzoate receptor domain (Benz Rec), both identified from the *A. niger* transcription factor. The nos terminator sequence is also placed downstream of this construct.

FIG. 16 shows the amino acid sequence (SEQ ID NO:15) and nucleic acid sequence (SEQ ID NO:16) of GAD1.

FIG. 17 shows the amino acid sequence (SEQ ID NO:17) and nucleic acid sequence (SEQ ID NO:18) of GAD11.

FIG. 18 shows the amino acid sequence (SEQ ID NO:34) and nucleic acid sequence (SEQ ID NO:35) of a GAD1 homolog.

FIG. 19 shows the amino acid sequence (SEQ ID NO:36) and nucleic acid sequence (SEQ ID NO:37) of a GAD11 homolog.

DEFINITIONS

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae (for example, *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture. The term "plant part" as used herein refers to a plant structure or a plant tissue. The term "seed" as used herein includes all tissues which result from the development of a fertilized plant egg; thus, it includes a matured ovule containing an embryo and stored nutrients, as well as the integument or integuments differentiated as the protective seed coat, or testa. The nutrients in seed tissues may be stored in the endosperm or in the body of the embryo, notably in the cotyledons, or both.

The term "crop" or "crop plant" is used in its broadest sense. The term includes, but is not limited to, any species of plant or algae edible by humans or used as a feed for animals or used, or consumed by humans, or any plant or algae used in industry or commerce.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "benzoate para-hydroxylase (BPH)" refers to an enzyme which catalyzes the hydroxylation of the aromatic ring of benzoic acid at the para position. The enzyme belongs to the class of cytochrome P450 monooxygenases (CYP53A1). In the fungus Aspergillus niger, the enzyme catalyzes the first of a series of steps by which A. niger catabolizes benzoic acid, and is thus able to utilize benzoic acid as a carbon source.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" or "fragment" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (for example, 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One may make variants of the BREs and transcription factors described herein (with functionality of these variants tested as candidates in the protocols described in the Examples below). One type of conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (for example, replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (for example, DNA or RNA) sequence that comprises coding sequences necessary for the production of an RNA, and/or ultimately a polypeptide or its precursor. A functional polypeptide can be encoded by a full length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "heterologous" when used in reference to a gene refers to a gene that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. The term "polynucleotide" refers to a molecule comprised to more than two deoxyribonucleotides or ribonucleotides, and is typically longer than an oligonucleotide. However, the terms "oligonucleotide," "polynucleotide," and "nucleic acid" are often used interchangeably. The length of an oligonucleotide is expressed as a number of base pairs (bp) or nucleotides. Although generally, nucleotides refer to the sense strand, whereas base pair refers to the complementary base on the antisense strand that is understood for DNA, as used herein the terms "base pairs" or "nucleotides" to express the length of an oligonucleotide are used interchangeably. Also as the terms are used herein, it is understood that a length expressed in base pairs does not mean that the molecule must be double stranded, but may exist as paired or unpaired. Likewise, a length expressed as a number of nucleotides does not mean that the molecule may not be double stranded, or in any other form.

The term "nucleotide sequence of interest" or "nucleic acid sequence of interest" refers to any nucleotide sequence (for example, RNA or DNA), the manipulation of which may be deemed desirable for any reason (for example, treat disease, confer improved qualities, etc.), by one of ordinary skill in the art. Such nucleotide sequences include, but are not limited to, coding sequences of structural genes (for example, reporter genes, selection marker genes, oncogenes, drug resistance genes, growth factors, etc.), and non-coding regulatory sequences which do not encode an mRNA or protein product (for example, promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), or an rRNA, an sRNA, a tRNA, etc.

The term "fragment" or "portion" when used in reference to a an oligonucleotide sequence or nucleic acid sequence refers to a length of the sequence which is less than the entire length is it occurs naturally (for example, as a DNA, RNA, or cDNA molecule). The fragments may range in size from a few nucleotides to the entire nucleic sequence minus one nucleotide. Thus, "a nucleotide comprising at least a portion of a gene" may comprise fragments of the gene or the entire gene The term "an oligonucleotide having a nucleotide sequence encoding a gene" or "a nucleic acid sequence encoding" a specified gene product refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (in other words, a sequence of nucleotides)

related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence which is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (in other words, a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (in other words, gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.A.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (in other words, resulting in the highest percentage of homology over the comparison window) generated by the various methods is selected. The term "sequence identity" means that two polynucleotide sequences are identical (in other words, on a nucleotide-by-nucleotide basis) over the window of comparison. The term "percentage of sequence identity" is calculated by comparing two optimally aligned sequences over the window of comparison, determining the number of positions at which the identical nucleic acid base (for example, A, T, C, G, U, or I) occurs in both sequences to yield the number of matched positions, dividing the number of matched positions by the total number of positions in the window of comparison (in other words, the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described below.

The term "substantially homologous" when used in reference to a single-stranded nucleic acid sequence refers to any probe that can hybridize (in other words, it is the complement of) the single-stranded nucleic acid sequence under conditions of low to high stringency as described below.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See for example, Anderson and Young, Quantitative Filter Hybridization, in *Nucleic Acid Hybridization* (1985)). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42EC in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5× SSPE, 0.1% SDS at 42EC when a probe of about 500 nucleotides in length is employed.

"Medium stringency conditions" when used in reference to nucleic acid hybridization comprise conditions equivalent to binding or hybridization at 42EC in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42EC when a probe of about 500 nucleotides in length is employed.

"High stringency conditions" when used in reference to nucleic acid hybridization comprise conditions equivalent to binding or hybridization at 42EC in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42EC when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (in other words, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers generally to a genetic element which controls some aspect of the expression of nucleic acid sequences. For example, under this definition, a promoter is a regulatory element which facilitates the initiation of transcription of an operably linked coding region. More specifically, a regulatory element refers to active oligonucleotide sequences within promoters, within introns, and within the 3' untranslated sequences. Thus, under this more specific definition, a promoter may consist of a collection of several kinds of elements. Other regulatory elements are splicing signals, polyadenylation signals, termination signals, etc.

The term "regulatory region" refers to a gene's 5' transcribed but untranslated regions, located immediately downstream from the promoter and ending just prior to the translational start of the gene.

Transcriptional control signals in eukaryotes comprise "promoter" and "enhancer" and "repressor" elements (discussed further below). Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al, Trends Biochem. Sci., 11:287, 1986; and Maniatis, et al., supra 1987).

The term "promoter region" refers to the region immediately upstream of the coding region of a DNA polymer, and is typically between about 500 bp and 4 kb in length, and is preferably about 1 to about 1.5 kb in length. A promoter region controls or regulates transcription of a gene to which it is operably linked, either naturally or by recombinant nucleic acid technology. A promoter region may include smaller sequences which are effective to control or regulate transcription. One skilled in the art can determine such smaller sequences by creating fragments of decreasing size from a promoter region, and operably linking such fragments to a reporter gene, and determining expression of such constructs in transgenic tissue, as described further herein.

The terms "promoter element," "promoter," or "promoter sequence" refer to a DNA sequence that is located at the 5' end (in other words precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters generally may be tissue specific or cell specific; more specifically, promoters may contain elements that impart tissue or cell specificity. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (for example, peroxidase conjugated) secondary antibody which is specific for the primary antibody is allowed to bind to the sectioned tissue and specific binding detected (for example, with avidin/biotin) by microscopy.

A promoter is "effective" as a tissue specific or cell type promoter when expression in the presence of the promoter is greater in the tissue or cell type than expression in the presence of the promoter in other tissues or cell types. Preferably, the greater level of expression is at least about two-fold greater; more preferably, it is at least about four-fold greater; and most preferably, it is at least about ten-fold greater. An effective promoter may comprise all of the promoter region, or a modification or fragment of a promoter region, or a motif of a promoter region.

Promoters may be constitutive or inducible. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, incorporated herein by reference), mannopine synthase, octopine synthase (ocs), superpromoter (see for example, WO 95/14098), and ubi3 (see for example, Garbarino and Belknap, Plant Mol. Biol. 24:119-127 (1994)) promoters. Such promoters have been used successfully to direct the expression of heterologous nucleic acid sequences in transformed plant tissue.

In contrast, an "inducible" promoter is one which is capable of directing a level of transcription of an operably linked nucleic acid sequence in the presence of a stimulus (for example, heat shock, chemicals, light, etc.) which is different from the level of transcription of the operably linked nucleic acid sequence in the absence of the stimulus.

The term "benzoate inducible promoter" refers to a promoter which is induced by the presence of benzoate and/or related chemicals. Benzoate and related chemicals include but are not limited to benzoic acid and its salts ($Na^+$, $K^+$, $NH_4^+$, etc.), and esterified forms, where the esterified are used to facilitate penetration of the esterified forms into cells and once inside the cells are subsequently be de-esterified to yield active compound by the cell's own esterases. Thus, related chemicals include but are not limited to sodium benzoate and methyl benzoate. It is contemplated, in some embodiments, that features necessary and sufficient for activity are a benzyl ring with one carboxyl group. Derivatives with substitutions at the ortho- and meta-positions of the ring reduce or abolish activity, whereas substitutions at the para-position, such as para-aminobenzoate, are tolerated. It is noted that additional benzoate type compounds can be located by screening a test benzoate type compound in an assay (e.g. as described in the Examples below) known to be induced by benzoic acid. If the test benzoate compound also induces the expression of a sequence (such as GFP) then the compound is a benzoate type compound and is useful with the benzoate inducible promoters of the present invention.

The term "response element" refers to specific short DNA sequence(s) in a promoter of a eukaryotic gene which controls transcription of that particular gene The term "benzoate response element (BRE)" refers to at least one short oligonucleotide sequence that binds to at least one transacting factor within a benzoate inducible promoter in the presence of benzoate; it is contemplated that the oligonucleotide sequence is necessary for attachment of a benzoate-inducing transcriptional factor within the promoter. It is further contemplated that in some embodiments, this sequence comprises either one or a pair of 6 bp repeats of the sequence TAGTCA. In some further embodiments, this pair of short repeated sequences is found in BREF51, where BREF51 is a fragment from the benzoate inducible promoter region of the bphA gene located from −1 to −350 (or −1 to −531) bp upstream of the transcriptional start point, and where BREF51 consistently binds a protein factor present in total protein extracts from benzoate-induced *A. niger* mycelia. BREF51 also possesses benzoate-inducing activity in vivo. In some embodiments, additional sequences surrounding the 6 bp sequence TAGTCA (SEQ ID NO:5) are included as part of the BRE (e.g. 1, 5, 10, 25 or 35 additional bases upstream, downstream, or both upstream and downstream of SEQ ID NO:5 are included. In certain preferred embodiments, a fragment of SEQ ID NO:6 at least 20 base pairs in length that includes TAGTCA (SEQ ID NO:5) is employed. Fragments of SEQ ID NO:6 that would function as BREs (and that are at least 20 base pairs and contain TAGTCA) may be tested in the assays such as those shown in the Examples section below to determine if they will function as effective BREs.

The term "transacting factor" refers to a regulatory protein which binds to a specific short DNA sequence(s) in the regulatory region of a eukaryotic gene controlling transcription of that particular gene. It is contemplated that in a benzoate inducible promoter, a transacting factor is a transcription factor. Transcription factors interact with RNA polymerase, and may interact with each other, to modulate transcription. In some embodiments, GAD1 or GAD11 (or both) serve as transcription factors that interact with the BRE. Transcription factors may interact with promoter elements as either "inducers" or "repressors". Inducers typically bind to a promoter only in the presence of the inducing substances, whereas repressors are bound to the promoter in the absence of the inducer and binding of the inducing molecule releases the repressor to allow transcription (see, e.g, FIG. 12).

The term "benzoate inducible hybrid promoter (BIHP)" refers to a hybrid promoter comprising benzoate responsive elements within a gene regulatory region, such that the hybrid promoter is functional in cells and is responsive to benzoate and related chemical inducers, in the presence of any necessary and sufficient transacting factors.

The term "benzoate inducible promoter system (BIPS)" refers to a combination of nucleotide sequences comprising a benzoate inducible promoter of the present invention, including a benzoate inducible hybrid promoter, and at least one additional gene encoding a factor as necessary, and sufficient for the induction of the promoter component by benzoate and/or related chemicals. In some embodiments, the factor is a transacting factor; in further embodiments, a transacting factor is a transcription factor. The at least one additional gene encoding a factor is under control of a promoter, often a constitutive promoter. Preferably, the benzoate promoter system is present in at least one expression vector, where the expression vector(s) can be used to transfect a host cell, either transiently or stably.

The term "functional equivalence" and its grammatical variants when used in reference to nucleic acid sequences means that the nucleic acid sequences are capable of induction by benzoate and/or related chemicals either by themselves, or when incorporated into a hybrid promoter, when operably linked to a gene of interest.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York (1989) pp. 16.7-16.8). A commonly used splice donor and acceptor site is the splice junction from the 16S RNA of SV40.

Efficient expression of recombinant DNA sequences in eukaryotic cells generally requires expression of signals directing the efficient termination and polyadenylation of the resulting transcript. Transcription termination signals are generally found downstream of the polyadenylation signal and are a few hundred nucleotides in length. The term "poly (A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "termination signal" or "termination sequence" refers to a 3' non-translated DNA sequence which functions in plant cells to cause the addition of polyadenylated ribonucleotides to the 3' end of an mRNA sequence transcribed from a gene; the gene may be an endogenous or native gene, or it may be a heterologous gene. The termination sequence may be endogenous or heterologous to the gene.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences generally necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including, but not limited to, calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (in other words, particle bombardment) and the like. The term "transformation" and its grammatical variants (including but not limited to transform, transformed, and transforming) is used interchangeably with the term "transfection" and its grammatical variants (including transfect, transfected, and transfecting).

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "Agrobacterium" refers to a soil-borne, Gram-negative, rod-shaped phytopathogenic bacterium which causes crown gall. The term "Agrobacterium" includes, but is not limited to, the strains Agrobacterium tumefaciens, (which typically causes crown gall in infected plants), and Agrobacterium rhizogens (which causes hairy root disease in infected host plants). Infection of a plant cell with Agrobacterium generally results in the production of opines (for example, nopaline, agropine, octopine etc.) by the infected cell. Thus, Agrobacterium strains which cause production of nopaline (for example, strain LBA4301, C58, A208, GV3101) are referred to as "nopaline-type" Agrobacteria; Agrobacterium strains which cause production of octopine (for example, strain LBA4404, Ach5, B6) are referred to as "octopine-type" Agrobacteria; and Agrobacterium strains which cause production of agropine (for example, strain EHA105, EHA101, A281) are referred to as "agropine-type" Agrobacteria.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgene" refers to a foreign gene that is placed into an organism by the process of transfection. The term "foreign gene" refers to any nucleic acid (for example, gene sequence) that is introduced into the genome of an organism by experimental manipulations and may include gene sequences found in that organism so long as the introduced gene does not reside in the same location as does the naturally-occurring gene.

The term "transgenic" when used in reference to a cell or organism (in other words, a "transgenic cell" or "transgenic organism") refers to a cell or organism that contains at least one heterologous or foreign gene in it or in one or more of the cells of the organism. The term "transgenic" when used in reference to a plant or fruit or seed (in other words, a "transgenic plant" or "transgenic fruit" or a "transgenic seed") refers to a plant or fruit or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "host cell" refers to any cell capable of replicating and/or transcribing and/or translating a heterologous gene. Thus, a "host cell" refers to any eukaryotic or prokaryotic cell (for example, bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (for example., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, β-glucuronidase (GUS), luciferase (See for example, deWet et al., Mol. Cell. Biol. 7:725 (1987) and U.S. Pat. Nos., 6,074,859; 5,976,796; 5,674,713; and 5,618,682; all of which are incorporated herein by reference), green fluorescent protein (for example, GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "wild-type" when made in reference to a nucleic acid sequence refers to a nucleic acid sequence which has the characteristics of the sequence isolated from a naturally occurring source. The term "wild-type" when made in reference to a gene product refers to a gene product which has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a nucleic acid sequence (such as a regulatory sequence or a sequence encoding a gene) or to a gene product refers, respectively, to a nucleic acid sequence or to a gene product which displays modifications in sequence and/or functional properties (in other words, altered characteristics) when compared to the wild-type gene or gene product. Modifications include additions or deletions of the units making up the nucleic acid sequence or gene product (a unit is, for example, a nucleotide), or substitutions of at least one of the units. It is noted that naturally-occurring mutants can be isolated; these are identified by the fact that they have altered characteristics when compared to the wild-type nucleic acid sequence or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target gene, in that the protein the target gene normally encodes is not produced or is produced at a lower level than in the absence of the antisense RNA transcripts.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern gel blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual* (Cold Spring Harbor Press, NY), pp 9.31-9.58).

The term "Northern blot analysis" and "Northern gel blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52).

The terms "Western blot analysis" and "Western gel blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (in other words, an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (in other words, the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and anti-sense strands (in other words, the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DESCRIPTION OF THE INVENTION

The present invention provides novel chemically inducible promoters and promoter systems, its modification for use in plants (or other types of cells, including animal cells), and its use in plants (and other organisms) to control gene expression, where the inducing chemical is non-toxic. An exemplary inducible promoter was isolated from *Aspergillus niger*. Specifically, the novel chemically inducible promoter and promoter system identified in *Aspergillus niger* is induced by benzoate and related compounds.

The following section describes the development of the invention, including the discovery of the benzoate-inducible fungal promoter and promoter system, modification of the fungal promoter system and use in construction of gene promoter systems, and use of the hybrid fungal/gene promoter systems to control gene expression and developmental phases. Although the design of the promoter system uses plants as an example, the promoter system can be incorporated into, for example, animal cell systems and other fungal systems that lack benzoate-activated promoters.

The resulting benzoate inducible fungal promoter and promoter system of the present invention is of general utility for controlling gene expression in response to benzoic acid. It is understood that the method of discovering the benzoate inducible promoter and promoter system, outlined above and described below in detail for *Aspergillus niger*, can be applied to discover additional chemically inducible promoters from *Aspergillus niger*, as well as to discover chemically inducible promoters, and in particular benzoate inducible promoters, from other fungi or other organisms (e.g. plants).

I. Benzoate-Inducible Promoter, Response Element, Hybrid Promoters, and Promoter System The present invention provides novel benzoate inducible promoters, promoter response elements, and promoter systems. In some embodiments, the present invention provides an isolated nucleic acid sequence of a benzoate inducible promoter region, where the promoter region is induced by the presence of benzoate and/or related chemicals. In particular embodiments, the present invention provides an isolated nucleic acid sequence of a benzoate inducible promoter region from a fungus; in further particular embodiments, the benzoate inducible promoter region is from *Aspergillus niger*. In other particular embodiments, the benzoate inducible promoter region is from a bphA gene; in further particular embodiments, the bphA gene is from *Aspergillus niger*. In further particular embodiments, the present invention provides an isolated nucleic acid sequence of a benzoate inducible promoter region comprising SEQ ID NO:6 (as shown in FIG. 1, where SEQ ID NO:6 is positions −531 to −1 of SEQ ID NO:1), and its functional equivalents. In yet other particular embodiments, the present invention provides an isolated nucleic acid sequence of a benzoate inducible promoter region comprising a 0.4 kb nucleic acid sequence fragment (SEQ ID NO:2) which is positions −199 to −521 of SEQ ID NO:1. In yet other particular embodiments, the present invention provides an isolated nucleic acid sequence of a benzoate inducible promoter region comprising BREF51 (which is the BRE-containing Fragment, 51 bp long, SEQ ID NO: 4, and which comprises positions −357 to −407 of SEQ ID NO:1). In yet other particular embodiments, the present invention provides an isolated nucleic acid sequence of a benzoate inducible promoter region comprising any nucleic acid sequence fragment of SEQ ID NO:6, which fragment is at least about 51 base pairs in length and also comprises SEQ ID NO:4. In yet other particular embodiments, the present invention provides an isolated nucleic acid sequence of a benzoate inducible promoter region comprising any nucleic acid sequence fragment of SEQ ID NO:6 which is at least about 20 base pairs in length and which also comprises at least one BRE (for example, BRE6, SEQ ID NO:5 or BRE9, SEQ ID NO:8 which has the sequence CATTAGTCA).

In other embodiments, the present invention provides an isolated nucleic acid sequence comprising SEQ ID NO:6 (as shown in FIG. 1, where SEQ ID NO:6 is positions −531 to −1 of SEQ ID NO:1). In some embodiments, the present invention provides an isolated nucleic acid sequence comprising BREF51 (which is the BRE-containing Fragment, 51 bp long, SEQ ID NO:4). In other embodiments, the present invention provides an isolated nucleic acid sequence of a benzoate response element (BRE6), which is the sequence of the 6 bp direct repeats of BREF51, with the sequence TAGTCA (SEQ ID NO:5). In other embodiments, the present invention provides an isolated nucleic acid sequence of a benzoate response element (BRE9), which is the sequence of a 9 nucleic acid sequence of the putative BRE9, with the sequence CATTAGTCA (SEQ ID NO:8). In other embodiments, several copies (e.g. 2-15) of BRE6 (SEQ ID NO:5) are incorporated into flanking sequences that provide suitable conformational and enhancement of promoter activity in a benzoate-specific manner.

The discovery of the promoter region, promoter, promoter response element, and fragments comprising the promoter response element is described below. Further refinement of EMSA showed that a 51-bp sequence within mini-fragment FR6, at positions −357 to −407 from the transcription start point, is a target-binding site of the protein(s). This sequence was then called BREF51 (highlighted in FIG. 1). A significant feature of this element is the presence of a pair of 6-bp direct repeats, with the sequence 5'TAGTCA3' (SEQ ID NO:5), which are located at the edges of the sequence. Direct repeats have been shown to constitute target-binding sites of several different kinds of transcription factors in a variety of species (Lee et al. (1995) Mol. Cell. Biol. 15: 4194-4207; Zelhof et al. (1995) Proc. Natl. Acad. Sci. USA 92: 10477-10481; Yin et al. (1997) Plant J. 12: 1179-1188; González-Pérez et al. (1999) J. Biol. Chem. 274: 2286-2290; Park et al. (1999) FEBS Letters 463: 133-138; Yu et at. (2000) J. Biol. Chem. 275: 24208-24214; Risoen et al. (2001) Mol. Gen. Genom. 265: 198-206). In most instances these factors bind the target site as homodimers, with the spacing between the repeats being essential for the proper binding and function.

To confirm that the protein(s) previously shown to interact with BREF51 do so by binding to one or more of the direct repeats, mutations were introduced on both repeated sequences, and these modified BREF51 were labeled and used on EMSA. FIG. 10 shows that sequence modifications of the first repeat (position −407) do not interfere with the in vitro binding of the protein factor(s). However, sequence modifications or complete substitution of the second TAGTCA (position −365 bp) repeat almost completely abolishes binding, as judged by the lack of mobility shift of the probe. Therefore, these results indicate that this (these) protein(s) is (are) binding specifically to the TAGTCA sequence located at −365 bp upstream of the transcription start point, within BREF51. However, since a faint mobility-shifted band was still observed when the modified probes were used, it is possible that sequences flanking the TAGTCA located at position −365 bp may also contribute to binding, or there is weak binding to the upstream TAGTCA. Of special interest is the presence of an almost perfect palindromic sequence (boxed in FIG. 10) positioned between the direct repeats. As shown in FIG. 10, the TGA sequence located just downstream from the second TAGTCA (position −365) does not seem to be important for this interaction. The promoter region of the bzuA gene from *A. nidulans* also contains a TAGTCA sequence, which is located −568 to −573 bp upstream from the transcription start point. However, this sequence neither appears to be duplicated in the promoter of that gene, nor does it contain a similar palindrome nearby the TAGTCA sequence.

These modified BREF51 sequences (or other candidate BREs) can be introduced upstream of a "minimal promoter" (−331 to +1), and fused to the GFP gene to further test these constructs. These constructs may be transformed into *A. nidulans*, and GFP expression scored in the presence and absence of benzoic acid.

In other embodiments, the present invention provides nucleic acid sequences that hybridize to a benzoate inducible promoter region (for example, SEQ ID NO:6), to a response element (for example, SEQ ID NO:4 or SEQ ID NO:5), or to fragment comprising a benzoate response element (for example, SEQ ID NO:3), any and all as described above. In further embodiments, these sequences are functionally equivalent to benzoate inducible promoter, to a response element, or to a fragment comprising the benzoate response element, any and all as described above. By functional equivalence, it is meant that these nucleic acid sequences are capable of induction by benzoate and/or related chemicals either by themselves, or when incorporated into a hybrid promoter (as described further below), and when operably linked to a gene of interest. Such sequences of the present invention are characterized for functional equivalence using the methods described below. In other words, the protocols and examples below may be used to test any of the sequences found to hybridize to the sequences described above to determine if they will function as benzoate response elements (e.g. in combination with a gene promoter).

In other embodiments, the present invention provides nucleic acid sequences of benzoate inducible promoters, response elements, and promoter fragments comprising response elements, which sequences are naturally located upstream to structural DNA sequences which are identified as genes naturally under control of a homologous benzoate inducible promoter as described above, where any of the naturally occurring nucleic acid sequences are functionally equivalent to the benzoate inducible promoters, response elements, and promoter fragments comprising response elements as described above.

In other embodiments, the present invention provides a novel benzoate inducible hybrid promoter, where the hybrid promoter comprises at least one copy of any nucleic acid sequence fragment of SEQ ID NO:6, which fragment is at least about 20, about 30 or about 51 base pairs in length and also comprises SEQ ID NO:5, and a heterologous gene promoter region, such that the hybrid promoter is responsive to benzoate and/or related chemical inducers. In particular embodiments, the nucleic acid sequence fragment of SEQ ID NO:6 is BREF51 (SEQ ID NO:4) or any other fragment that contains BRE6 (SEQ ID NO:5) and is at least 15 or at least 20 bases in length. In other embodiments, the present invention provides a novel benzoate inducible hybrid promoter, where the hybrid promoter comprises at least one copy of any nucleic acid sequence fragment of SEQ ID NO:6, which fragment comprises at least one copy of a BRE (for example, BRE6, SEQ ID NO:5, or BRE9, SEQ ID NO:8), and a heterologous gene promoter region, such that the hybrid promoter is responsive to benzoate and/or related chemical inducers (e.g. benzoate mimetics, which may be found using the protocols described in the examples below by substituting a candidate mimentic for benzoate). In other embodiments, the present invention provides a novel benzoate inducible hybrid promoter, where the hybrid promoter comprises at least one copy of a BRE (for example, BRE6, SEQ ID NO:5, or BRE9, SEQ ID NO:8) and a heterologous gene promoter region, such that the hybrid promoter is responsive to benzoate and/or related chemical inducers. In any of these embodiments, the heterologous gene regulatory region may further comprise minimal gene promoter regions and/or elements. In particular embodiments, a minimal plant promoter comprises a TATA box for RNA polymerase recognition but no other elements that give cell or tissue specificity. The BREs in these hybrid promoters are believed to be bound by protein factors, which are encoded by constitutively expressed transcriptional factor genes, and which modulate promoter activity in the presence of benzoate and/or related chemical inducers. As described below, optimization of hybrid promoter constructs involves determining the minimal fragments comprising at least one BRE necessary and sufficient to control gene expression. In some embodiments, tandem arrays of BREF51 are linked to minimal promoter regions sufficient to create (BREF51)$_n$-minimal promoters that are utilized in host cell systems; in some further embodiments, the minimal promoter region is a plant minimal promoter region, and the hybrid promoter is utilized in plant systems. Gene regulatory regions are derived from eukaryotic or prokaryotic cells; eukaryotic cells are plant or animal cells. Such novel benzoate inducible hybrid promoters of the present invention are characterized for functional equivalence using the methods described below.

In other embodiments, the present invention provides a novel benzoate inducible promoter system, which comprises a promoter component and at least one transacting factor component. The promoter component comprises any of the benzoate inducible promoters of the present invention described above. The transacting factor component comprises a coding region for a transacting factor that is necessary and sufficient for the induction of the promoter component by benzoate and/or related chemicals; in some embodiments, the transacting factor is a transcription factor. In some embodiments, the at least one additional gene encoding a transacting factor is under control of a promoter; in some embodiments, the promoter is a constitutive promoter. In some embodiments, the benzoate promoter system is present in at least one expression vector, where the expression vector(s) can be used to transfect a host cell, either transiently or stably. Discovery of transcription factor components, and further description of these components, is provided below.

Briefly, the yeast one-hybrid system works by construction of a library of many thousands of clones of potential transcription factors in yeast clones in which three tandem copies of BREF51 (SEQ ID NO:4) driving a gene that would enable the yeast to grow on media lacking the amino acid His. The yeast one-hybrid system screen yielded 17 colonies on SD/-Leu/-His media after 4 days of incubation. These 17 clones were streaked on SD/-Leu/-His media to confirm the ability of the cells to grow in the absence of the two amino acids. Plasmid DNA obtained from all the clones was used as a template for PCR reactions with the purpose of determining the size of the cDNA inserts. The inserts varied in size from 0.5 to 1.4 kbp. Some clones contained more than one insert. Plasmid DNA from the positive clones was transformed into E. coli XL1-Blue cells with the objective of obtaining greater amounts of DNA for sequencing, as well as to be able to separate distinct plasmids contained within the same yeast strain. Plasmid DNA was prepared from the bacterial clones and used as template for a new round of PCR. The results from these reactions confirmed that some of the original yeast clones indeed contained two distinct plasmids (data not shown). In contrast to E. coli, yeast cells are able to maintain and replicate more than one plasmid inside the cell. DNA sequences obtained from the plasmids isolated from the bacterial cells were translated and compared by BLASTp search (Altschul et al. (1997) Nucl. Acids Res. 25: 3389-3402) to the GenBank database (Table 1).

TABLE 1

Sequence similarity of GAD clones to available databases (BLASTp search).

| CLONE ID | INSERT SIZE | SIMILARITY | SCORE (bits) | E VALUE |
|---|---|---|---|---|
| GAD 1.1 | 1.2 kbp | Hypothetical prot. N. crassa, | 115 | $7e^{-25}$ |
|  |  | serine-rich prot. S. pombe | 82 | $1e^{-14}$ |
| GAD 2 |  | NO INSERT |  |  |
| GAD 3.1 | 1.2 kbp | Pepsinogen A. niger | 583 | $e^{-165}$ |
| GAD 3.2 | 1.3 kbp | Hypothetical prot. N. crassa | 243 | $2e^{-19}$ |
| GAD 4.1 | 1.0 kbp | hypothetical prot. N. crassa, | 104 | $2e^{-21}$ |
|  |  | CipC protein A. nidulans | 77 | $5e^{-13}$ |
| GAD 4.2 | 0.6 kbp | No significant similarities | — | — |
| GAD 5.1 | 1.2 kbp | hypothetical prot. N. crassa, | 104 | $2e^{-21}$ |
|  |  | CipC protein A. nidulans | 77 | $5e^{-13}$ |
| GAD 6.1 | 1.1 kbp | Isopentenyl diphosphate isomerase A. nidulans | 103 | $4e^{-21}$ |
| GAD 6.2 | 0.8 kbp | 60s ribosomal protein S. pombe | 215 | $7e^{-55}$ |
| GAD 7.1 | 0.7 kbp | No significant similarities | — | — |
| GAD 8.1 | 0.6 kbp | Predicted prot. N. crassa | 68 | $2e^{-10}$ |
| GAD 9.1 | 0.5 kbp | No significant similarities | — | — |
| GAD 10.1 | 0.8 kbp | Hypothetical prot. N. crassa, putative | 171 | $1e^{-41}$ |
|  |  | bacterial flavohemoprotein | 161 | $1e^{-38}$ |
| GAD 11.1 | 1.0 kbp | No significant similarities | — | — |
| GAD 12.3 | 1.0 kbp | Triose phosphate isomerase A. niger | 429 | $e^{-119}$ |
| GAD 12.4 | 1.2 kbp | Outer mitochondrial membrane prot. porin N. crassa, yeast | 374 | $e^{-105}$ |
| GAD 13.1 | 0.6 kbp | No significant similarities | — | — |
| GAD 14.1 | 0.5 kbp | No significant similarities | — | — |
| GAD 15 |  | NO INSERT |  |  |

TABLE 1-continued

Sequence similarity of GAD clones to available databases (BLASTp search).

| CLONE ID | INSERT SIZE | SIMILARITY | SCORE (bits) | E VALUE |
|---|---|---|---|---|
| GAD 16.1 | 0.6 kbp | Hypothetical prot. B17C10.140 N. crassa | 93 | $6e^{-18}$ |
| GAD 16.3 | 1.3 kbp | Hypothetical prot. N. crassa, | 105 | $1e^{-21}$ |
|  |  | Hypothetical prot. S. pombe | 103 | $3e^{-21}$ |
| GAD 17.1 | 1.2 kbp | Heat shock prot. 70 A. nidulans | 457 | $e^{-127}$ |

Some clones, such as GAD3.1, GAD12.3, GAD12.4, and GAD17.1 constituted false positives, in the sense that the proteins had very high similarity to fungal proteins which functions are known not to be involved with transcriptional regulation. However, most of the cDNAs encoded proteins whose functions are not yet known. These are mostly hypothetical proteins predicted from computer algorithms, and generated during data mining of complete genome sequencing projects.

Translated sequences of potential candidates for proteins that interact with BREF51 were also compared to completed genome sequences of Aspergillus nidulans (Release 1) and Neurospora crassa (Release 3) (tBLASTn search, Whitehead Institute) (Table 2), since both of these species contain a gene with high similarity to the bphA gene from A. niger.

TABLE 2

Comparison of selected GAD sequences to A. nidulans and N. crassa completed genome sequences (tBLASTn search).

| CLONE ID | SIMILARITY TO A. nidulans | SCORE (E value) | SIMILARITY TO N. crassa | SCORE (E value) |
|---|---|---|---|---|
| GAD 1.1 | Contig 1.64 | 306 ($2e^{-83}$) | Contig 3.74 | 119 ($4e^{-27}$) |
| GAD 3.2 | Contig 1.14 | 359 ($2e^{-99}$) | Contig 3.190 | 94 ($3e^{-19}$) |
| GAD 4.1 | No hits | — | No hits | — |
| GAD 4.2 | Contig 1.51 | 70 ($1e^{-12}$) | No hits | — |
| GAD 5.1 | No hits | — | No hits | — |
| GAD 7.1 | No hits | — | No hits | — |
| GAD 8.1 | No hits | — | No hits | — |
| GAD 9.1 | No hits | — | No hits | — |
| GAD 10.1 | Contig 1.122 | 256 ($1e^{-68}$) | Contig 3.94 | 167 ($6e^{-42}$) |
| GAD 11.1 | Contig 1.69 | 124 ($6e^{-29}$) | No hits | — |
| GAD 13.1 | No hits | — | No hits | — |
| GAD 14.1 | Contig 1.105 | 144 ($2e^{-35}$) | No hits | — |
| GAD 16.1 | Contig 1.174 | 86 ($1e^{-17}$) | Contig 3.75 | 67 ($7e^{-12}$) |
| GAD 16.3 | Contig 1.19 | 147 ($6e^{-36}$) | Contig 3.210 | 105 ($6e^{-23}$) |

As demonstrated by RNA blots, the A. nidulans homolog bzuA is also upregulated in the presence of benzoic acid in the media, and despite showing a different pattern of expression, it is likely that A. nidulans contains a similar machinery to control bzuA activity. On the other hand, while N. crassa also contains a bphA homolog, there is no current information available as to its response to benzoic acid.

Total proteins were isolated from 9 yeast clones which cDNAs encoded proteins that did not show significant similarities to any gene of known function in the databases. Protein extracts from each of these yeast clones were used in EMSA to eliminate those cDNAs that encode proteins that do not interact with BREF51. Yeast clones GAD1 (amino acid sequence shown in SEQ ID NO:15; and nucleic acid sequence shown in SEQ ID NO:16) and GAD11 (amino acid sequence shown in SEQ ID NO:17; and nucleic acid sequence shown in SEQ ID NO:18), which contained only one cDNA each, as judged by PCR data, both showed a gel mobility shift of the BREF51 fragment in these assays (FIG. 13). The shift in mobility displayed by GAD1 was similar to that observed with *A. niger* total protein extracts. The protein encoded by GAD1 (SEQ ID NO:15) is highly similar to a predicted protein present in the *A. nidulans* genome (E value $2e^{-83}$), and similar to a hypothetical protein (B24P11.210) in the *N. crassa* genome (E value $4e^{-27}$) (Table 2). GAD1 protein is rich in serine residues (16%), and is predicted by PSORTII (Nakai and Horton (1999) Trends Biochem. Sci. 24: 34-35) to be localized in the nucleus (70.6% probability). It also shows high similarity to a hypothetical serine-rich protein (C13G6.10c) from *S. pombe*. Serine-rich motifs can be phosphorylation targets by protein kinase C in proteins (Branden and Tooze (1999) Introduction to protein structure, $2^{nd}$ ed. Garland Publishing, New York, N.Y. 410 p.). Also, serine-rich regions have been shown to be part of the transactivation domains of some transcription factors in both mammalian and viral cells (Wetering et al. (1993) EMBO. J. 12: 3847-3854; Ma and Staudt, (1996) Blood 15: 734-745; Chen et al. (1999) Mol. Cell. Biol. 19: 307-316; Bowles et al. (2000) J. Virol. 74: 1200-1208). While not necessary to understand in order to practice the present invention, if GAD1 is involved in the regulation of BPHprom, GAD1 protein might be always bound to a benzoic acid response element in the bphA promoter. In the absence of benzoic acid GAD1 would be inactive, unable to promote transcription. However, addition of benzoic acid could cause phosphorylation of one of the serine residues in GAD1, leading to its activation. This mode of regulation is analogous to that of the transcription factor CREB, which is involved in responses to cAMP in human cells (Latchman (1997) Intl. J. Biochem. Cell Biol. 29: 1305-1312).

GAD11 protein (SEQ ID NO: 17) is weakly similar to a *Drosophila melanogaster* homeotic gene regulator, and also to a putative nuclear protein family member from the nematode *C. elegans*. It is also predicted by PSORTII (Nakai and Horton (1999) Trends Biochem. Sci. 24: 34-35) to be localized in the nucleus (94.1% probability). GAD11 was also predicted to have a coiled-coil region consisting of 37 amino acid residues (Lupa's algorithm). The α-helical coiled coil is a structural motif found in many proteins. It consists of two long α-helices with a repeating pattern of hydrophobic side chains that interlock to produce a supercoiled structure. The most important function of coiled-coil regions in myosins and kinesins is for dimerization. Because the coiled coil may be rigid and extended in solution it can act as a spacer or connector between protein domains (Branden and Tooze (1999) Introduction to protein structure, $2^{nd}$ ed. Garland Publishing, New York, N.Y. 410 p.). While not necessary to understand to practice the present invention, this may explain the larger shift in BREF51 mobility in the presence of GAD11 protein extract, since GAD11 proteins may be forming homodimers connected by the coiled-coil region. GAD11 has a homolog in *A. nidulans* (E value $6e^{-29}$), but no homologs in *N. crassa* were found. Although 5 μg of total yeast protein extracts were used on EMSA, the gel mobility shifts observed on the yeast clones were less intense than those obtained with the positive control, where only 1 μg of total protein extract from *A. niger* cells was used. According to the plasmid manufacturer (Clontech), cDNAs cloned into this activation domain vector show low expression levels, which may explain the lower intensity of the shifted bands even in the presence of a higher amount of total proteins.

Reverse Transcription PCR (RT-PCR) experiments revealed that while GAD1 is expressed constitutively, GAD11 is slightly downregulated in the presence of 8 mM benzoic acid for 5 h (FIG. 14). While not necessary to understand to practice the present invention, if in fact either GAD1 or GAD11 are involved in regulation of the bphA promoter, constitutive transcription of GAD1 does not rule out the possibility that the activity of the GAD1 protein is modulated by benzoic acid. On the other hand, downregulation of the GAD11 gene in the presence of benzoic acid indicates that the protein may function as a transcriptional repressor of the bphA promoter. GAD1 is constitutively expressed, while GAD11 seems to be downregulated in the presence of benzoic acid in the media. There is a possibility that protein-protein interactions play a role in the regulation of this gene in *A. niger*. To clarify the role of GAD1 and GAD11, one could create deletion mutations of each gene (GAD1 and GAD11) in *A. niger*. Deletion of the true transcription factor that controls activity of BPHprom should result in a lack of bphA expression in the presence of benzoic acid. Alternatively, deletion mutants of the GAD1 and GAD11 homologs from *A. nidulans* strains containing the pBPH-1847-GFP constructs could be prepared, and GFP expression in the presence of benzoic acid is scored.

Benzoate inducible means that the promoter is inducible by benzoate and/or related chemicals. Benzoate and/or related chemicals include but are not limited to benzoic acid and its salts ($Na^+$, $K^+$, $NH_4^+$, etc.), and esterified forms of benzoic acid. The esterified forms of benzoic facilitate penetration of the esterified forms into cells, and once inside the cells, the esterified forms are subsequently be de-esterified by the cell's own esterases to yield active compound. Thus, related chemicals include but are not limited to sodium benzoate and methyl benzoate. It is contemplated that features necessary and sufficient for activity are a benzyl ring with one carboxyl group. It is contemplated that derivatives with substitutions at the ortho- (e.g., 2-hydroxy-benzoate, or salicylate) and meta-positions of the ring reduce or abolish effectiveness of the benzoic acid derivative as an inducer, whereas substitutions at the para-position, such as para-aminobenzoate, are generally more effective.

Discovery of the benzoate inducible promoter and promoter response element involved several steps. These included identifying a gene which is induced by benzoic acid, characterizing induction of expression, isolating the promoter region, determining which fragments of the promoter region comprise a benzoate response element, and identifying additional components of the benzoate inducible promoter system, such as transacting factors, where such transacting factors include but are not limited to transcription factors. Modification of the benzoate inducible promoter system includes but is not limited to incorporating the benzoate response elements into a gene promoter or regulatory region to create a benzoate inducible hybrid promoter, and in particular into a gene minimal promoter or regulatory region. Utilization of the benzoate promoter system includes but is not limited to transforming cells with the benzoate inducible hybrid promoter; in some embodiments, utilization further includes the additional transformation of cells with at least one gene encoding an additional factor which allows the benzoate inducible hybrid promoter to function in the transgenic cell and be inducible by benzoate and/or related chemicals; such factors include transcription factors. The greater the disparity between the source of the benzoate inducible promoter and the host cell (such as a fungus and a plant, respectively), the greater the likely disparity between inducible factors between the two types of cells. Thus, it is contemplated that a greater specificity of the inducible factors is obtained in an inter-Kingdom combinatorial system, which means that the source inducing factors are less likely are to induce endogenous genes in the host cell.

A. Discovery of Benzoate-Inducible Promoter and Promoter Response Element

As reviewed by Gatz et al. ((1997) Ann. Rev. Plant Physiol. Plant Mol. Biol. 48: 89-108) and Gatz and Lenk ((1998) Trends Plant Sci. 3: 352-358.), an ideal chemically inducible expression system would possess all of the following features: a) expression levels should be very low or none in the absence of the chemical stimulus; b) expression levels should increase rapidly to high levels upon application of the inducer; c) the chemical stimulus should be non-toxic to the plant and all other organisms in the plant's ecosystem; d) the chemical stimulus should not exhibit pleiotropic effects in treated plants; e) the chemical stimulus should be easily applied in the field and in the greenhouse by spraying, or under tissue culture conditions by adding it to a synthetic medium; f) depending on the nature of the application, different derivatives of the inducer should be available and induction should be effective at low rates of application; g) a second compound should be available that abrogates the induction so that both positive and negative control are possible; h) a chemically inducible system should also be amenable to be combined with tissue-specific expression.

Several examples of chemical control of gene expression in plants exist today, but none meets all of the requirements described above. These examples include synthetic promoter systems that can be induced by tetracycline (Gossen and Bujard (1992) Proc. Natl. Acad. Sci. USA 89: 5547-5551; Shockett and Schatz (1996) Proc. Natl. Acad. Sci. USA 93, 5173-5176), steroid compounds (Aoyama and Chua (1997) Plant J. 11: 605-612; Kunkel et al. (1999) Nature Biotech. 17: 916-919), copper ions (Mett et al. (1993) Proc. Natl. Acad. Sci. USA 90: 4567-4571), ethanol (Caddick et al. (1998) Nature Biotech. 16: 177-180; Salter et al. (1998) Plant J. 16: 127-132), herbicide safeners (De Veylder et al. (1997) Plant Cell Physiol. 38: 568-577), and insect ecdysone agonists (Jepson et al. (1998) Pestic. Sci. 54: 360-367). Each system has its own disadvantages, but all share a major disadvantage of the high level of toxicity of the inducers, especially if the inducers were to be used on field crops. For example, growth defects have been reported in transgenic *Arabidopsis* plants containing the glucocorticoid-inducible transcription system (Kang et al. (1999) Plant J. 20: 127-133). Other disadvantages are encountered using as chemical inducers chemicals endogenously produced by the host system. As an example, plants make ethanol under oxygen stress, for example under flooding stress, so use of the ethanol promoter in agronomic settings has severe disadvantages with respect to tightness of control. Thus, there are inherent advantages to the use of a chemical not produced by the host organism in which the novel system has been placed.

The use of transcriptional activators and their corresponding response elements from fungal systems is attractive because of the reduced risk of interference between the switch system and the endogenous host-plant transcriptional machinery (Jepson et al. (1998) Pestic. Sci. 54: 360-367). Thus, for example, if the construction of a chemically inducible promoter is based on a plant gene, then application of the chemical inducer would also cause induction of the endogenous plant gene. The disparity between fungal and plant systems suggests that fungal effectors would not be found in the plants, and thus employing fungal effectors minimizes any possible interference. One example is the ethanol-controllable system mentioned above; this system is based upon the Alc regulon from the fungus *Aspergillus nidulans* (Eidam) Winter, which controls its response to ethanol and other related chemicals. This system has been only recently developed (Caddick et al. (1998) Nature Biotech. 16: 177-180), and, although it seems initially promising, questions concerning the specificity of the inducer for the transgene, toxicity, background levels, and induction levels over a longer time course have yet to be addressed (Gatz and Lenk (1998) Trends Plant Sci. 3: 352-358). Therefore, other fungal promoters may be more suitable, or offer other advantages.

The fungus *Aspergillus niger* appeared to be a likely source of a suitable promoter system based upon the following observations. *Aspergillus niger* is able to grow in a culture medium that contains only benzoic acid as a carbon source, as reported in 1985 by Sahasrabudhe and Modi ((1985) Biochem. Intl. 10: 525-529). The isolation and cloning of the gene that encodes the enzyme benzoate para-hydroxylase (BPH) from *Aspergillus niger* (BphA gene; GenBank X52521) was reported in 1990 by van Gorcom et al. ((1990) Mol. Gen. Genet. 223, 192-197). BPH catalyzes the first of a series of steps by which *A. niger* catabolizes benzoic acid; this first step involves the hydroxylation of the aromatic ring at the para position. The enzyme belongs to the class of cytochrome P450 monooxygenases (CYP53A1; van den Brink et al. (1998) Fungal Genet. Biol. 23, 1-17) and was first purified by Reddy and Vaidyanathan (1975) Biophys. Acta 384: 46-57). The BPH enzyme is not present in the fungal mycelia if benzoate is not added to the culture medium, and its synthesis seems to be transcriptionally induced upon transfer of the fungal cells to benzoate-containing media (van Gorcom et al. (1990) Mol. Gen. Genet. 223: 192-197). Hence, this gene appeared to be a good candidate for gene induction at the transcriptional level by an innocuous chemical substance.

1. Identification of the Promoter

Figure 2:
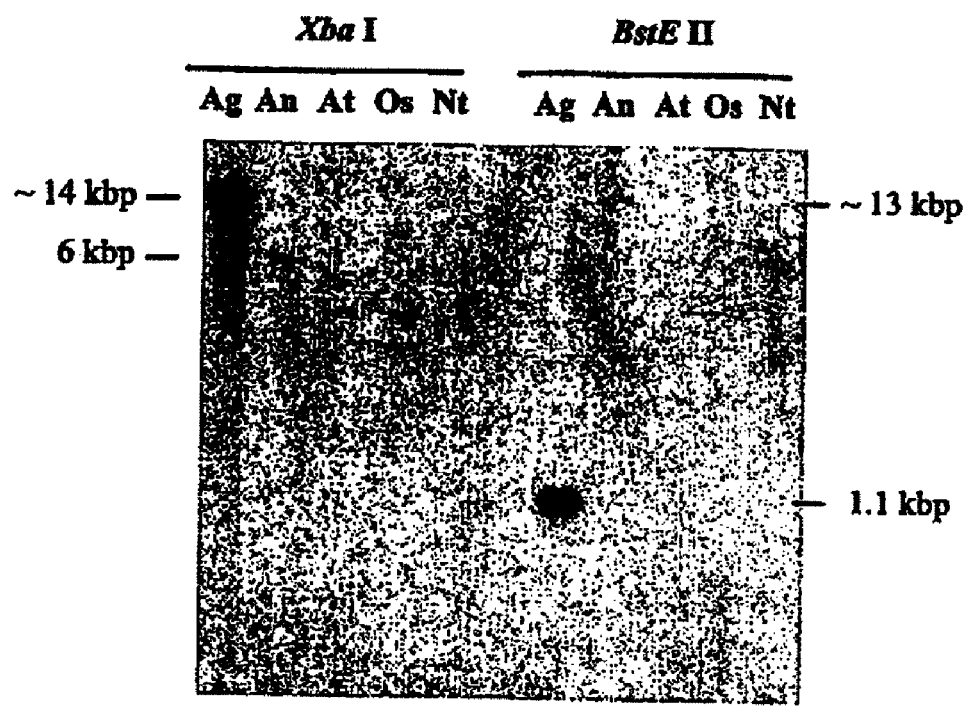
FIG. 2 shows a genomic DNA blot, where genomic DNA from plant or fungal sources is probed with α-$^{32}$P-dCTP-labeled BPH probe, and shows an absence of bphA homologs from plant species. Restriction of genomic DNAs from *A. niger* and *A. nidulans* with Xba I gives single bands of 12 kb and 10 kb, respectively. Restriction of the DNAs with BstE II gives bands at 1.1 kb and 12 kb, respectively. Lanes: Ag, *Aspergillus niger*; An, *Aspergillus nidulans*; At, *Arabidopsis thaliana*; Os, *Oryza sativa*; Nt, *Nicotiana tabacum*.
Figure 3:
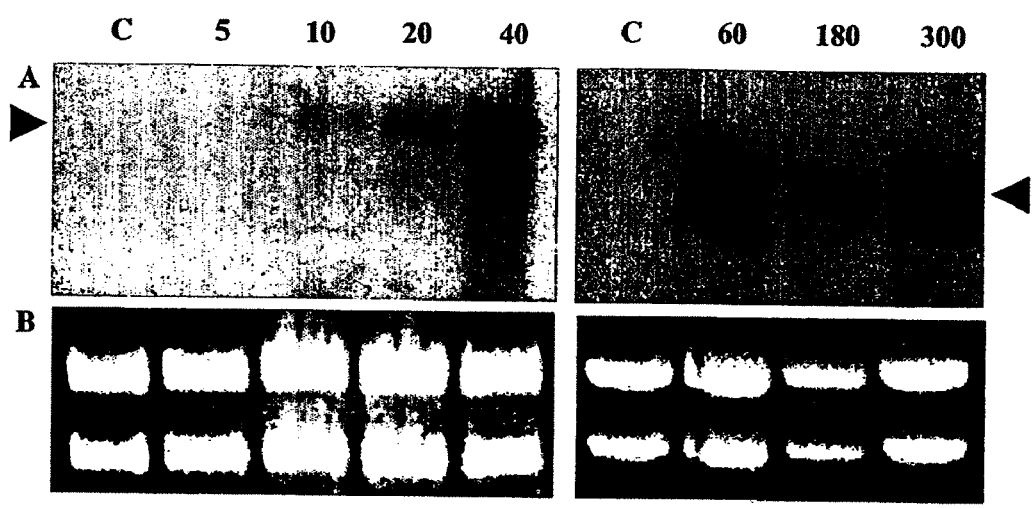
FIG. 3 shows a time course of bphA induction in the presence of 8 mM benzoic acid. Total RNA was electrophoresed on a formaldehyde-agarose gel, blotted onto Hybond-N membrane, and probed with the 32P-labeled BPH probe. Lanes, C, control, non-induced; numbers refer to minutes of incubation in the presence of benzoic acid before total RNA extraction. *A. Autoradiogram* of membrane; *B. Ethidium* bromide-stained total RNA gel is a loading control. Arrowheads point to 2.1 kbp-size band corresponding to the bphA message. The RNA was probed with α-$^{32}$P-dCTP-labeled BPH probe. Lanes: Cont is a non-induced control taken at time 0, whereas 5, 10, 20, and 40 are times in minutes after addition of 8 mM benzoic acid. Shown as a loading control is an ethidium bromide-stained total RNA gel (panel B).
Figure 4:
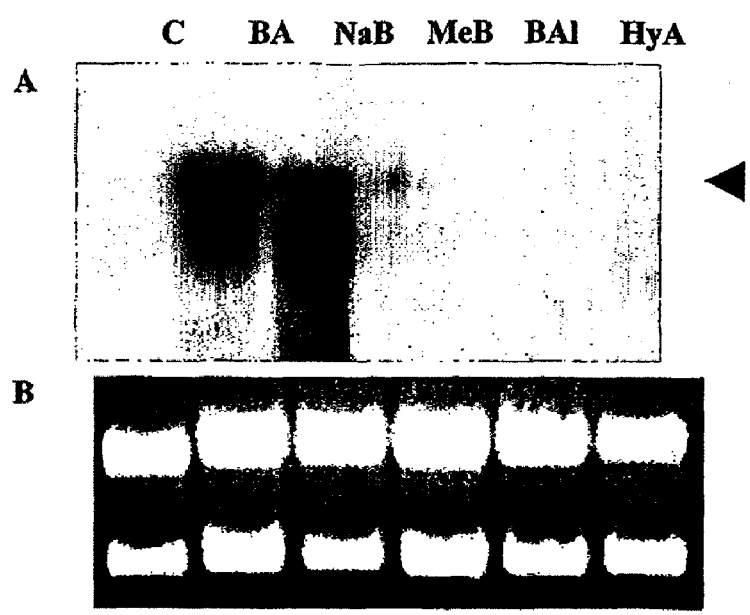
FIG. 4 shows RNA blots of transcription of the bphA gene in response to different chemical inducers. The results show that transcription of the bphA gene is induced by 8 mM benzoic acid, as well as by sodium benzoate and methyl benzoate at the same concentration. Benzyl alcohol and hydrocinnamic acid are not effective inducers of the bphA gene at 8 mM concentration. Top panel: RNA blot, probed with the $^{32}$P-labeled BPH probe (arrowhead points to 2.1 kbp-size band corresponding to the bphA message); Bottom panel: EtBr-stained gel, as a loading control. Lanes: C, control, uninduced; BA, benzoic acid; NaB, sodium benzoate; MeB, methyl benzoate; BAlc, benzyl alcohol; HyAc, hydrocinnamic acid.

Investigation of the distribution of the gene encoding the enzyme benzoate para-hydroxylase (BPH) in plants and fungi demonstrated that the bphA gene is found only in fungi (FIG. 2). Investigation of the time of gene induction indicated that the bphA gene is induced by benzoic acid after only ten minutes of exposure to the chemical (FIG. 3). The pattern of expression of the bphA gene from *A. niger* was investigated with a series of RNA blots; the results indicate that the bphA gene promoter is quickly induced within 10 minutes after incubation of the mycelia in media containing 8 mM benzoic acid (FIG. 3). Concentration curves indicate that benzoic acid concentrations as low as 0.8 mM induce transcription of the bphA gene. Other compounds which can induce the promoter include sodium benzoate and methyl benzoate; however, benzyl alcohol and hydrocinnamic acid do not induce the promoter (FIG. 4). In all of these RNA blot experiments, it was observed that the BPH message is not present until benzoate is added to the culture medium. Therefore, it is contemplated that this gene might provide some strict regulatory mechanisms for control of gene expression.

Using Anchored Polymerase Chain Reactions (PCR) as described by (Siebert et al. (1995) Nucl. Acids Res. 23: 1087-1088), about 1.8 kb of the promoter region of the *Aspergillus niger* bphA gene was isolated, and then cloned into pBluescript SK⁻. This region was subsequently sequenced by an automated di-deoxy chain termination method (Sanger et al. (1977) Proc. Natl. Acad. Sci. USA 74 5463-5467) at a commercial national service center; the sequence is shown in FIG. 1.

2. Identification of the Benzoate Response Element

Figure 5:
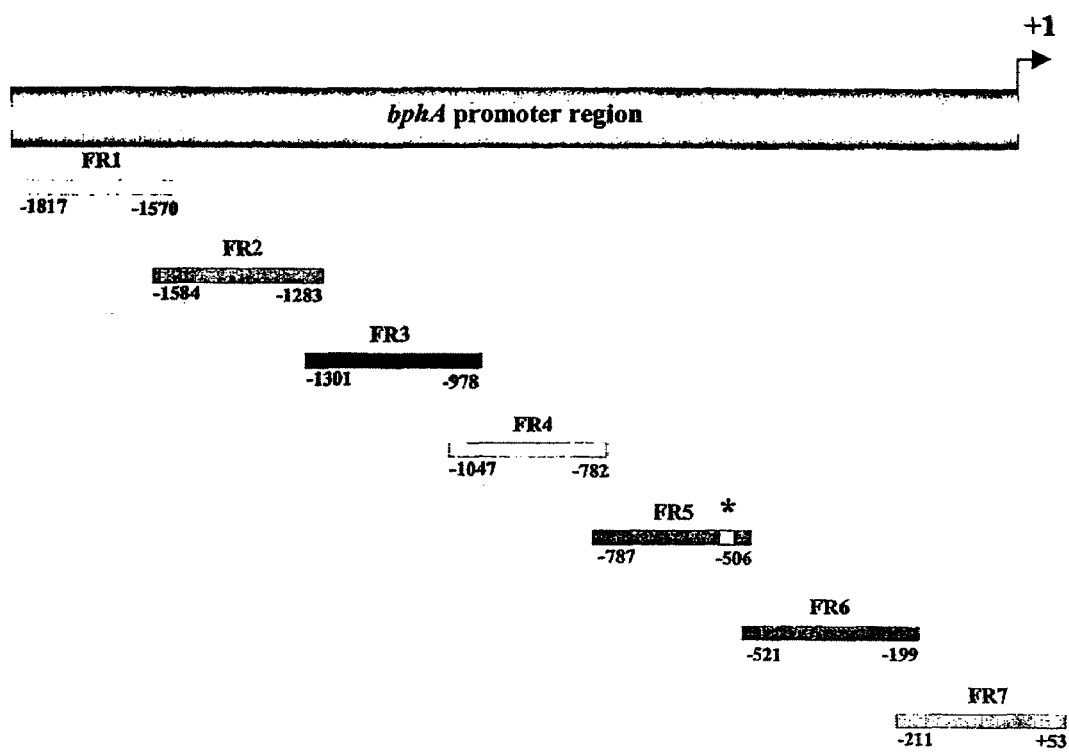
FIG. 5 shows mini-promoter fragments from the upstream region of the bphA gene examined for protein binding. Seven mini-promoter fragments (FR1-FR7) were prepared by PCR, and labeled with $^{32}$P-dATP and T4 Polynucleotide kinase for Electrophoretic Mobility Shift Assays. Numbers refer to position of base pair in relation to transcription start point (+1). FR1 to FR7 refer to mini-fragments 1 to 7, respectively. The * in this figure indicates the localization of the proposed Benzoic Acid Response Element by van den Brink et al. (2000).
Figure 6:
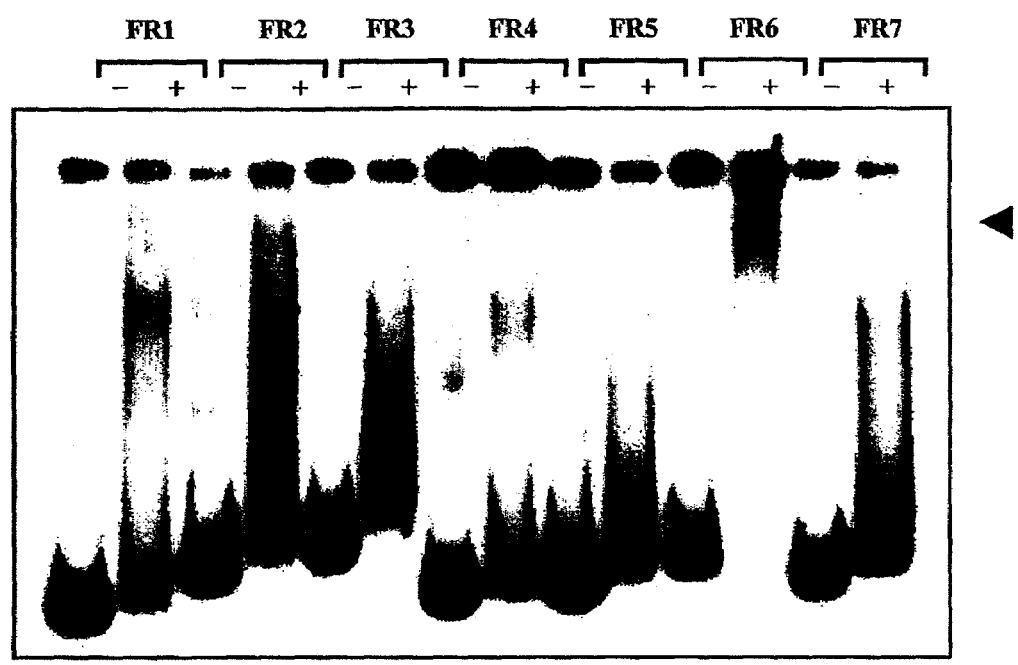
FIG. 6 shows results of protein binding to the mini-promoter fragments shown in FIG. 5. Electrophoretic mobility shift assay with four 260 to 330 bp fragments of the 1.8 kb putative promoter region was performed in the presence (+) and absence (−) of protein. Total protein (cytoplasmic and nuclear) of *Aspergillus* cells were incubated with $^{32}$P-labeled fragments for 1 h, and the mixtures then separated by polyacrylamide gel electrophoresis. Positive binding of a cytosolic protein is indicated when the electrophoretic mobility of a portion of the DNA fragment is slowed significantly. Fragment 6, is the only fragment to bind potential transcription factors. The arrowhead points to the mobility-shifted band from FR6. It is noted that FR5 (not FR6) contains the Benzoic Acid Response Element originally proposed by Van den Brink et al. (2000).
Figure 7:
FIG. 7 shows the results of Electrophoretic Mobility Shift Assays (EMSA) which identified a 51-bp fragment containing a Benzoate Response Element (BRE). This fragment consistently binds a factor present in a total protein extract from benzoate-induced *A. niger* mycelia. The arrow points to the mobility-shifted band. Lanes: 1, $^{32}$P-labeled BRE; 2, $^{32}$P-labeled BRE+total protein extract from benzoate-induced *A. niger* 3, same as in 2+excess of "cold" BRE; 4, same as in 2+"cold" DNA fragment from promoter region of unrelated gene.

In order to investigate whether protein factors are involved in controlling the initiation of transcription from the bphA gene promoter, seven mini-promoter fragments were created by PCR (FIG. 5), ranging in size from 247 bp to 324 bp. These fragments were then radio-labeled with $^{32}$P-dATP, and used in Electrophoretic Mobility-Shift Assays (EMSA). After confirming that one of these fragments (FR6, 323 bp) was bound by protein factors (FIG. 6), partially overlapping sub-fragments encompassing the FR6 fragment were prepared, and again used in EMSA. These assays showed that a 51-bp fragment located 350 bp upstream of the transcription start point is consistently bound by a protein factor that is present in total protein extracts from benzoate-induced *A. niger* mycelia (FIG. 7). The most significant feature of the sequence of this 51 bp fragment (shown in FIG. 8) is the presence of a pair of 6-bp direct repeats (underlined in FIG. 8). Short direct repeats have been shown to constitute cis-acting promoter elements affecting transcription of many genes (Lee et al. (1995) Mol. Cell. Biol. 15: 4194-4207; Zelhof et al. (1995) Proc. Natl. Acad. Sci. USA 92: 10477-10481; Yin et al. (1997) Plant J. 12: 1179-1188; González-Pérez et al. (1999) J. Biol. Chem. 274: 2286-2290; Park et al. (1999) FEBS Lett. 463: 133-138; Yu et al. (2000) J. Biol. Chem. 275: 24208-24214; and Risoen et al. (2001) Mol. Gen. Genom. 265: 198-206). These repeats are usually bound by transcription factors that form dimers when in the active form. Therefore, the number of nucleotide bases between the direct repeats is often critical for achieving binding of the protein factor. However, as discussed above, the functioning BRE may comprise only one of the repeats. In fact, it was found that all or most of the activity was retained by employing only one of the BRE6 repeats. The single consensus element found in the bphA promoters of *A. niger, A. nidulans,* and *N. crassa* is TAGTCA (SEQ ID NO:5). It is contemplated that, in some embodiments, nucleotide bases flanking this putative element are included for complete binding of a transcription factor.

When mutations were introduced on both repeated sequences, and these modified BREF51 were labeled and used on EMSA, sequence modifications of the first repeat (upstream position –407) do not interfere with the in vitro binding of the protein factor(s). However, sequence modifications or complete substitution of the second TAGTCA (downstream position –365 bp) repeat almost completely abolishes binding, as judged by the lack of mobility shift of the probe (FIG. 10). Therefore, these results indicate that this (these) protein(s) is (are) binding specifically to the TAGTCA sequence located at –365 bp upstream of the transcription start point, within BREF51. However, since a faint mobility-shifted band was still observed when the modified probes were used, it is possible that sequences flanking the TAGTCA located at position –365 bp are also important for binding, or there is weak binding to the upstream TAGTCA.

bphA gene promoter fusions to the Green Fluorescent Protein (GFP) gene were constructed and transformed into *Aspergillus nidulans* strain GR5 (ATCC #200171). Both the full promoter region (1.8 kbp) and a short version containing fragment 6 and the TATA box (FR6, 0.4 kbp) were placed in front of the GFP coding region (pEBFP, Clontech, Palo Alto, Calif.). Transformants were screened by PCR for the presence of the GFP gene, and grown either in the presence or in the absence of 8 mM benzoic acid. After 5 hours of induction, both full-length and fragment 6 alone of the promoter region were able to induce GFP expression only in the presence of the inducer benzoate (FIG. 9).

Although a putative Benzoate Response Element (BRE) has been reported to be located about 1 kb upstream from the translation start point (van den Brink et al. (2000) Fungal Genet. Biol. 23, 1-17), the results from Electrophoretic Mobility Shift Assays (EMSA) described above showed that a 51 bp region located downstream from the reported BRE consistently binds to a factor present in a total protein extract from benzoate-induced mycelia (FIG. 11). As described above, this 51 bp region possesses a pair of 6-bp direct repeats, with the second one being necessary and sufficient for binding of the protein from the total extract. Therefore, it is contemplated that this 51 bp fragment contains the true BRE in the BphA promoter, and that the TAGTCA within the 51 bp fragment is the true BRE; the 51 bp fragment is referred to as the BRE containing fragment of 51 nucleotides in length, or BREF51. Moreover, the putative BRE proposed by van den Brink et al. ((2000) Mol. Gen. Genet. 263: 601-609) lies in a region which encompasses a well conserved Open Reading Frame (ORF) among fungal species, with no specific function attributed to it to date; this ORF ends at position –532 of SEQ ID NO:1.

The identity of effective BRE(s), along with the minimal fragment size(s) and sequences for chemical inducibility by benzoate and/or related chemicals, is examined by generating fragments and modification of BREF51 (SEQ ID NO:4) by well known techniques; these fragments are then operably linked to a marker gene, and the expression of the marker gene in response to benzoate and/or related chemicals examined. In this way, additional BREs may be identified using the methods and procedures herein. For example, one may test a fragment of SEQ ID NO:6 that is at least 20 nucleotides in length and which contains BRE6 TAGTCA (SEQ ID NO:5). Such fragments may contain sequences upstream of BRE6 (the one located at –365 to –370) or downstream, or both upstream and downstream. Exemplary procedures are described above (and below in the Examples), where Green Fluorescent Protein (GFP) gene constructs are operably linked to test promoters and transformed into *Aspergillus nidulans* strain GR5 (ATCC #200171). The test promoter regions are placed in front of the GFP coding region (pEBFP, Clontech, Palo Alto, Calif.), and transformants screened by PCR for the presence of the GFP gene, and grown either in the presence or in the absence of benzoic acid (at, for example, about 8 mM). The appearance of GFP when *A. nidulans* is grown in the presence of benzoic acid indicate that a test promoter region functions effectively as a benzoate inducible promoter.

The 51 bp fragment (BREF51), and any subfragments or modifications of this region which function as benzoate inducible promoters, are used to generate tandem arrays and combined with a gene promoter, including but not limited to a plant gene promoter.

Thus, discovery of the response element is the first step in the design of a chemically inducible promoter, as described further below.

B. Identification and Cloning of the Gene(s) That Encode TFs That Bind to the BRE Regions Upon Induction by Benzoic Acid While it is not necessary to understand the mechanism to practice the present invention, it is believe that that the mechanism of induction is likely to involve a soluble transcription factor (TF), such as GAD1 and GAD11, or similar proteins (See, e.g., FIGS. 16-19). Two general mechanisms of increasing complexity by which benzoate induces this promoter are depicted in FIG. 12. Regardless of the mechanism of benzoate perception, it is first established whether the transcriptional control is obtained through activation or depression. While not necessary to understand or practice the present invention, it may be necessary not only to identify TFs that would bind to this promoter and regulate transcription of the bphA gene, but also to identify a membrane surface receptor that releases the TFs. A direct binding of benzoate to the promoter is ruled out, in some embodiments, for the simple reason that no such mechanism of transcriptional regulation has ever been identified. In other embodiments, benzoate does directly bind the BRE. Control plants transformed with the promoter elements alone provide confirmation of that assessment, or in the alternative indicate that *Arabidopsis* has its own benzoate inducible TF for some unidentified gene.

1. Internal Induction by Benzoate

FIGS. 12A and 12B depict binding of benzoate to a TF mediating either activation or depression of the promoter. This hypothesis is tested first. Both a biochemical and a molecular affinity binding approach are used to identify the TFs. The binding of TFs in a benzoate-specific manner is tested first; initial results are described below. These experiments consist of electrophoretic mobility-shift assays (EMSAs) as described by Singh et al. ((1986) Nature 319: 154-158). The region of the gel showing the mobility shift is excised, and the protein(s) bound to the DNA fragment are electroeluted. The purified protein(s) are subjected to microsequencing, providing enough information for the identification and cloning of the respective genes. Nuclei are isolated from control or benzoate-induced *A. niger* mycelia according to established protocols (Richardson et al. (1992) Mol. Cell Biol. 12: 337-346), and protein extracts containing the TFs are prepared. The BRE is used to capture the TFs that are revealed by EMSA in a benzoate-specific manner.

Initial efforts to isolate trans-acting factor(s) involved in the regulation of the bphA gene promoter utilized affinity chromatography experiments using either the BRE51 or benzoic acid as affinity ligands. In a first approach, BRE was biotinylated, purified, and allowed to bind to streptavidin-linked paramagnetic particles (PMPs; PolyATtract mRNA Isolation Kit, Promega, Madison, Wis.). Total protein extract from benzoate-induced *A. niger* was added to the solution, incubated for 60 min, and the PMPs were washed several times. Bound proteins were then eluted from the PMPs under high salt conditions. The fractions were electrophoresed on SDS-PAGE, and a protein of approximately 45 kDa could be observed (FIG. 11); however, this factor failed to cause a shift on the mobility of BRE51 when used on EMSA. In a second approach, benzoic acid, immobilized on 4% cross-linked beaded agarose (Sigma, St. Louis, Mo.) was used as the affinity ligand. Again, total protein extract from benzoate-induced *A. niger* was added, the column was washed, and bound proteins eluted under high salt conditions. The eluted fraction also failed to cause mobility shifts on labeled BRE51 when used on EMSA.

Calculation of the stoichiometry of the amount of binding of a protein element that saturates the amount of BREF51 in the EMSA indicates that a minimum of 6 fmoles are present per mg of protein extract. If the factor is about 50 kDa, then this amount represents 300 pg of factor. Thus, a manageable scale-up of about 100-fold is necessary to bind 30 ng of factor needed to detect tryptic fragments by MALDI-TOF MS.

To identify TFs that bind to the BRE, an alternative approach utilizes a yeast 1-hybrid system (Sieweke (2000) Meth. Mol. Biol. 30: 59-77). Simply, the promoter element to be used as "bait" is inserted into a yeast minimal promoter-HIS3 reporter (Clontech). The yeast cells, which are unable to grow in the absence of histidine, are transformed with this construct to create a reporter strain. This reporter strain is then transformed with a GALA activation domain (AD)-cDNA fusion library prepared from *A. niger*. The transformants are plated out on minimal medium lacking histidine. If the AD fusion protein interacts with the promoter fusion, then the yeast will acquire the ability to grow on media without histidine. The plasmid containing the positive cDNA is purified from this colony and sequenced. Such an approach often yields several false positives in addition to true factors. However, each of these recombinant proteins can be tested in a BRE-GFP system to confirm functionality in a timely manner.

As described in more detail earlier, the yeast one-hybrid system screen yielded 17 colonies on SD/-Leu/-His media. DNA sequences obtained from the plasmids isolated from the bacterial cells were translated and compared by BLASTp search (Table 1). Some clones, such as GAD3.1, GAD12.3, GAD12.4, and GAD17.1 constituted false positives, in the sense that the proteins had very high similarity to fungal proteins which functions are known not to be involved with transcriptional regulation. However, most of the cDNAs encoded proteins whose functions are not yet known. These are mostly hypothetical proteins predicted from computer algorithms, and generated during data mining of complete genome sequencing projects. Translated sequences of potential candidates for proteins that interact with BREF51 were also compared to completed genome sequences of *Aspergillus nidulans* (Release 1) and *Neurospora crassa* (Release 3) (tBLASTn search, Whitehead Institute) (Table 2), since both of these species contain a gene with high similarity to the bphA gene from *A. niger*.

Total proteins were isolated from 9 yeast clones which cDNAs encoded proteins that did not show significant similarities to any gene of known function in the databases. Protein extracts from each of these yeast clones were used in EMSA to eliminate those cDNAs that encode proteins that do not interact with BREF51. Yeast clones GAD1 (FIG. 16) and GAD11 (FIG. 17), which contained only one cDNA each, as judged by PCR data, both showed a gel mobility shift of the BREF51 fragment in these assays (FIG. 13). The shift in mobility displayed by GAD1 was similar to that observed with *A. niger* total protein extracts. The protein encoded by GAD1 is highly similar to a predicted protein present in the *A. nidulans* genome (E value $2e^{-83}$), and similar to a hypothetical protein (B24P11.210) in the *N. crassa* genome (E value $4e^{-27}$) (Table 2). GAD1 protein is rich in serine residues (16%), and is predicted by PSORTII to be localized in the nucleus (70.6% probability). It also shows high similarity to a hypothetical serine-rich protein (C13G6.10c) from *S. pombe*. Serine-rich motifs can be phosphorylation targets by protein kinase C in proteins. Also, serine-rich regions have been shown to be part of the transactivation domains of some transcription factors in both mammalian and viral cells. Therefore, while not necessary to understand or practice the present invention if GAD1 is involved in the regulation of BPHprom, GAD1 protein might be always bound to a benzoic acid response element in the bphA promoter. In the absence of benzoic acid GAD1 would be inactive, unable to promote transcription. However, addition of benzoic acid could cause phosphorylation of one of the serine residues in GAD1, leading to its activation. This mode of regulation is analogous to that of the transcription factor CREB, which is involved in responses to cAMP in human cells (Latchman 1997).

GAD11 protein is weakly similar to a *Drosophila melanogaster* homeotic gene regulator, and also to a putative nuclear protein family member from the nematode *C. elegans*. It is also predicted by PSORTII to be localized in the nucleus (94.1% probability). GAD11 was also predicted to have a coiled-coil region consisting of 37 amino acid residues (Lupa's algorithm). The α-helical coiled coil is a structural motif found in many proteins. It consists of two long α-helices with a repeating pattern of hydrophobic side chains that interlock to produce a supercoiled structure. The most important function of coiled-coil regions in myosins and kinesins is for dimerization. Because the coiled coil may be rigid and extended in solution it can act as a spacer or connector between protein domains. This may explain the larger shift in BREF51 mobility in the presence of GAD11 protein extract, since GAD11 proteins may be forming homodimers connected by the coiled-coil region. GAD11 has a homolog in *A. nidulans* (E value $6e^{-29}$), but no homologs in *N. crassa* were found.

Reverse Transcription PCR (RT-PCR) experiments revealed that while GAD1 is expressed constitutively, GAD11 is slightly downregulated in the presence of 8 mM benzoic acid for 5 h (FIG. 14). While not necessary to understand or practice the present invention, if in fact either GAD1 or GAD11 are involved in regulation of the bphA promoter, constitutive transcription of GAD1 does not rule out the possibility that the activity of the GAD1 protein is modulated by benzoic acid. On the other hand, downregulation of the GAD11 gene in the presence of benzoic acid indicates that the protein may function as a transcriptional repressor of the bphA promoter. GAD1 is constitutively expressed, while GAD11 seems to be downregulated in the presence of benzoic acid in the media. While not necessary to understand or practice the present invention, there is a possibility that protein-protein interactions play a role in the regulation of this gene in *A. niger*.

In some embodiments, plants are transformed with vectors containing constitutively expressed TFs and maintained as a line to be used in applications where a novel gene, such as an insect- or pathogen-resistance gene, is to be placed under chemical control. These lines are then transformed with the gene of interest placed under control of a chimeric promoter. Typically, the TF-containing line is prepared using a hygromycin-selectable marker, whereas the promoter-gene construct is prepared using a kanamycin-selectable marker, or vice versa. In other embodiments, plants bearing mutations of a gene of interest are transformed with the TF-vectors, which are subsequently transformed with the promoter-healthy gene construct, using the independently selectable markers.

2. External Induction by Benzoate

While not necessary to understand to practice the invention, a more complicated mechanism of induction may include a surface receptor that binds to benzoate and which then initiates either some kind of signal transduction cascade or the release of a TF that then culminates in the activation of the BPH promoter (FIGS. 12C and D). The hypothesis of a surface receptor was tested by using the p-NH$_2$-benzoate coupled to agarose (as described above) as a non-cleavable external probe. Fungal protoplasts containing the BRE fused to GFP were then prepared, and activation of the BRE (production of the GFP marker) by addition of the agarose-immobilized benzoate derivative to the fungal protoplasts was scored. Whereas the benzoate or p-aminobenzoate induced GFP fluorescence in the BRE-GFP transformed line, no fluorescence was observed when p-nitrobenzoate was linked to the agarose beads. This initial set of results indicates that the TF is a soluble factor. In order to investigate whether the disparity of size between the larger agarose beads and fungal protoplasts may have caused steric problems in binding of the inducer, smaller ligands still incapable of uptake are constructed and utilized to confirm a non-membrane surface location.

C. Construction of the Chemically Inducible Hybrid Promoters and Promoter Systems Following the discovery of the fungal benzoate induced promoter system, which comprises the BRE and transcription factors, an efficient inducible system to control gene expression in cells is engineered; this system consists of a gene minimal promoter containing several copies of the BREs, and the TFs that bind to these promoter elements.

A chemically inducible promoter is, in some embodiments, constructed by placing single or multiple copies of a BRE (e.g. BREF51, or a fragment of SEQ ID NO:6 that is at least 20 nucleotides in length and contains BRE6 TAGTCA (SEQ ID NO:5)), or functionally effective fragments or modifications thereof, upstream of a minimal gene promoter containing a TATA box transcription start signal, to make the benzoate response element functional in cells; the product is referred to as a benzoate inducible hybrid promoter. In some embodiments, additional gene promoter elements may be place around the BREF51, or functionally effective fragments or modifications thereof, to achieve a host cell-specific temporal or spatial expression in response to the chemical application. Thus, the present invention provides a benzoate inducible hybrid promoter comprising benzoate-responsive elements within a gene regulatory region.

The benzoate inducible hybrid promoter is fused to a reporter gene, such as GUS (Jefferson et al. (1987) EMBO J. 6: 3901-3907) or GFP (Haseloff et al. (1997) Proc. Natl. Acad. Sci. USA 94: 2122-2127), and transformed into a cell. The transgenic cells obtained are assayed for the inducibility by expression of the promoter-reporter gene construct alone. It is contemplated that these transgenic cells will not be responsive to benzoate, and instead provide control levels as the level of the "leakiness" of the promoter. Northern blots are carried out to verify both the background and the induced levels of expression of the reporter gene, under different concentrations of the inducer.

As determined by the mechanism of induction, at least one additional plasmid containing at least one gene encoding a transcription factor under constitutive control is introduced into the transgenic cell (e.g. expressing GAD1 [SEQ ID NO:15, or a fragment thereof determined to also serve as a transcription factor] or GAD11 [SEQ ID NO:17, or a fragment thereof determined to also serve as a transcription factor] or a GAD1 homolog (SEQ. ID NO:34), or a GAD11 homolog (SEQ ID NO:36), or functional fragments thereof). A constitutive promoter for the transcription factor ranges from the strong expression of multiple 35S promoters to lesser levels of expression by plant ubiquitin or actin promoters. In a simple system, the coding sequence for an entire transcription factor is operably linked to the promoter, such that nuclear targeting sequences are present; in more complex systems, coding sequences for enhancers, such as the VP16 and nuclear-targeting sequences (Aoyama and Chua (1997) Plant J. 11: 605-612) are linked to coding sequences for a truncated version of transcription factors which comprises effector and DNA-binding domains of the transcription factor, resulting in a fusion protein factor. The combination of the benzoate-inducible hybrid promoter and at least one additional gene encoding a transcription factor (which includes but is not limited to transcription factor fusion proteins and other modifications) is referred to as a benzoate-inducible promoter system. In some embodiments, the transcription factor is GAD1 or GAD11, or functional fragments thereof (functional fragments can be found using the methods described above and the Examples using test fragments in place of full length GAD1 or GAD11).

The effects, if any, of the inducible system on the overall performance of the cells are also evaluated.

In some embodiments, the cell to be transformed is a plant cell; in further embodiments, a transgenic plant cell is regenerated into a transgenic plant. In other embodiments, an *Arabidopsis* plant is transformed by *Agrobacterium*-mediated transformation, as described by Clough and Bent ((1998) Plant J. 16: 735-743). The transgenic plants obtained are assayed for the inducibility by expression of the promoter-reporter gene construct alone. As described above, it is contemplated that these transgenic plants will not be responsive to benzoate, and instead provide control levels as the level of the "leakiness" of the promoter. Northern blots are carried out to verify both the background and the induced levels of expression of the reporter gene, under different concentrations of the inducer.

As determined by the mechanism of induction, at least one additional plasmid comprising at least one gene encoding a transcription factor under constitutive control, as described above, is introduced into these plants.

The effects, if any, of the inducible system on the overall performance of the plants are also evaluated. Characteristics assessed include but are not limited to pathogen or insect resistance, whole plant and tissue organization, flowering time, fertility (pollen or egg) or any phenotypic signs of toxicity. Thus, for example, it is contemplated that the inducible system might be utilized to induce male sterility or to overcome it, depending on the application. This could be a very useful application in breeding.

II. Utilization of Hybrid Benzoate Inducible Promoters to Control Expression of Nucleic Acid Sequences of Interest The present invention further comprises methods of controlling expression of nucleic acid sequences of interest using a benzoate inducible hybrid promoter or a benzoate inducible promoter system of the present invention. In some embodiments, nucleic acid sequences are controlled by a benzoate inducible hybrid promoter of the present invention. In other embodiments, nucleic acid sequences are controlled by the benzoate inducible promoter system of the present invention. The following description is directed to nucleic acid sequences under control of either.

A. Nucleic Acid Sequences of Interest

In some embodiments, the compositions and methods of the present invention are used to control or direct nucleic acid sequence expression in plant seed tissue. Although such sequences are referred to as "genes" under this section, it is understood that these sequences refer to the coding section of the gene which is expressed as an RNA product, but that these sequences do not necessarily include the promoter region, although other regulatory regions may be included. In certain embodiments the endogenous promoter region is not included; in others, it may be. The methods are not limited to the control of any particular gene. Indeed, a variety of genes are contemplated for control, including, but not limited to those, described below.

In some embodiments, the gene of interest is an endogenous plant gene. In other embodiments, the gene of interest is an exogenous plant gene. The methods of the present invention are not limited to any particular plant. Indeed, a variety of plants are contemplated, including, but not limited to angiosperms, gymnosperms, monocotyledons, and dicotyledons. Specific plants contemplated include, but are not limited to, wheat, barley, maize, rye, rice, soybean, hemp, triticale, apricots, oranges, quince, melon, plum, cherry, peach, nectarine, strawberry, grape, raspberry, blackberry, pineapple, papaya, mango, banana, grapefruits, apples, pears, avocados, walnuts, almonds, filberts, pecans, carrots, lettuce, zucchini, tomatoes, beans, peas, cabbage, chicory, onion, garlic, pepper, squash, pumpkin, celery, turnips, radish, spinach, cauliflower, potatoes, sweet potatoes, broccoli, eggplant, cucumber, asparagus, poplar, pine, sequoia, cedar, oak, tobacco, clover, lotus, jojoba, rapeseed, sunflower, sorghum, sugarcane, sugar beet, safflower, *Arabidopsis*, alfalfa, and cotton. Additional plants include but are not limited to oats (which are important cereal crop for production of cholesterol-lowering b-glucans, cassava (which is fifth in world food crop production, after corn, wheat, rice, and potatoes), and eucalyptus (an engineered tree species for the pulp and paper industry). Additional plants include turf grasses, but are not limited to ryegrass, timothy, Bermuda, Bahia, Kentucky bluegrass, zoysia, and the like. Turf grasses are multibillion dollar industries that could benefit from the present invention.

In some embodiments, the compositions and methods of the present invention are used to control or direct the expression of a gene involved in a metabolic pathway of a plant cell (for example, genes responsible for the synthesis or metabolism of peptides, proteins, fatty acids, lipids, waxes, oils, starches, sugars, carbohydrates, flavors, odors, fragrances, toxins, carotenoid pigments, hormones, cell wall polymers, gene regulatory molecules, flavonoids, storage proteins, phenolic acids, coumarins, alkaloids, quinones, lignins, glucosinolates, tannins, aliphatic amines, celluloses, pectins, polysaccharides, glycoproteins and glycolipids), in resistance or susceptibility of a plant to diseases (for example, to viral infection), in a visible phenotype (for example, flower color intensity, color hue and color pattern); or cell differentiation. For example, specific genes contemplated include, but are not limited to, those described in U.S. Pat. Nos. 5,107,065; 5,283,184; and 5,034,323; each of which is herein incorporated by reference.

In other embodiments, the compositions and methods of the present invention are used to alter the expression of a plant gene whose function is unknown in order to elucidate its function. Sense and antisense fragments of the gene are introduced to the plant. The plant is then examined for phenotypic changes (for example, metabolic or visible).

B. Methods of Transforming Plants

1. Vectors

Nucleic acid sequences of interest intended for expression in plants are first assembled in expression cassettes comprising a promoter (for example, the benzoate inducible hybrid promoter regions of the present invention). Methods which are well known to those skilled in the art may be used to construct expression vectors containing nucleic acid sequences of interest and appropriate transcriptional and translational control elements. These methods include in vitro recombinant DNA techniques, synthetic techniques, and in vivo genetic recombination. Such techniques are widely described in the art (See for example, Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., both of which are herein incorporated by reference).

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See for example, Odell et al., Nature 313:810 (1985); Rosenberg et al., Gene, 56:125 (1987); Guerineau et al., Mol. Gen. Genet., 262:141 (1991); Proudfoot, Cell, 64:671 (1991); Sanfacon et al., Genes Dev., 5:141; Mogen et al., Plant Cell, 2:1261 (1990); Munroe et al., Gene, 91:151 (1990); Ballas et al., Nucleic Acids Res. 17:7891 (1989); Joshi et al., Nucleic Acid Res., 15:9627 (1987)).

In addition, in some embodiments, constructs for expression of a nucleic acid sequence of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al., Genes Develop. 1: 1183 (1987)). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Kalderon et al., Cell 39:499 (1984); Lassner et al., Plant Molecular Biology 17:229 (1991)), a plant translational consensus sequence (Joshi, Nucleic Acids Research 15:6643 (1987)), an intron (Luehrsen and Walbot, Mol. Gen. Genet. 225:81 (1991)), and the like, operably linked to the nucleic acid sequence of interest.

In preparing the construct comprising the nucleic acid sequence of interest, various DNA fragments can be manipulated, so as to provide for the DNA sequences in the desired orientation (for example, sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (for example, transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, Gene 19: 259 (1982); Bevan et al., Nature 304:184 (1983)), the bar gene which confers resistance to the herbicide phosphinothricin (White et al., Nucl Acids Res. 18:1062 (1990); Spencer et al., Theor. Appl. Genet. 79: 625 (1990)), the hph gene which confers resistance to the antibiotic hygromycin (Blochinger and Diggelmann, Mol. Cell. Biol. 4:2929 (1984)), and the dhfr gene, which confers resistance to methotrexate (Bourouis et al., EMBO J., 2:1099 (1983)).

In some embodiments of the present invention, transformation is carried out using *Agrobacterium tumefaciens* mediated methods. Many vectors are available for transformation using *Agrobacterium tumefaciens*. These typically carry at least one T-DNA border sequence and include vectors such as pBIN19 (Bevan, Nucl. Acids Res., 12:8711 (1984)). An additional vector useful for *Agrobacterium*-mediated transformation is the binary vector pCIB10 (Rothstein et al., Gene 53:153 (1987)) which contains a gene encoding kanamycin resistance for selection in plants, T-DNA right and left border sequences and incorporates sequences from the wide host-range plasmid pRK252 allowing it to replicate in both *E. coli* and *Agrobacterium*. Various derivatives of pCIB10 have been constructed which incorporate the gene for hygromycin B phosphotransferase (See for example, Gritz et al., Gene, 25: 179 (1983)). These derivatives enable selection of transgenic plant cells on hygromycin only (pCIB743), or hygromycin and kanamycin (pCIB715, pCIB717).

In some embodiments of the present invention, the nucleic acid sequence of interest is introduced directly into a plant. One vector useful for direct gene transfer techniques in combination with selection by the herbicide Basta (or phosphinothricin) is a modified version of the plasmid pCIB246, with the CaMV 35S promoter replaced by a benzoate inducible hybrid promoter of the present invention (as described above) in operational fusion to the *E. coli* GUS gene and the CaMV 35S transcriptional terminator and is described in WO 93/07278, which is herein incorporated by reference. In some embodiments of the present invention, this vector is modified to include a benzoate inducible hybrid promoter of the present invention (as described above) operatively linked to two nucleic acid sequences of interest. The gene providing resistance to phosphinothricin is the bar gene from *Streptomyces hygroscopicus* (Thompson et al., EMBO J., 6:2519 (1987)).

2. Transformation Techniques

Once the nucleic acid sequences have been operatively linked to a benzoate inducible hybrid promoter of the present invention and inserted into a suitable vector for the particular transformation technique utilized (for example, one of the vectors described above), the recombinant DNA described above can be introduced into a plant cell in a number of art-recognized ways. Those skilled in the art will appreciate that the choice of method depends upon the type of plant targeted for transformation. In some embodiments, the vector is maintained episomally. In other embodiments, the vector is integrated into the genome. In some embodiments, plants are independently transformed into a line carrying the constitutively expressed transcription factor (or modification or fusion thereof), or the benzoate inducible hybrid promoter-target gene construct is transformed into a line of choice and crossed with lines carrying the transcription factor (or modification or fusion thereof), back-crossed and selected for progeny carrying both constructs.

In some embodiments, vectors useful in the practice of the present invention are microinjected directly into plant cells by use of micropipettes to mechanically transfer the recombinant DNA (Crossway, Mol. Gen. Genet, 202:179 (1985)). In still other embodiments, the vector is transferred into the plant cell by using polyethylene glycol (Krens et al., Nature, 296:72 (1982); Crossway et al., BioTechniques, 4:320 (1986)); fusion of protoplasts with other entities, either mini-cells, cells, lysosomes or other fusible lipid-surfaced bodies (Fraley et al., Proc. Natl. Acad. Sci., USA, 79:1859 (1982)); protoplast, transformation (EP 0 292 435; herein incorporated by reference); direct gene transfer (Paszkowski et al., EMBO J., 3:2717 (1984); Hayashimoto et al., Plant Physiol. 93:857 (1990)).

In other embodiments, the vector may also be introduced into the plant cells by electroporation. (Fromm, et al., Pro. Natl Acad. Sci. USA 82:5824, 1985; Riggs et al., Proc. Natl. Acad. Sci. USA 83:5602 (1986)). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In other embodiments, DNA is introduced into plant cells by what is called the "pollen-tube pathway" whereby naked DNA plasmids or *Agrobacterium*-mediated transfer is made at the time of anthesis by dipping the flowers into a solution of the plasmid-containing bacteria or by spraying the plasmid-containing bacteria as an aerosol onto the flowers (Clough and Bent (1998) Plant J. 16: 735-743; Bent (2000) Plant Physiol. 124: 1540-1547). In other embodiments, plants are transformed by cutting styles on the morning of anthesis and droplets of solution containing the DNA are added directly to the cut ends (Huang et al. (1998) Chin. Sci. Bull. 44: 698-708; Zeng et al. (1998) Chin. Sci. Bull. 43: 798-803; Hu and Wang (1999) In Vitro Cell. Devel. Biol.-Plant 35: 417-420; Tjokrokusumo et al. (2000) Plant Cell Rep. 19: 792-797; and Herrero (2001) Sex. Plant Reprod. 14: 3-7). In each of these embodiments, the pollen or egg cells are transformed coincident with fertilization, and the successful transformants selected upon germination.

In still further embodiments, the vector is introduced through ballistic particle acceleration using devices (for example, available from Agracetus, Inc., Madison, Wis. and Dupont, Inc., Wilmington, Del.). (See for example, U.S. Pat. No. 4,945,050; herein incorporated by reference; and McCabe et al., Biotechnology 6:923 (1988)). See also, Weissinger et al., Annual Rev. Genet. 22:421 (1988); Sanford et al., Particulate Science and Technology, 5:27 (1987) (onion); Svab et al., Proc. Natl. Acad. Sci. USA, 87:8526 (1990) (tobacco chloroplast); Christou et al., Plant Physiol., 87:671 (1988) (soybean); McCabe et al., Bio/Technology 6:923 (1988) (soybean); Klein et al., Proc. Natl. Acad. Sci. USA, 85:4305 (1988) (maize); Klein et al., Bio/Technology, 6:559 (1988) (maize); Klein et al., Plant Physiol., 91:4404 (1988) (maize); Fromm et al., Bio/Technology, 8:833 (1990); and Gordon-Kamm et al., Plant Cell, 2:603 (1990) (maize); Koziel et al., Biotechnology, 11:194 (1993) (maize); Hill et al., Euphytica, 85:119 (1995) and Koziel et al., Annals of the New York Academy of Sciences 792:164 (1996); Shimamoto et al., Nature 338: 274 (1989) (rice); Christou et al., Biotechnology, 9:957 (1991) (rice); Datta et al., Bio/Technology 8:736 (1990) (rice); European Patent Application EP 0 332 581, herein incorporated by reference (orchard grass and other Pooideae); Vasil et al., Biotechnology, 11: 1553 (1993) (wheat); Weeks et al., Plant Physiol., 102: 1077 (1993) (wheat); Wan et al., Plant Physiol. 104: 37 (1994) (barley); Knudsen and Muller, Planta, 185:330 (1991) (barley); Umbeck et al., Bio/Technology 5: 263 (1987) (cotton); Casas et al., Proc. Natl. Acad. Sci. USA 90:11212 (1993) (sorghum); Somers et al., Bio/Technology 10:1589 (1992) (oat); Torbert et al., Plant Cell Reports, 14:635 (1995) (oat); Weeks et al., Plant Physiol., 102:1077 (1993) (wheat); and Chang et al., WO 94/13822 (wheat).

In addition to direct transformation, in some embodiments, the vectors comprising the nucleic acid sequences of interest and a promoter of the present invention are transferred using *Agrobacterium*-mediated transformation (Hinchee et al., Biotechnology, 6:915 (1988); Ishida et al., Nature Biotechnology 14:745 (1996)). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (for example, nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, Science, 237: 1176 (1987)). Species which are susceptible infection by *Agrobacterium* may be transformed in vitro.

3. Regeneration

After determination of the presence and expression of the desired gene products, whole plants are regenerated. Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. I, 1984, and Vol. III, 1986. It is known that many plants can be regenerated from cultured cells or tissues, including both monocots and dicots, and including for example, crop plants, ornamentals and other horticultural plants, shrubs, and trees. Means for regeneration vary from species to species of plants, but generally a suspension of transformed protoplasts is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

C. Increasing or Decreasing Gene Expression

It is contemplated that benzoate inducible hybrid promoters and/or benzoate inducible promoter systems of the present invention may be utilized to either increase or decrease the level of expression of nucleic acid sequences of interest in transfected cells as compared to the levels in wild-type cells. Accordingly, in some embodiments, expression in plants by the methods described above leads to the overexpression of nucleic acid sequences of interest in transgenic plants, plant tissues, or plant cells.

In other embodiments of the present invention, benzoate inducible hybrid promoters and/or benzoate inducible promoter systems of the present invention are utilized to decrease the level of expression of nucleic acid sequences of interest in transgenic plants, plant tissues, or plant cells as compared to wild-type plants, plant tissues, or plant cells. One method of reducing expression utilizes expression of antisense transcripts. Antisense RNA has been used to inhibit plant target genes in a tissue-specific manner (for example, van der Krol et al., Biotechniques 6:958-976 (1988)). Antisense inhibition has been shown using the entire cDNA sequence as well as a partial cDNA sequence (for example, Sheehy et al., Proc. Natl. Acad. Sci. USA 85:8805-8809 (1988); Cannon et al., Plant Mol. Biol. 15:39-47 (1990)). There is also evidence that 3' non-coding sequence fragment and 5' coding sequence fragments, containing as few as 41 base-pairs of a 1.87 kb cDNA, can play important roles in antisense inhibition (Ch'ng et al., Proc. Natl. Acad. Sci. USA 86:10006-10010 (1989)).

Accordingly, in some embodiments, benzoate inducible hybrid promoters of the present invention (see, for example, FIG. 15) are operably linked to nucleic acid sequences of interest which are oriented in a vector and expressed so as to produce antisense transcripts. To accomplish this, a nucleic acid segment from the desired gene is cloned and operably linked to a benzoate inducible hybrid promoter of the present invention such that the antisense strand of RNA will be transcribed. The expression cassette is then transformed into plants, by itself or as part of the benzoate inducible hybrid promoter system, and the antisense strand of RNA is produced in response to application of the chemical inducer. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff, et al., Nature 334:585-591 (1988).

Another method of reducing expression of nucleic acid sequences of interest utilizes the phenomenon of cosuppression or gene silencing (See for example, U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (for example, Napoli et al., Plant Cell 2:279-289 (1990); van der Krol et al., Plant Cell 2:291-299 (1990); Smith et al., Mol. Gen. Genetics 224:477-481 (1990)). Accordingly, in some embodiments the benzoate inducible hybrid promoter of the present invention are operably linked to nucleic acid sequences of interest which are expressed in another species of plant, either alone or as part of the benzoate inducible hybrid system, to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

In some embodiments, the nucleic acid sequence of interest is an siRNA (RNAi) molecule that is able to suppress a targeted RNA transcript. RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired stricture characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:4948; Elbashir et al., Genes Dev. 2001; 15: 188-200; and Elbashir et al., EMBO J. 2001; 20:6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

In other embodiments, the nucleic acid sequence of interest is a gene conversion gene (e.g. to direct the change in an allele in a cell). Methods for designing and employing gene conversion genes are described in U.S. Pat. Pub. US20030051270 (herein incorporated by reference).

III. Methods of Production of Gene Products of Interest

The present invention further comprises methods of producing products of nucleic acid sequences of interest by using benzoate inducible hybrid promoters and/or benzoate inducible hybrid promoter systems of the present invention. Products of nucleic acid sequences include proteins, RNA, and metabolic products or catalytically active proteins or RNAs, such as secondary metabolites, sugars, lipids, modified proteins, and nucleic acids.

A. Production in Plants

In some embodiments, the present invention provides methods of producing one or more gene products of interest using a benzoate inducible hybrid promoter and/or benzoate inducible hybrid promoter system of the present invention. In some embodiments, a benzoate inducible hybrid promoter of the present invention (as described above) is used to express two gene products of interest (for example, two subunits of a multi-subunit protein or two members of a metabolic pathway) from the same promoter construct. In other embodiments, a sequence that hybridizes to a benzoate inducible hybrid promoter of the present invention is utilized. One skilled in the art will recognize, in view of the present disclosure, that the expression vectors comprising a benzoate inducible hybrid promoter of the present invention and one or more nucleic acid sequences of interest may contain additional regulatory and enhancer elements specific to the host cell utilized for expression (for example, those described above or below).

In some embodiments, one or more gene products of interest are expressed in regenerated plants (for example, in seed tissue to elicit a specific metabolic response). In other embodiments, polypeptides of interest are expressed in plants for use in food stuffs (for example, to increase the nutritional value or to express a pharmaceutical compound). In still further embodiments, one or more polypeptides of interest are expressed in cell culture (for example, plant, bacterial, or eukaryotic cells) for the purpose of purifying the polypeptides of interest from the cell culture.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements may be utilized. For example, for expression mediated by plant viruses, viral promoters or leader sequences may be included in the vector.

In some preferred embodiments, the 5' leader sequence is included in the expression cassette construct. Such leader sequences can act to enhance translation. Translation leaders are known in the art and include: picornavirus leaders, for example, EMCV leader (Encephalomyocarditis 5' non-coding region; Elroy-Stein et al., PNAS, 86:6126 (1989)); potyvirus leaders, for example, TEV leader (Tobacco Etch Virus; Niepel and Gallie, J Virol., 73:9080 (1999)) MDMV leader (Maize Dwarf Mosaic Virus; Virology, 154:9 (1986)), and human immunoglobulin heavy-chain binding protein (BiP; Macejak and Samow, Nature 353:90 (1991)); untranslated leader from the coat protein mRNA of alfalfa mosaic virus (AMV RNA 4; Jobling and Gebrke, Nature, 325:622 (1987)); tobacco mosaic virus leader (TMV; Gallie et al., Molecular-Biology of RNA, pages 237-256 (1989)); and maize chlorotic mottle virus leader (MCMV; Lommel et al., Virology 91:382 (1991); Della-Cioppa et al., Plant Physiology 84:965 (1987)).

In some embodiments, one or more polypeptides of interest are expressed in plants using stable transformation, as described above. In other embodiments, plant vectors are created using a recombinant plant virus containing a recombinant plant viral nucleic acid, as described in PCT publication WO 96/40867 which is herein incorporated by reference. Subsequently, the recombinant plant viral nucleic acid which contains one or more nucleic acid sequences encoding polypeptides of interest are transcribed or expressed in the infected tissues of the plant host and the polypeptides are recovered from the plant, as described in WO 99/36516, which is herein incorporated by reference.

In this embodiment, recombinant plant viral nucleic acids which contain a benzoate inducible hybrid promoter of the present invention linked to at least one nucleic acid sequence of interest are utilized. The recombinant plant viral nucleic acids have substantial sequence homology to plant viral nucleic acid sequences and may be derived from an RNA, DNA, cDNA or a chemically synthesized RNA or DNA. A partial listing of suitable viruses is described below.

The first step in producing recombinant plant viral nucleic acids according to this particular embodiment is to modify the nucleic acid sequences of the plant viral nucleic acid sequence by known techniques such that a benzoate inducible hybrid promoter of the present invention is inserted into the plant viral nucleic acid without destroying the biological function of the plant viral nucleic acid. The native coat protein coding sequence may be deleted in some embodiments, placed under the control of a non-native subgenomic promoter in other embodiments, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, which may be native or a nonnative coat protein coding sequence, under control of one of the native or non-native subgenomic promoters. The coat protein is involved in the systemic infection of the plant host.

Some of the viruses suitable for use in the present invention include, but are not limited to viruses from the tobamovirus group such as Tobacco Mosaic virus (TMV), Ribgrass Mosaic Virus (RGM), Cowpea Mosaic virus (CMV), Alfalfa Mosaic virus (AMV), Cucumber Green Mottle Mosaic virus watermelon strain (CGMMV-W) and Oat Mosaic virus (OMV) and viruses from the brome mosaic virus group such as Brome Mosaic virus (BMV), broad bean mottle virus and cowpea chlorotic mottle virus. Additional suitable viruses include Rice Necrosis virus (RNV), and geminiviruses such as tomato golden mosaic virus (TGMV), Cassava latent virus (CLV) and maize streak virus (MSV).

Other embodiments of plant vectors used for the expression of sequences encoding polypeptides include, for example, a benzoate inducible hybrid promoter of the present invention used in combination with the omega leader sequence from TMV (Takamatsu, EMBO J. 6:307 (1987)). These constructs can be introduced into plant cells by any suitable methods, including, but not limited to those described above.

B. Confirmation of Product Presence

Host cells which contain a nucleic acid sequence of interest may be identified by a variety of procedures known to those of skill in the art. These procedures include, but are not limited to, enzyme assay, DNA-DNA or DNA-RNA hybridizations and protein bioassay or immunoassay techniques which include membrane, solution, or chip based technologies for the detection and/or quantitation of nucleic acid or protein.

The presence of nucleic acid sequences of interest can be detected by DNA-DNA or DNA-RNA hybridization or amplification using probes or portions or fragments of polynucleotides encoding the polypeptide. Nucleic acid amplification based assays involve the use of oligonucleotides or oligomers based on the sequences of interest to detect transformants containing DNA or RNA encoding the polypeptide.

A variety of protocols for detecting and measuring the expression of a polypeptide using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the polypeptide is preferred, but a competitive binding assay may be employed. These and other assays are described, among other places, in Hampton et al. (1990); Serological Methods, a Laboratory Manual, APS Press, St Paul, Minn.; and Maddox et al., J. Exp. Med., 158: 1211 (1983)).

A wide variety of labels and conjugation techniques are known by those skilled in the art and may be used in various nucleic acid and amino acid assays. Means for producing labeled hybridization or PCR probes for detecting sequences related to polynucleotides encoding a polypeptide of interest include oligonucleotide labeling, nick translation, end-labeling or PCR amplification using a labeled nucleotide. Alternatively, the sequences encoding the polypeptide, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.), Promega Corporation (Madison, Wis.) and U.S. Biochemical Corp. (Cleveland, Ohio). Suitable reporter molecules or labels, which may be used, include radionucleotides, enzymes, fluorescent, chemiluminescent, or chromogenic agents as well as substrates, cofactors, inhibitors, magnetic particles, and the like.

C. Recovery of Expressed Products

In some embodiments of the present invention, it is desirable to recover expressed protein from seed tissue. In other embodiments, it is desirable to recover expressed protein from floral, leaf, stem, root, or other tissues. Plants transformed with nucleic acid sequences encoding one or more polypeptides of interest may be cultivated under conditions suitable for high expression and subsequent recovery of the protein from the appropriate tissue. The protein produced by a recombinant cell may be secreted or contained intracellularly depending on the sequence and/or the vector used. As will be understood by those of skill in the art, expression vectors containing polynucleotides which encode the polypeptide(s) of interest may be designed to contain signal sequences which direct secretion of the polypeptide into a particular cell compartment, such as a vacuole or a plastid, or secretion from the cell into the extracellular matrix or cell wall.

In other embodiments of the present invention, other recombinant constructions may be used to join sequences encoding a polypeptide to nucleic acid sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (available from Invitrogen, San Diego, Calif.) between the purification domain and the polypeptide of interest may be used to facilitate purification. One such expression vector provides for expression of a fusion protein containing the polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al., Prot. Exp. Purif., 3:263 (1992) while the enterokinase cleavage site provides a means for purifying the polypeptide from the fusion protein. A discussion of vectors which contain fusion proteins is provided in Kroll et al., DNA Cell Biol., 12:441 (1993)).

In yet other embodiments, it is desirable to recover other products of interest, such as RNA, or products of metabolically active proteins, such as secondary metabolites, sugars, lipids, modified proteins, and nucleic acids. Such products are recovered by methods well known in the art.

IV. Chemical Induction of Flowering

The chemically inducible promoter system developed for use in plants, as described above, can be utilized to control a developmental phase in plants. In one aspect of the present invention, a chemically inducible promoter system developed for use in plants is used to control or regulate flowering in plants. The first step is the development of a model that employs a chemically inducible promoter and required transcription factors to control flowering in plants.

A. A Test Model for Induction of Flowering by a Chemically Induced Promoter

One of the more practical uses for a chemically inducible promoter is to control a plant developmental process. For many decades, plant physiologists have been attempting to elucidate the mechanism by which flowering is controlled. Much of this work has been focused on identifying the specific plant growth regulators produced in the leaves and transported to the apical and lateral meristems where they induce, singly or in combination, a change from a vegetative to a floral developmental program. The elusive florigen has never been identified. However, a gene has been identified in *Arabidopsis* that appears to be one of several key transcriptional control factors necessary for transition of the meristem to flowering mode. The gene, called LEAFY, was identified as a mutation that markedly delayed the onset of flowering (Schultz and Haughn (1991) Plant Cell 3, 771-781; Weigel et al. (1992) Cell 69, 843-859). This transition is controlled by several genetic pathways that impact the change in developmental state (Levy and Dean 1998). Another such factor is a floral inducer called FLOWERING LOCUS T (FT), a mutant of which also causes late flowering (Koorneef et al. (1991) Mol. Gen. Genet. 229: 57-66). Activation tagging of FT, which causes constitutive expression of the FT, induces precocious flowering at the three-leaf stage of seedling development (Kardailsky et al. (1999) Science 286: 1962-1965). This gene works in parallel with LEAFY, but obviously exerts marked control of the timing of flowering.

The ability of a chemically controllable promoter to induce flowering was tested in *Arabidopsis* containing a disabled FT gene. The ft-3 mutant *Arabidopsis*, which is caused by missense mutation deleting the entire C-terminal region of the protein and displays a significant delay in the flowering response, was obtained from the *Arabidopsis* Stock Center (Ohio State Univ).

A chemically inducible promoter available to test induction of flowering is the glucocorticoid receptor-promoter element system that is induced by the glucocorticoid, dexamethasone (Aoyama and Chua (1997) Plant J. 11: 605-612; Kunkel et al. (1999) Nature Biotech. 17: 916-919). This system has recently been engineered to avoid some leakiness problems originally experienced, and the plasmid constructs for the two necessary components have been obtained. The general strategy of the glucocorticoid receptor promoter was described by Aoyama and Chua ((1997) Plant J. 11, 605-612). Dr. Jen Sheen (Massachusetts General hospital) restructured the glucocorticoid promoter to be LexA-based instead of Gal4, and this provided a finer control. This promoter can be assembled from available sequences by one skilled in the art.

Wild-type FT cDNA was obtained from Dr. Detlef Weigel (formerly of the Salk Institute, La Jolla, Calif., and now Max Planck Institute for Developmental Biology, Tübingen, Germany); the wild-type FT cDNA was prepared from transcripts for flowering *Arabidopsis* plants. This and other *Arabidopsis* cDNAs are available from Dr. Weigel or from a publicly accessible Riken BioResource Center, Japan at the riken web site. As the *Arabidopsis* genome is completely sequenced and publicly available, one skilled in the art can design primers and obtain a full-length FT gene by RT-PCR. Wild-type FT cDNA was placed under the control of the LexA-based glucocorticoid inducible promoter (called Lex-FT), and this construct was subcloned into the pCAMBIA 1305.1 binary vector (CAMBIA, Canberra, Australia). In a separate construct, the hybrid transactivating factor LSVG, under a constitutively expressed promoter, was cloned into pCAMBIA 1302 (CAMBIA, Canberra, Australia). Both vectors were then transformed by vacuum infiltration (Clough and Bent (1998) Plant J. 16: 735-743) into the *Arabidopsis* ft plants. Ti seeds were harvested, and plated out on selective media, containing the antibiotic hygromycin, in order to recover putative transformants.

The selected transformants have been assayed for GUS or GFP expression (depending on the pCAMBIA vector used), and the presence of the inducible promoter system and the FT gene have been confirmed by PCR. A problem was encountered with the plants containing the pCAMBIA 1302-LSVG constitutive-expressant construct, probably due to a slow accumulation of toxic levels the hybrid transacting factor LSVG during the prolonged growth before flowering. The transgenic plants died shortly after flowering, yielding few or no seeds from the plants. To overcome this unexpected difficulty with this test system, the LSVG hybrid transactivator was subcloned into a different pCAMBIA vector, with a kanamycin selectable marker instead of hygromycin. Confirmed Lex-FT homozygous plants are transformed with the new construct. This approach provides not only a faster way of incorporating both components into the same plant, but also overcomes the toxicity problem by spraying the test plants after only one-third the growth period.

As described above, the Lex-FT construct has been successfully integrated into non-leaky ft homozygous mutants; these plants are then transformed with the altered construct containing a constitutively expressed LSVG in a binary vector with kanamycin resistance.

B. Induction of Flowering by the Hybrid Promoter System Described Above

The dexamethasone inducible promoter system described above is replaced with a benzoate-inducible promoter system, as described above.

An embodiment of the benzoate inducible hybrid promoter system is shown in FIG. 15. The first DNA construct is the Inducible Promoter itself, with 3 or more copies of BREF51 (BRE), fused to the TATA-box of the Cauliflower Mosaic Virus 35S promoter (35S TATA). A polycloning site is engineered between the 35S TATA promoter sequence and the Nopaline Synthase (nos) terminator for ease of manipulation. This hybrid promoter drives expression of any downstream gene of interest in a benzoate inducible manner. The nos terminator is placed downstream of the coding region and, in addition to stop codons in every reading frame, contains a polyadenylation signal sequence.

The second DNA construct is the Transacting Factor or Transcriptional Factor, which will be constitutively expressed by using a full-length CaMV35S promoter. A chimeric transcription factor construct may also be employed that consists of a combination of modules. The first module is the Nuclear Localization Signal (NLS) from the SV40 viral protein. The Activation Domain (AD) of the Herpes Simplex Viral Protein 16 (VP16) constitutes the second module. The third and final module have the BREF51 DNA binding domain (BRE DBD) fused to the benzoate receptor domain (Benz Rec), both identified from the *A. niger* transcription factor. The nos terminator sequence is also be placed downstream of this construct.

V. Exemplary Applications

There is an avid interest to precisely control the timing and level of expression of transgenes in plants and other cell types. Such control has great utility in both basic research and in agriculture. Thus, the hybrid benzoate inducible promoter system described above has utility in both research and agricultural applications. The promoter system can be used to control expression of exogenous genes, of endogenous genes, and of antisense genes targeted to either or both exogenous or endogenous genes.

In research, using mutants to understand unknown gene function is severely limited when such mutations are lethal. Placing such genes under inducible control of the hybrid benzoate inducible promoter system described above constitutes a powerful solution to this problem. Spraying a plant with an innocuous chemical and switching on a gene of interest provides a powerful tool for basic studies, such as phenotypes associated with specific gene expression, as well as gene interactions in plants.

Moreover, practical and large-scale applications are also anticipated for the hybrid benzoate inducible promoter system described above. Turning on engineered plant defense genes only upon attack of the pathogen or insect is anticipated to save millions of dollars in pesticide application; the precise timing flowering in greenhouse operations is anticipated to not only save money, but to open up additional market products to the floricultural industries. As benzoate is degraded easily and is non-toxic, it can be used in the field as a potent inducer of agronomic fruits, such as processing tomatoes, which are collected mechanically in a single harvest. Precision timing of flowering will better synchronize the flower and subsequent fruit production so that a single harvest method will result in higher yields. Precise control of transgene expression in a specific plant tissue has been accomplished by means of using several different tissue-specific promoters. Another contemplated application is the use of the benzoate inducible hybrid promoter in control of fertility, where a pollen sterility gene under control of the hybrid promoter could be induced or silenced, depending on the desire of the breeder.

Hence, the present invention provides the hybrid benzoate inducible promoter system in a kit for sale by molecular biology supply companies. In some embodiments, a kit comprises two plasmids: a first binary plasmid with a range of constitutively expressing promoters capable of controlling expression of at least one benzoate-activatable transcription factor and a hygromycin resistance selectable marker; and a second binary plasmid comprising a benzoate inducible promoter as described above, an efficient polycloning site for insertion of a coding sequence under control of the benzoate inducible promoter, and a terminator coupled with a kanamycin-resistance marker. One skilled in the art utilizes the components of the kit to carry out the transformations. In some embodiments, the plasmids are suitably engineered for a particular host; for example, the plasmids and benzoate inducible promoter are capable of transformation of and expression in plants, as described above.

Such kits are contemplated to find use in both the research lab, and in the development of agricultural plants where timing of control of gene expression is desired.

Precise control of gene expression is equally important in animal and fungal systems with respect to understanding the function of genes for which mutations would otherwise be lethal. For example, to determine if mutations that would be lethal at particular stages of organism development, antisense (or RNAi) constructs of the gene could be kept silent until induction was desired. Although controlling in vitro development in cell cultures would be more facile, because benzoate is non-toxic, its use in vivo in animal model systems is feasible. In other applications, the function of genes suspected to be mutated in animal and fungal model systems could be tested by placing a complementary gene under control by the chemical. The basic benzoate activation system would be the same, but other minimal promoters and selective media would be employed that are optimal for non-plant systems.

For all organisms, plant, animal and fungal, further refinements of the benzoate-inducible promoter system could be made to increase sensitivity to the inducing compound, such as in fusion of the transcription factor with enhanced nuclear localization signals or amplification of activation through simultaneous induction of the transcription factor in a benzoate-specific manner.

EXPERIMENTAL

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); µM (micromolar); mol (moles); mmol (millimoles); µmol (micromoles); nmol (nanomoles); pmol (picomoles); fmoles (femtomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); BPH (benzoate para-hydroxylase); Benzoate Response Element (BRE); BREF51 (Benzoate Response Factor containing Promoter fragment of 51 bp); double stranded BRE51 fragment containing a poly(A) overhang (BREaff); transcription factor (TF); Electrophoretic Mobility-Shift Assays (EMSA); Green Fluorescent Protein (GFP); paramagnetic particles (PMPs); Streptavidin coupled to Paramagnetic Particles (SA-PMPs); matrix-assisted laser-desorption ionization—time of flight (MALDI-TOF MS); Saline Sodium Citrate (SSC.)

Example 1

Materials and Methods

This example describes the materials and methods used to identify the promoter region of the bphA gene, to identify the benzoate response elements, and to identify associated factors.

Identification of the Promoter Region of the bphA Gene

The gene that codes for the enzyme benzoate-para-hydroxylase (BPH) in *Aspergillus niger* was cloned by Van Gorcom et al. (1990) Mol. Gen. Genet. 223, 192-197). The same strain used in developing the present invention by the inventors (# ATCC 1015) was obtained from the American Type Culture Collection (ATCC), and grown in appropriate culture medium (Pontecorvo (1953) Adv. Genet. 5, 141-238); the DNA from these cultured fungi was isolated as described by Yelton et al. ((1984) Proc. Natl. Acad. Sci. USA 81, 1470-1474). Polymerase Chain Reactions (PCR) were carried out to confirm that the strain indeed carried the gene encoding BPH.

Primers were designed in such a way that a PCR amplification product from genomic DNA could be used as an adequate and specific hybridization probe to the bphA gene. The two introns present in the bphA sequence were excluded, and conserved sequences among cytochrome P450-encoding genes were avoided when possible. PCR was performed using Pfu DNA Polymerase, the product was electrophoresed on an agarose gel, and DNA from the corresponding band was purified using the QIAEX II Gel Extraction Kit (Qiagen Inc, Valencia, Calif.), according to the manufacturer's instructions.

This PCR product was cloned into the Bluescript SK vector (Stratagene Cloning Systems, La Jolla, Calif.) and sequenced at the Iowa State University Sequencing Facility, to confirm that it is indeed the bphA sequence published by van Gorcom et al. ((1990) Mol. Gen. Genet. 223, 192-197). The fragment contained within this vector is designated BPH probe.

In order to verify whether this or a similar gene is also present in other organisms, a Southern (DNA) blot was performed containing genomic DNA samples of different fungal and plant species. The fungal species included *Aspergillus niger, Aspergillus nidulans A. nidulans* was used in subsequent studies because a genome sequencing project is currently underway on this species. The representative plant species included: rice (*Oryza sativa*), as an example of a grass species; *Arabidopsis thaliana*, currently a model in plant genetic studies, and with its entire genome sequenced; and tobacco (*Nicotiana tabacum*), for which a benzoate-2-hydroxylase activity was reported a few years ago (León et al. (1993) Plant Physiol., 103: 323-328; León et al (1995) Proc. Natl. Acad. Sci. USA, 92: 10413-10417). For the Southern blot, genomic DNA samples from the species described above were digested with BstEII and XbaI restriction enzymes, separated by electrophoresis on an agarose gel and then transferred to Hybond-N$^+$ nylon membranes (Amersham Life Sci. Inc, Arlington Heights, Ill.). The BPH probe was radiolabeled ($\alpha$-$^{32}$P-dCTP) by means of random priming, using the Amersham's Rediprime II labeling system; the labeled probe was allowed to hybridize to the membrane for at least 12 hours. Transfer and hybridization procedures were carried out as recommended by the manufacturer (Amersham).

The time course gene expression induction was examined by analyzing total RNA at different times after adding benzoic acid. Northern (RNA) blots were carried out using total RNA extracted from mycelia grown for different periods of time in the presence of benzoic acid. Initially, the fungus was inoculated in CM medium (Pontecorvo (1953) Adv. Genet. 5: 141-238) for 24 hours, transferred to benzoate-containing medium (0.1% w/v) for different times, and total RNA was extracted using the Rneasy Plant Total RNA kit (Qiagen Inc, Valencia, Calif.) according to the manufacturer's instructions. Total RNA was resolved on a formaldehyde-agarose gel and transferred to a Hybond-N nylon membrane (Amersham Life Sci. Inc, Arlington Heights, Ill.). Radiolabeled BPH probe was allowed to hybridize to the membrane, as described above. Northern blot methods were also carried out as recommended (Amersham).

Different benzoate concentrations and inducers were used to better characterize the inducibility of the bphA gene. Gene expression was assayed by Northern blots. Benzoate 4-hydroxylase activity is also assessed by enzymatic assays to confirm the inducibility at the transcriptional level described by Van Gorcom et al. ((1990) Mol. Gen. Genet. 223, 192-197). Inducibility is also verified by reverse transcription of mRNAs produced under induction conditions.

Initial attempts to isolate the promoter region of the bphA gene were undertaken by utilizing inverse PCR (IPCR) (Ochman et al. (1988); (1993) Meth. Enzym. 218: 309-321) Genetics 120: 621-623). This technique consists of digesting genomic DNA with several enzymes that cut once within the known sequence, and downstream of the region where the probe binds. A Southern (DNA) blot is carried out to identify the enzymes that produce a fragment with a reasonable size that might contain the promoter region. The genomic DNA is then digested with the selected enzyme, and the resulting fragments are circularized with T4 DNA Ligase under very low DNA concentrations. Specific PCR primers are designed such that amplification extends toward the region of unknown sequence. The PCR product containing the gene and the promoter region is then cloned into a vector. This approach was initially unsuccessful.

In alternative approaches, the BPH promoter is isolated through screening of an *A. niger* genomic library using the BPH probe, and more fine mapped using restriction endonucleases, or by anchored PCR. The latter method was successful.

Promoter deletion studies were also conducted to identify benzoate-responsive boxes within the BPH promoter region.

Promoter Fusions to GFP

In order to determine the minimal promoter length capable of retaining benzoic acid inducibility, promoter fusions to the Green Fluorescent Protein (GFP) gene were prepared. The full bphA promoter and shorter versions of it were PCR amplified using primers BPHPFwd (5'-GCATTG AAGCTTTACATCGGCCTGACG-3', SEQ ID NO:19), BPHFR6 (5'-AAGCCC AAGCTTGAGTAAGTAAGGAGTTGG-3', SEQ ID NO:20), BPH331 (5'-TTTTCC AAGCTTCCGTAACTCTCGCCTC-3', SEQ ID NO:21), and BPHPRev (5'-CCCGTT AAGCTTTTTGAGTTGAAGTGCAGG-3', SEQ ID NO:22). These primers introduced HindIII restriction sites (underlined) at both ends, which allowed cloning of the fragments upstream of the GFP gene contained within the pEBFP vector (Clontech, Palo Alto, Calif.).

The fragment resulting from the amplification with primers BPHPFwd and BPHPRev corresponded to the full bphA promoter, whereas amplification with BPHFR6 and BPHPRev primers resulted in a fragment encompassing base pair –531 to +1, which included FR6 and FR7 mini-fragments. Amplification with primers BPH331 and BPHPRev produced a fragment of the BPH promoter that encompassed base pair –331 to +1, and did not include the previously identified BREF51. The promoter-GFP fusions were called pBPH-1847-GFP, pBPH-531-GFP, and pBPH331-GFP, respectively. The selectable marker Pyr4 gene from *Neurospora crassa*, driven by its own promoter, was used to select putative *A. nidulans* transformed clones. The selectable marker was PCR-amplified from the pBS-Pyr4 vector using primers PyrEcoF (5'-GCAG GAATTCGATCTGCTTCCTCAACC-3', SEQ ID NO:23), and PyrEcoR (5'-CCG GAATTCGATAAGCTTGATGGGGATC-3', SEQ ID NO:24), which introduced EcoRI restriction sites (underlined) on both ends of the product. These sites were used for cloning of the EcoRI-digested product into the pBPH-GFP deletion constructs described above.

Protoplast Preparation

*Aspergillus nidulans* GR5 protoplasts were prepared according to Aramayo and Timberlake ((1993) EMBO J. 12: 2039-2048), with some modifications. In summary, conidia were inoculated on CM plates supplemented with 10 mM uracil and incubated for 2 d at 37° C. Approximately 10$^9$ fresh conidia were aseptically collected from plates and inoculated into 250 mL of liquid CM medium+10 mM uracil. After overnight incubation at 30° C., 150 rpm, mycelia were harvested through a sterile Büchner funnel lined with two layers of Miracloth, and washed twice with Mycelium Wash Solution (0.6 M MgSO$_4$). Washed mycelia were then suspended in 40 mL of freshly prepared Osmotic Media (1.2 M MgSO$_4$, 10 mM sodium phosphate buffer, pH 5.8), containing 40 U β-glucuronidase (Sigma) and 0.4 g Lysing Enzymes from *Trichoderma harzianum* (Sigma), and incubated for approximately 3 h at 28° C., 120 rpm. The resulting protoplasts were filtered through a Büchner funnel lined with three sheets of sterile Miracloth into a 50 mL conical centrifuge tube, and one volume of ice-cold STC50 solution (1.2 M sorbitol, 10 mM CaCl$_2$, 50 mM Tris-HCl, pH 7.5) was added. Protoplasts were collected by centrifugation at 2,000×g for 10 min, at 4° C. A second wash was performed by suspending the pelleted protoplasts in 1 mL of STC50 and centrifuging again as described above. Concentration of protoplasts was determined using a hemacytometer, and adjusted to 10$^8$ protoplasts per mL.

Protoplast Transformation

The procedure described by Rolf Prade, Oklahoma State University, on the Web Site (microbiology.okstate.edu/faculty/prade/) was used for introduction of plasmid DNA into *A.* nidulans GR5 protoplasts. Briefly, approximately 10 μg of plasmid DNA dissolved in 10 mM Tris-HCl (pH 8.0) were added to 100 μL protoplasts (approx. $10^7$ protoplasts), and the mixture was incubated on ice for 10 min. Next, 250 μL of freshly prepared 60% PEG 3350 (Sigma) in STC50 were added, and incubation was carried out at 37° C. for an additional 20 min. After addition of 2 mL STC50 containing 1% glucose and gently mixing, protoplasts were plated onto molten minimal medium, containing 1.2 M sorbitol, and incubated at 37° C. until uracil auxotrophic colonies became visible.

Identification of Benzoate Inducible Transcription Factors and Genes Encoding Them Promoter activity is usually modulated by protein factors that bind to the DNA and either activate or repress transcription. Thus, as necessary, proteins (transcription factors) that bind to the promoter and regulate transcription of the bphA gene are also identified. These experiments utilize gel-shift assays as described by Singh et al. ((1986) Nature 319: 154-158). In order to investigate whether any proteins bind to the bphA promoter, EMSAs were carried out in the presence of total protein extracts from *A. niger* mycelia. This assay is based on the fact that free double-stranded DNA fragments will run faster on a native polyacrylamide gel than those that have proteins associated to them. The association results in a shift in the mobility of the DNA fragment on the gel.

Genes that code for proteins involved in the regulation of the BPH promoter are cloned as well. Benzoate-inducibility of the transcription factor is tested.

Total Protein Extraction.

Total protein extracts were prepared from both benzoate-induced and uninduced *A. niger* mycelia according to the procedure described by Peters and Caddick (1994) Nucl. Acids. Res. 22, 5164-517), with a few modifications. Briefly, mycelia were ground in liquid $N_2$ and the resulting powder was suspended in Extraction Buffer (20 mM HEPES-KOH [pH 7.9], 100 mM KCl, 0.2 mM EDTA, 20% glycerol, 2 mM DTT, protease inhibitor cock-tail (Sigma cat# P2714) (5 ml/g of tissue). Saturated ammonium sulfate solution (pH 7.0) was added to the lysate to a final concentration of 0.4 M. After stirring for 15 min, the solution was allowed to stand for another 15 min. Cell debris and chromosomal DNA were removed by centrifugation at 100,000×g, 4° C., for 30 min, and solid ammonium sulfate was added to the supernatant over a period of 90 min, to 70% saturation, while stirring gently. Again, the lysate was allowed to stand for a further 30 min, and precipitated proteins were pelleted by centrifugation at 10,000×g, 4° C., for 30 min. The pellet was resuspended in Binding Buffer (10 mM Tris-HCl pH 7.5, 50 mM NaCl, 0.5 mM DTT, poly [dI-dC]), and the solution was dialyzed overnight against the sane Binding Buffer. Protein concentration was determined by the Bradford method (Bio-Rad), and bovine serum albumin (BSA) was used as a standard.

Electrophoretic Mobility Shift Assays (EMSA).

Promoter activity is usually modulated by protein factors that bind to the DNA and either activate or repress transcription. In order to investigate whether any proteins bind to the bphA promoter, EMSAs were carried out in the presence of total protein extracts from *A. niger* mycelia. This assay is based on the fact that free double-stranded DNA fragments will run faster on a native polyacrylamide gel than those that have proteins associated to them. The association results in a shift in the mobility of the DNA fragment on the gel.

The BandShift Kit (Pharmacia Biotech, Piscataway, N.J.) was used for this purpose. DNA mini-fragments from the bphA gene promoter region were prepared by means of PCR, separated on a 0.8% agarose gel, and purified using the QIAEX II Gel Extraction Kit (Qiagen, Valencia, Calif.). Approximately 100 ng of each mini-fragment were [$g^{32}P$] dATP-labeled using T4 polynucleotide kinase enzyme, purified through a Sephadex G-25 column, and mixed with 1 mg of total protein extract, along with 5% glycerol, 0.05% NP-40, 1 mg Poly(dI-dC)-Poly(dI-dC), 10 mM Tris-HCl (pH 7.5), 50 mM NaCl, and 0.5 mM DTT. This mixture was incubated for 1 to 3 h at room temperature, and then electrophoresed on 5% polyacrylamide gels under non-denaturing conditions. DNA mobility shifts were visualized after exposing the gels to an X-ray film.

Purification of putative transcription factors. Transcription factors are purified by one of two approaches, affinity chromatography and/or a molecular approach.

1. Affinity Chromatography

In one approach, putative transcription factors are purified using BRE51 fragment as "bait" for affinity chromatography:

Poly(A) tail method. Sense and anti-sense strands, corresponding to the BRE51 fragment sequence, were synthesized at IDT DNA Technologies with a 3' poly(A) overhang. Both strands were annealed by mixing 1 mg of each together in 100 ml of 50 mM NaCl and heating the mixture to 70° C. for 5 min, then slowly cooling it down to room temperature for at least 30 min. After electrophoresing the annealed fragment on a 2% Low Melting Point Agarose gel, the desired double-stranded fragment was purified from the gel using the QIAEXII Gel Purification Kit (Qiagen, Valencia, Calif.) according to the manufacturer instructions. The double stranded BRE51 fragment, containing the poly(A) overhang was then called BREaff.

Approximately 1 mg of BREaff was annealed at room temperature to a Biotinylated-Oligo(dT) probe (PolyATract® mRNA Isolation System, Promega, Madison, Wis.), and the mixture was added to a tube containing Streptavidin coupled to Paramagnetic Particles (SA-PMPs) in 0.5×SSC (1× is 150 mM NaCl, 15 mM $Na_3$citrate). After washing the particles once with 0.1×SSC, and twice with 1× Binding Buffer (10 mM Tris-HCl pH 7.5, 50 mM NaCl, 0.5 mM DTT, poly [dI-dC]), 10 mg of benzoate-induced total protein extracts were added and the reaction was incubated at room temperature for 2 h. After two washes with 1× Binding Buffer (without poly[dI-dC]), BREaff bound to proteins was eluted from SA-PMPs with 100 ml of water. Eluted proteins were separated on 12% SDS-PAGE and visualized by Coomassie blue staining.

Biotin labeling method. An alternative approach to the affinity chromatography described above was devised by labeling BRE with Biotin. Briefly, BRE51 was PCR-amplified and an EcoRI restriction site was added at the 5' side. After EcoRI digestion of the product, the overhang was filled in by *E. coli* DNA Polymerase Klenow fragment (New England BioLabs) at 25° C., for 15 min, in the presence of 33 mM each of dCTP, dGTP, dTTP, and Biotin-7-dATP (Gibco BRL). Biotinylated BRE51 was purified with QIAEX II Gel Extraction kit (Qiagen, Valencia, Calif.), and added to the streptavidin-coupled paramagnetic particles, as described above. Washes and incubation with total proteins were carried out exactly as described above, but bound proteins were eluted from SA-PMPs with binding buffer containing 1 M NaCl.

2. Molecular Approach for the Isolation of the Transcription Factor Gene: Activation Domain-cDNA Library Construction Total RNA was extracted from *A. niger* cells grown in the presence of benzoic acid for 5 h by using the RNAeasy kit (Qiagen), following the instructions of the manufacturer. Ten µg of total RNA were used to isolate poly A+ RNA, using the PolyATtract kit (Promega, Madison, Wis.), also according to the instructions provided. Complementary DNAs (cDNAs) were synthesized using the Matchmaker Library Construction and Screening Kit (Clontech, Palo Alto, Calif.), which employs the SMART™ technology. First strand cDNAs were synthesized at 42° C. for 10 mm, from approximately 1 µg of poly A+ RNA, using 1 µM Oligo d(T) primer (CDSIII, 5'-ATCTAGAGGCCGAGGCGGCCGACATG-d(T)$_{30}$VN-3') (SEQ ID NO:38) and MMLV Reverse Transcriptase. One µM SmartIII™ oligonucleotide (5'-AAGCAGTGGTATCAA CGCAGAGTGGCCATTATGGCCGGG-3', SEQ ID NO:25) was added, and was the reaction incubated at 42° C. for an additional 1 h. After removing DNA-RNA double strands with RNAse H, double stranded cDNAs were amplified by Long Distance-PCR (LD-PCR). Thermocycler cycles consisted of incubation at 95° C. for 30 sec, followed by 20 cycles, each consisting of denaturation at 95° C. for 30 sec and combined annealing and extension at 68° C. for 6 mm. Extension time increased by 5 sec each cycle. PCR-amplified ds cDNAs were purified through a Chroma Spin+TE400 size exclusion column.

The library was constructed by in vivo recombination of cDNAs in yeast. Competent yeast cells strain AH109 were prepared and transformed with the purified ds cDNAs and SmaI-linearized pGADT7-Rec vector. In vivo recombination yields a complete GAL4 activation domain vector. Transformants were selected on SD/-Leu media.

Yeast One-Hybrid Screen

A reporter construct was prepared by introducing three tandem copies of the previously identified BREF51 immediately upstream of a minimal promoter in vector pHISi-1 (Clontech, Palo Alto, Calif.). Tandem copies of BREF51 were first assembled in a pBluescript SK (−) vector. BREF51 was PCR-amplified using primers BREBP (5'-TAT GGATCCCTGCAG, ACTAGTCACAAGTTAC-3', SEQ ID NO:26) and BREBN (5'-TAT GGATCCATGCATGATCTTCATGACTAATGATG-3', SEQ ID NO:27), which introduced BamHI and PstI restriction sites at the 5' end (underlined on BREBP), as well as BamHI and NsiI sites at the 3' end (underlined on BREBN). After cloning the amplified BREF51 into pBluescript (named pBSF51), one aliquot of this plasmid was digested with NsiI and AflIII enzymes, and another aliquot with PstI and AflIII enzymes, the two complementary fragments were ligated to each other, reconstructing a complete vector containing 2 copies of BREF51, which was called pBSF102. This procedure was iterated, this time using pBSF102 as one of the aliquots. The final vector containing 3 copies of BREF51 was then called pBSF153. The 3 tandem copies of BREF51 were then sub-cloned to pHisi-1 vector using EcoRI and XbaI restriction sites. The resulting chimeric promoter in pHisi-1 controls expression of the HIS3 gene from yeast, which encodes the enzyme imidazole glycerol-phosphate dehydratase. This vector was then called pHISi-1.153, and was integrated into the chromosome of yeast strain YM4271 by first linearizing and then transforming into competent cells following the small-scale LiAc transformation procedure (Ito et al. (1983) J. Bacteriol. 153: 163-168) to produce the reporter strain YM4271HIS. Leaky expression from the chimeric promoter allowed selection of clones containing the integrated vector. To control leakiness of the promoter during the one-hybrid screen, 30 mM 3-AT were added to the culture media. This concentration has been shown in a concentration curve experiment to completely abolish growth of the reporter strain in the absence of histidine (data not shown).

Plasmid DNA isolated from approximately $1\times10^6$ AD-cDNA library colonies were transformed into YM4271HIS following the procedures described by Gietz et al. ((1992) Nucl. Acids Res. 20: 1425). Briefly, an overnight-grown culture of YM4271HIS (OD$_{600}$=0.5) was centrifuged for 5 min at 1000×g, and resuspended in TE buffer (10 mM Tris.HCl, pH 8.0, 1 mM EDTA). After another centrifugation step as described above, competent cells were resuspended in freshly prepared 1× TE/LiAc. In a sterile tube, 20 µg of AD-cDNA library plasmid were mixed with 2 mg of herring testes carrier DNA, before 1 mL of competent cells were added and mixed. Six mL of sterile PEG/LiAc were added to the transformation mixture, mixed by vortexing, and incubated at 30° C. for 30 min with shaking at 200 rpm. DMSO was added (700 µL), mixed by inversion, and cells were heat-shocked for 15 min at 42° C. After chilling on ice for 2 min, the mixture was centrifuged for 5 min at 1000×g, at ambient temperature, and resuspended in TE buffer to a total of 7.5 mL. The transformation mixture was plated on 150×15 mm Petri dishes (500 µL/plate) containing SD/-Leu/-His media supplemented with 30 mM 3-AT, to select for clones displaying DNA-protein interaction. Plates were incubated at 30° C. until colonies were visible.

Plasmid Purification from Positive Clones

Plasmid DNA was purified from positive clones selected on the one-hybrid screen by using Clontech's Yeast Plasmid Isolation Kit. Liquid cultures grown overnight at 30° C. were centrifuged and the supernatant was resuspended in 50 µL of 67 mM KPO$_4$ buffer (pH 7.5). Fifty units of Lyticase were added and the mixture incubated at 37° C. for 60 min. After 10 µL of 20% SDS were added and the tubes vortexed vigorously for 1 min, plasmid DNA was purified using Chroma Spin-1000 DEPC-H$_2$O columns (BD Biosciences, Palo Alto, Calif.).

cDNA Insert Size Determination

PCR amplifications using primers specific for the pGADT7-Rec vector (GADF: 5'-CTATTCGATGATGAA-GATACCCCACC-3", SEQ ID NO:28, and GADR: 5'-GT-GAACTTGCGGGGTTTTTCAG-3', SEQ ID NO:29) were carried out with the objective of determining the size of the cDNA insert. PCR conditions were as follows: denaturation at 94° C. for 5 min, followed by 25 cycles, each consisting of denaturation at 94° C. for 1 min, annealing at 56° C. for 45 sec, and extension at 72° C. for 1 min. One final cycle of extension at 72° C. for 10 min was also used. Amplified products were separated on a 0.8% agarose gel containing EtBr, and the bands visualized under UV light.

*E. coli* Transformation of Yeast Plasmids

To obtain enough plasmid DNA for sequencing, 5-10 µL of yeast plasmid DNA isolated from one-hybrid positive clones were transformed into *E. coli* XL1-Blue competent cells by electroporation in 1 mm-gap cuvettes, and using standard procedures (Sambrook et al. (1989) Molecular Cloning: A Laboratory Manual, 2$^{nd}$ ed., Cold Spring Harbor (N.Y.) Laboratory Press, Vol. 1). Plasmid DNA was isolated from bacterial cells using the Quantum Prep Plasmid Mini Prep kit (Bio-Rad, Hercules, Calif.), according to the instructions provided by the manufacturer.

cDNA Sequencing cDNA inserts that yielded at least one product when amplified by PCR were submitted for sequencing at the Low Throughput Sequencing Center, at the Purdue University Genomics facility. DNA sequence was obtained from the 5' end of the cDNAs using the GADF primer. When necessary, sequence from the 3' end was also obtained using primer GADR. The nucleic acid sequence for GAD1 (SEQ ID NO: 16) is shown in FIG. 16, the nucleic acid sequence for GAD11 (SEQ ID NO:18) is shown in FIG. 17, the nucleic acid sequence for a GAD1 homolog (SEQ ID NO:35) is shown in FIG. 18, and the nucleic acid sequence for a GAD11 homolog (SEQ ID NO:37) is shown in FIG. 19.

Total Protein Extraction from Yeast

Positive clones identified on the one-hybrid screen were grown in 100 mL of SD/-Leu media, and total proteins were extracted following a modified procedure from that described by Arndt et al. ((1987) Science 237: 874-880). All extraction steps were performed at 4° C. Briefly, cells were pelleted by centrifugation at 1000×g for 5 min, and resuspended in 400 µL of protein extraction buffer (0.1 M Tris.HCl pH 7.5, 0.2 M NaCl, 0.01 M β-mercaptoethanol, 20% glycerol, 5 mM EDTA, 1 mM PMSF). Glass beads (425-600 microns in diameter) were added and tubes were vortexed vigorously for 10 min in a Geno/Grinder 2000 (SPEX CertiPrep, Metuchen, N.J.). The glass beads were allowed to settle, and the supernatant was transferred to a new tube. New glass beads and 200 µL of the same protein extraction buffer were added, and the tubes were vortexed again as described. Protein concentration of the resulting supernatant was determined by the Bradford method (Bio-Rad, Hercules, Calif.), and BSA was used as a standard.

Reverse Transcription PCR

Total RNA was extracted from uninduced and benzoic acid-induced *A. niger* mycelia as described earlier, and approximately 1 µg was used to synthesize first strand cDNAs with the SuperScript First-strand Synthesis System for RT-PCR (Invitrogen, Carlsbad, Calif.). The reaction was carried out in the presence of 0.5 µg of an oligo(dT) primer, 0.5 mM dNTP mix, 5 mM $MgCl_2$, 10 mM DTT, 1× RT buffer (20 mM Tris.HCl pH 8.4, 50 mM KCl), RNAseOUT™ RNAse inhibitor, and 50 U of SuperScript™ II Reverse Transcriptase. Tubes were incubated at 42° C. for 50 min, after which the reaction was terminated at 70° C. for 15 min. RNAse H was added, and tubes were incubated for an additional 20 min at 37° C. Double-stranded cDNAs were amplified by PCR using Red Taq DNA Polymerase (Sigma-Aldrich, St. Louis, Mo.), dNTP's, and gene specific primers: GAD1F (5'-CACATA-CACAATGGTCTCCTTCAAG-3', SEQ ID NO:30), GAD1R (5'-CTGCACACATGTAATACGCATACC-3', SEQ ID NO:31), GAD11F (5'-GGTTTAGCCTTCACTCT-CAAGGATC-3', SEQ ID NO:32), and GAD11R (5'-GTC-GAAAGGTGCGATTCGATATAGG-3', SEQ ID NO:33). PCR amplification consisted of a denaturation step at 94° C. for 5 min, followed by 30 cycles, each of denaturation at 94° C. for 45 sec, annealing at 56° C. for 30 sec, and extension at 72° C. for 1 min. A final extension step at 72° C. for 10 min was also included. Amplified cDNAs were separated on a 0.8% agarose gel containing EtBr, and bands were visualized under UV light.

Construction of a Benzoate Inducible Hybrid Promoter

A chemically-induced promoter (hybrid promoter) is constructed by placing benzoate-response elements within plant regulatory regions, to make it functional in plants.

A chemically inducible promoter is constructed by placing single or multiple copies of BREF51, or functionally effective fragments or modifications thereof, upstream of a minimal plant gene promoter containing a TATA box transcription start signal, to make the benzoate response element functional in cells; the product is referred to as a benzoate inducible hybrid promoter. In some embodiments, additional plant gene promoter elements may be placed around the BREF51, or functionally effective fragments or modifications thereof, to achieve a host cell-specific temporal or spatial expression in response to the chemical application.

This hybrid promoter is fused to a reporter gene, such as GUS (Jefferson et al., (1987) EMBO J. 6: 3901-3907) or GFP (Haseloff et al. (1997) Proc. Natl. Acad. Sci. USA 94: 2122-2127), and transformed into *Arabidopsis thaliana* by *Agrobacterium*-mediated transformation as described by Ye et al. ((1999) Plant J. 19: 249-257). Another plasmid containing the gene that codes for the transcription factor is introduced into these plants as well, if necessary. The transgenic plants obtained are assayed for the inducibility of expression of the reporter gene. Northern blots are carried out to verify both the background and the induced levels of expression of the reporter gene in the plant, under different concentrations of the inducer. The effects, if any, of the inducible system on the overall performance of the plants are also evaluated. Evaluated characteristics include but are not limited to pathogen or insect resistance, whole plant and tissue organization, flowering time, or any other signs of toxicity.

Example 2

Characterization of Benzoate Response Elements, Promoters, and Transcription Factors This example describes results of the development of the present invention, and includes characterization of the bphA gene expression, identification and isolation of bphA gene promoter and response element, and identification of transcription factors Characterization of bphA Gene Expression In order to verify whether this or a similar gene is also present in other organisms, a Southern (DNA) blot was performed containing genomic DNA samples of different fungal and plant species. A genomic DNA blot from samples of *Aspergillus niger, A. nidulans*, tobacco, rice and *Arabidopsis* was probed with $\alpha$-$^{32}$P-dCTP-labeled BPH probe; the results are shown in FIG. 2. As expected, a band of 1100 base pairs was labeled by the BPH probe after restriction digestion with the BstEII enzyme. *Aspergillus nidulans* also seems to contain a similar gene in its genome, as shown by the >12 kbp band produced. The coding region of the bphA gene does not contain any restriction sites for the XbaI enzyme and therefore is a good way of determining the number of copies of this gene in the genome. Cleavage of genomic DNA with a restriction enzymes can be expected to fragment different genes at different places to give a range of sizes. Use of several enzymes confirms the number of independent genes. However, some enzymes will cut within the coding region to yield two fragments instead of one. In instances where a single band is observed after cutting with several enzymes, then one can be reasonably confident there is only one copy of the gene (in other words, no homologue). The results indicate that both fungi have only one copy of the gene. None of the plant species used in this experiment appeared to contain a gene similar in nucleic acid sequence to the bphA gene.

To verify the inducibility of the bphA gene by benzoic acid, *A. niger* was inoculated in complete medium and grown for 24 hours before being transferred to fresh medium containing 0.1% benzoic acid. Mycelia were harvested after different periods of induction, and total RNA was extracted. A preliminary RNA blot showed that the bphA gene is induced at the transcriptional level within ten minutes by benzoic acid (FIG. 3).

Concentration curves indicate that benzoic acid concentrations as low as 0.8 mM induce transcription of the bphA gene. Other compounds which can induce the promoter include sodium benzoate and methyl benzoate; however, benzyl alcohol and hydrocinnamic acid do not induce the promoter (FIG. 4).

Identification and Isolation of bphA Gene Promoter and Response Element

Using Anchored Polymerase Chain Reactions (PCR) (Siebert et al. (1995) Nucl. Acids Res. 23: 1087-1088), about 1.8 kb of the promoter region of the *Aspergillus niger* bphA gene was isolated, and then cloned into pBluescript SK⁻. The sequence of the 1.8 kb of the promoter region of the *Aspergillus niger* bphA gene (SEQ ID NO:1) is shown in FIG. 1.

Figure 8:
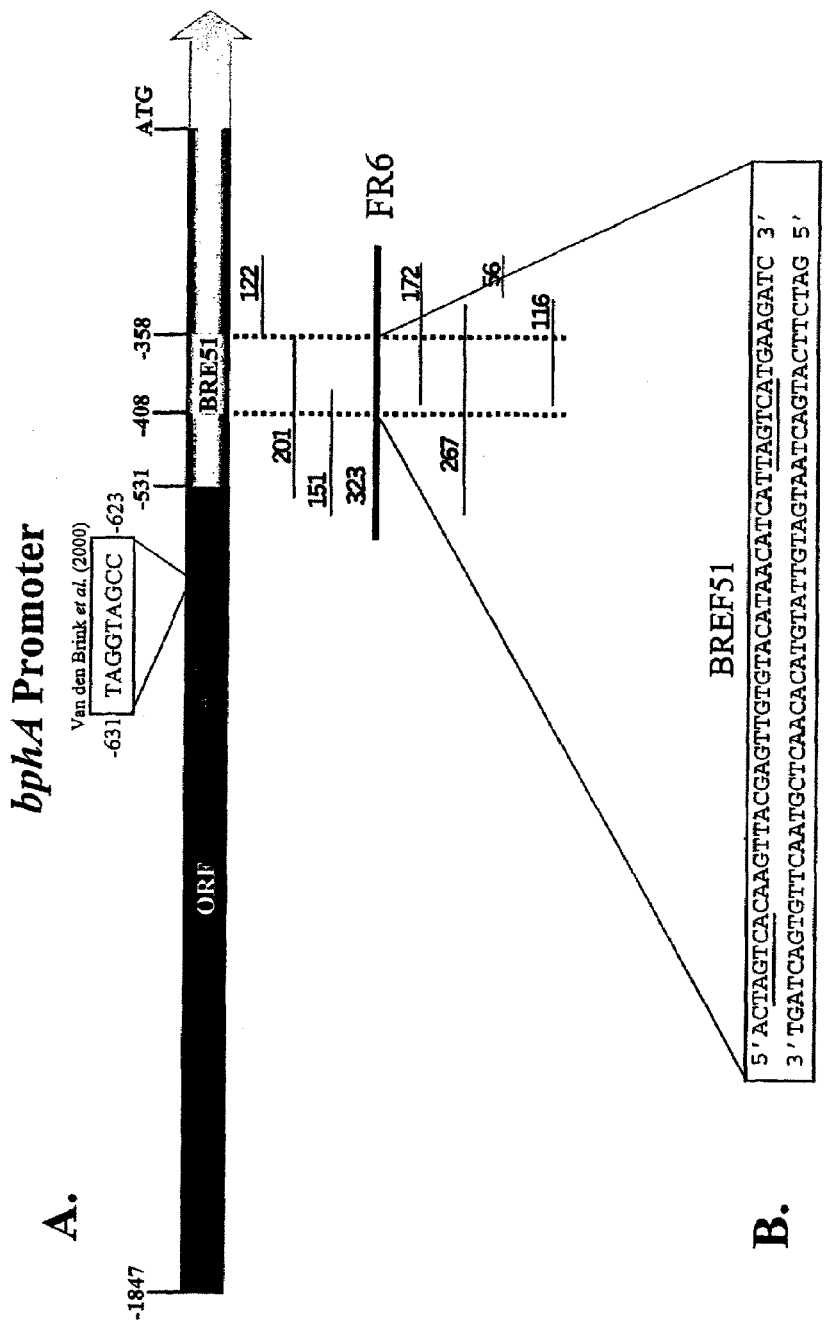
FIG. 8 shows, in panel A, the bphA promoter region that was tested for promoter activity. This region comprises the 1847 nucleotides upstream from the start sequence of the bphA gene (the bphA gene was published by van Gorcom et al., Mol. Gen. Genet., 223:192-197, 2000; and is Genebank accession No. X52521). Subsequently, it was discovered that much of this putative promoter sequence actually comprises an open reading flame of an unidentified protein. A response element was initially identified by van den Brink et al. ((2000) Mol. Gen. Genet. 263: 601-609) based upon a consensus sequence between *A. niger* and *A nidulans*. The identification of the response element by van den Brink et al. (2000) Mol. Gen. Genet. 263: 601-609) is determined to be erroneous, as it is now known that this initially identified response element is located in the open reading frame of the putative promoter sequence (from positions −532 to −1847); *A. nidulans* also contains this open-reading flame sequence in the putative promoter sequence of the bphA gene. The entire 1847 bp suspected promoter region, and fragments thereof generated by PCR, were tested for electrophoretic mobility shift activity (as described in FIGS. 5 and 6), and 0.4 kb Fragment 6 (FR6) was the only fragment of the suspected promoter to exhibit shift activity. FR6 was fragmented further and only fragments containing a 51 bp sequence (as shown in panel B, SEQ ID NO:4) demonstrated EMSA shift activity (as described in FIG. 7). This fragment alone was one of the smallest fragment shown able to exhibit an electrophoretic mobility shift, indicating the attachment of a transcription factor in vitro. Analysis of this sequence revealed a pair of 6 bp repeat sequences subsequently shown to be the suspected Benzoate Response Element (BRE6); the sequence TAGTCA (SEQ ID NO:5). At least one of these putative BREs is contemplated as necessary and sufficient for activity (e.g. the one on the right in panel B). The 51 bp sequence (SEQ ID NO:4) is designated as BRE-containing fragment (BREF51).

In order to investigate whether protein factors are involved in controlling the initiation of transcription from the bphA gene promoter, seven mini-promoter fragments were created by PCR (FIG. 5), ranging in size from 247 bp to 324 bp. These fragments were then radioactive-labeled with $^{32}$P-dATP, and used in Electrophoretic Mobility-Shift Assays (EMSA). After confirming that one of these fragments (FR6, 323 bp) was bound by protein factors (FIG. 6), partially overlapping subfragments encompassing the FR6 fragment were prepared, and again used in EMSA. These assays showed that a 51-bp fragment located 350 bp upstream of the transcription start point is consistently bound by a protein factor that is present in total protein extracts from benzoate-induced *A. niger* mycelia (FIG. 7). The most significant feature of this BRE sequence (shown in FIG. 8) is the presence of a pair of 6-bp direct repeats of the potential BRE (underlined in FIG. 8).

bphA gene promoter fusions to the Green Fluorescent Protein (GFP) gene were constructed and transformed into *Aspergillus nidulans* strain GR5 (ATCC # 200171). Both the full promoter (1.8 kbp) and a short version containing fragment 6 and the TATA box (FR6, 0.4 kbp) were placed in front of the GFP coding region (pEBFP, Clontech, Palo Alto, Calif.). Transformants were screened by PCR for the presence of the GFP gene, and grown either in the presence or in the absence of 8 mM benzoic acid. After 5 hours of induction, both promoters were able to induce GFP expression only in the presence of the inducer benzoate (FIG. 8).

Identification of Transcription Factors

Initial efforts to isolate trans-acting factor(s) involved in the regulation of the bphA gene promoter utilized affinity chromatography experiments using either the BRE51 or benzoic acid as affinity ligands. In a first approach, BRE was biotinylated, purified, and allowed to bind to streptavidin-linked paramagnetic particles (PMPs; PolyATtract mRNA Isolation Kit, Promega, Madison, Wis.). Total protein extract from benzoate-induced *A. niger* was added to the solution, incubated for 60 min, and the PMPs were washed several times. Bound proteins were then eluted from the PMPs under high salt conditions. The fractions were electrophoresed on SDS-PAGE, and a protein of approximately 45 kDa could be observed (FIG. 10); however, this factor failed to cause a shift on the mobility of BRE51 when used on EMSA. In a second approach, benzoic acid, immobilized on 4% cross-linked beaded agarose (Sigma, St. Louis, Mo.) was used as the affinity ligand. Again, total protein extract from benzoate-induced *A. niger* was added, the column was washed, and bound proteins eluted under high salt conditions. The eluted fraction also failed to cause mobility shifts on labeled BRE51 when used on EMSA.

Calculation of the stoichiometry of the amount of binding of a protein element that saturates the amount of BREF51 in the EMSA indicates that a minimum of 6 fmoles are present per mg of protein extract. If the factor is about 50 kDa, then this amount represents 300 pg of factor. Thus, a manageable scale-up of about 100-fold is necessary to bind 30 ng of factor needed to detect tryptic fragments by MALDI-TOF MS.

The hypothesis of a surface receptor was tested by using the p-NH$_2$-benzoate coupled to agarose (as described above) as a non-cleavable external probe. Fungal protoplasts containing the BRE fused to GFP were then prepared, and activation of the BRE (production of the GFP marker) by addition of the agarose-immobilized benzoate derivative to the fungal protoplasts was scored. Whereas the benzoate or p-aminobenzoate induced GFP fluorescence in the BRE-GFP transformed line, no fluorescence was observed when p-nitrobenzoate was linked to the agarose beads. This initial set of results indicates that the TF is a soluble factor. In order to investigate whether the disparity of size between the larger agarose beads and fungal protoplasts may have caused steric problems in binding of the inducer, smaller ligands still incapable of uptake are constructed and utilized to confirm a non-membrane surface location.

The yeast one-hybrid system screen yielded 17 colonies on SD/-Leu/-His media. DNA sequences obtained from the plasmids isolated from the bacterial cells were translated and compared by BLASTp search (Table 1). Total proteins were isolated from 9 yeast clones which cDNAs encoded proteins that did not show significant similarities to any gene of known function in the databases. Protein extracts from each of these yeast clones were used in EMSA to eliminate those cDNAs that encode proteins that do not interact with BREF51. Yeast clones GAD1 (FIG. 16) and GAD11 (FIG. 17) both showed a gel mobility shift of the BREF51 fragment in these assays (FIG. 13). The shift in mobility displayed by GAD1 was similar to that observed with *A. niger* total protein extracts. The protein encoded by GAD1 is highly similar to a predicted protein present in the *A. nidulans* genome (E value 2e-83, see FIG. 18), and similar to a hypothetical protein (B24P11.210) in the *N. crassa* genome (E value 4e-27) (Table 2). GAD1 protein is rich in serine residues (16%), and is predicted by PSORTII to be localized in the nucleus (70.6% probability). It also shows high similarity to a hypothetical serine-rich protein (C13G6.10c) from *S. pombe*. Serine-rich motifs can be phosphorylation targets by protein kinase C in proteins. Also, serine-rich regions have been shown to be part of the transactivation domains of some transcription factors in both mammalian and viral cells. While not necessary to understand or practice the present invention, if GAD1 is involved in the regulation of BPHprom, GAD1 protein might be always bound to a benzoic acid response element in the bphA promoter. In the absence of benzoic acid GAD1 would be inactive, unable to promote transcription. However, addition of benzoic acid could cause phosphorylation of one of the serine residues in GAD1, leading to its activation. This mode of regulation is analogous to that of the transcription factor CREB, which is involved in responses to cAMP in human cells (Latchman 1997).

GAD11 protein (SEQ ID NO:17; FIG. 17) is weakly similar to a *Drosophila melanogaster* homeotic gene regulator, and also to a putative nuclear protein family member from the nematode *C. elegans*. It is also predicted by PSORTII to be localized in the nucleus (94.1% probability). GAD11 was also predicted to have a coiled-coil region consisting of 37 amino acid residues (Lupa's algorithm). The α-helical coiled coil is a structural motif found in many proteins. It consists of two long α-helices with a repeating pattern of hydrophobic side chains that interlock to produce a supercoiled structure. The most important function of coiled-coil regions in myosins and kinesins is for dimerization. Because the coiled coil may be rigid and extended in solution it can act as a spacer or connector between protein domains. This may explain the larger shift in BREF51 mobility in the presence of GAD11 protein extract, since GAD11 proteins may be forming homodimers connected by the coiled-coil region. GAD11 has a homolog in *A. nidulans* (E value 6e-29, See FIG. 19), but no homologs in *N. crassa* were found.

Reverse Transcription PCR (RT-PCR) experiments revealed that while GAD1 is expressed constitutively, GAD11 is slightly downregulated in the presence of 8 mM benzoic acid for 5 h (FIG. 14). While not necessary to understand or practice the present invention, if in fact either GAD1 or GAD11 are involved in regulation of the bphA promoter, constitutive transcription of GAD1 does not rule out the possibility that the activity of the GAD1 protein is modulated by benzoic acid. On the other hand, downregulation of the GAD11 gene in the presence of benzoic acid indicates that the protein may function as a transcriptional repressor of the bphA promoter. GAD1 is constitutively expressed, while GAD11 seems to be downregulated in the presence of benzoic acid in the media. There is a possibility that protein-protein interactions play a role in the regulation of this gene in *A. niger*.

Example 3

Chemical Induction of Flowering in a Model System

The ability of a chemically controllable promoter to induce flowering was tested in *Arabidopsis* containing a disabled FT gene. The ft-3 mutant *Arabidopsis*, which is caused by missense mutation deleting the entire C-terminal region of the protein and displays a significant delay in the flowering response, was obtained from the *Arabidopsis* Stock Center (Ohio State Univ).

A chemically inducible promoter available to test induction of flowering is the glucocorticoid receptor-promoter element system that is induced by the glucocorticoid, dexamethasone (Aoyama and Chua (1997) Plant J. 11: 605-612; Kunkel et al. (1999) Nature Biotech. 17: 916-919). This system has recently been engineered to avoid some leakiness problems originally experienced, and the plasmid constructs for the two necessary components have been obtained. The general strategy of the glucocorticoid receptor promoter was described by Aoyama and Chua ((1997) Plant J. 11, 605-612). Dr. Jen Sheen (Massachusetts General hospital) restructured the glucocorticoid promoter to be LexA-based instead of Gal4, and this provided a finer control. This promoter can be assembled from available sequences by one skilled in the art.

Wild-type FT cDNA was obtained from Dr. Detlef Weigel (formerly of the Salk Institute, La Jolla, Calif., and now Max Planck Institute for Developmental Biology, Tübingen, Germany); the wild-type FT cDNA was prepared from transcripts for flowering *Arabidopsis* plants. This and other *Arabidopsis* cDNAs are available from Dr. Weigel or from a publicly accessible Riken BioResource Center, Japan (See Riken Web site). As the *Arabidopsis* genome is completely sequenced and publicly available, one skilled in the art can design primers and obtain a full-length FT gene by RT-PCR. Wild-type FT cDNA was placed under the control of the LexA-based glucocorticoid inducible promoter (called Lex-FT), and this construct was subcloned into the pCAMBIA 1305.1 binary vector (CAMBIA, Canberra, Australia). In a separate construct, the hybrid transactivating factor LSVG, under a constitutively expressed promoter, was cloned into pCAMBIA 1302 (CAMBIA, Canberra, Australia). Both vectors were then transformed by vacuum infiltration (Clough and Bent (1998) Plant J. 16: 735-743) into the *Arabidopsis* ft plants. T1 seeds were harvested, and plated out on selective media, containing the antibiotic hygromycin, in order to recover putative transformants.

The selected transformants have been assayed for GUS or GFP expression (depending on the pCAMBIA vector used), and the presence of the inducible promoter system and the FT gene have been confirmed by PCR. A problem was encountered with the plants containing the pCAMBIA 1302-LSVG constitutive-expressant construct, probably due to a slow accumulation of toxic levels the hybrid transacting factor LSVG during the prolonged growth before flowering. The transgenic plants died shortly after flowering, yielding few or no seeds from the plants. To overcome this unexpected difficulty with this test system, the LSVG hybrid transactivator was subcloned into a different pCAMBIA vector, with a kanamycin selectable marker instead of hygromycin. Confirmed Lex-FT homozygous plants are transformed with the new construct. This approach provides not only a faster way of incorporating both components into the same plant, but also overcomes the toxicity problem by spraying the test plants after only one-third the growth period.

As described above, the Lex-FT construct has been successfully integrated into non-leaky ft homozygous mutants; these plants are then transformed with the altered construct containing a constitutively expressed LSVG in a binary vector with kanamycin resistance.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

We claim:

1. A recombinant plant expression vector comprising:
   a) a benzoate inducible promoter comprising a benzoate response element comprising a fragment of SEQ ID NO:1 comprising SEQ ID NO:4 operably linked to a promoter functional in a plant, and
   b) a nucleic acid sequence of interest, wherein said nucleic acid sequence of interest is operably linked to said benzoate inducible promoter.

2. The recombinant plant expression vector of claim 1, wherein said promoter comprises a plant minimal gene promoter.

3. The recombinant plant expression vector of claim 1, wherein said promoter is 35S.

4. The recombinant plant expression vector of claim 1, wherein the fragment of SEQ ID NO:1 comprising SEQ ID NO:4 is SEQ ID NO:1, SEQ ID NO:2, SEQ ID NO:3, SEQ ID NO:4, or SEQ ID NO:6.

5. A transgenic plant cell comprising:
   a) a benzoate inducible promoter comprising a benzoate response element comprising a fragment of SEQ ID NO:1 comprising SEQ ID NO:4 operably linked to a promoter functional in a plant, and
   b) a nucleic acid sequence of interest, wherein said nucleic acid sequence of interest is operably linked to said benzoate inducible promoter.

6. The transgenic plant cell of claim 5, wherein said promoter comprises a plant minimal gene promoter.

7. The transgenic plant cell of claim 5, wherein said promoter is 35S.

8. The transgenic plant cell of claim 5, wherein the fragment of SEQ ID NO:1 comprising SEQ ID NO:4 is SEQ ID NO:1, SEQ ID NO:2, SEQ ID NO:3, SEQ ID NO:4, or SEQ ID NO:6.

9. A transgenic plant cell comprising:
   a) a benzoate inducible promoter comprising a benzoate response element comprising a fragment of SEQ ID NO:1 comprising SEQ ID NO:4 operably linked to a promoter functional in a plant, and
   b) a nucleic acid sequence of interest, wherein said nucleic acid sequence of interest is operably linked to said benzoate inducible promoter.

10. The transgenic plant cell of claim 9, wherein said promoter comprises a plant minimal gene promoter.

11. The transgenic plant cell of claim 9, wherein said promoter is 35S.

12. The transgenic plant cell of claim 9, wherein the fragment of SEQ ID NO:1 comprising SEQ ID NO:4 is SEQ ID NO:1, SEQ ID NO:2, SEQ ID NO:3, SEQ ID NO:4, or SEQ ID NO:6.

13. A method of controlling expression of a nucleic acid sequence of interest in a plant, the method comprising:
   a) transforming said plant with an expression cassette comprising
      i) a benzoate inducible promoter comprising a benzoate response element comprising a fragment of SEQ ID NO: 1 comprising SEQ ID NO:4 operably linked to a promoter functional in a plant, and
      ii) a nucleic acid sequence of interest, wherein said nucleic acid sequence of interest is operably linked to said benzoate inducible promoter; and
   b) contacting said transformed plant with benzoate, whereby said benzoate inducible promoter in the presence of said benzoate induces the expression of said nucleic acid sequence of interest.

14. The method of claim 13, wherein said promoter comprises a plant minimal gene promoter.

15. The method of claim 13, wherein said promoter is 35S.

16. The method of claim 13, wherein the fragment of SEQ ID NO: 1 comprising SEQ ID NO:4 is SEQ ID NO:1, SEQ ID NO:2, SEQ ID NO:3, SEQ ID NO:4, or SEQ ID NO:6.

* * * * *

SEQUENCE LISTING

<160> NUMBER OF SEQ ID NOS: 38

<210> SEQ ID NO 1
<211> LENGTH: 1847

<212> TYPE: DNA
<213> ORGANISM: Aspergillus niger

<400> SEQUENCE: 1

```
cgtgtccgtt ctacaagatc atccctggat tctccctctg tgtggatgca tttcgatacg    60
gagccgtaga gggatgtaat gcgtacttcc ttagtcactt ccacagcgac cattacatcg   120
gcctgacggg gtcgtggcgc catggaccaa tctactgcag cagacctacg gccaacttgg   180
tgtgccagca actgaaggtc gaccggaagt ggcttgtacc acttgagttc gagcggaaga   240
cggaaatccc ggatacagga ggagcgcagg tgactttgat cgaggctaat cattgtcctg   300
ggagcgccat ctttctcttc gagaaatcaa tgggatcggg tccctcgcag agaacacatc   360
gtgtcctcca ctgtggtgac tttcgcgcct cgccgcttca tgtgcaacat gcccttctcc   420
gcccggagat tgctgacccc gcaaccggca aggctcgcca gcaacgaatc gatgcctgct   480
atctggacac tacatatttg agccccaagt atgcattccc tggccaggaa gatgtcatac   540
aagcctgcgc agaactttgc gttgagctcg atggggacgc caacgacaca aatggacgag   600
catttggacg accagtcaat ggaaaaagcg gaatgctgag caagtttgtt acggctgtga   660
ctggatcccg cccgtctccg acgcaagaca gccgccccc tggccggcta ttggtagtaa   720
tagggacgta cagcatcggc aaagaacgca tctgtctggg gatcgcacgg gcattgaaga   780
gcaagatcta cgcgacgcca gctaagcagc gcgtctgtgc gtgcctcgag gatgctgagc   840
tgtcatcgct gctgacagac gatcccacgg aggcgcaggt gcatatgcaa acgctattcg   900
agatccgggc ggaaacgctg gcggattacc tggactcgat gaagccgcac ttcacgcggg   960
tggtgggatt tcgaccaacc gggtggacgt atcgcccgcc agctggccga atgctggaca  1020
acccaccggt gtcggtggtg ctcaattcgg cacattggaa gacgcccttt tctgcgaaag  1080
acctggtgcc acagcgaggg agtacgcggg aaagcgcatg ctttggagtg ccgtacagtg  1140
agcacagctc atttcgggag ttgagcatgt tctgctgcgc actccggatc ggacgggtga  1200
tcccgacagt gaacgtaggt agccggaaaa gtcgggagcg catgaaggcg tggattgagc  1260
gatgggaggc ggagaagcgg aagaatgggt tgtaccgcgt ggaggggaat agctggtagg  1320
gaagggaata gatggctcta ccaatgtcca agtactggt ggaacagaag gatcagaagg  1380
attgcgaaag acgggtcgga acatgatgcc taatagagta agtaaggagt tggtgctgta  1440
actagtcaca agttacgagt tgtgtacata acatcattag tcatgaagat caattgcctt  1500
tatgcttccg taactctcgc ctccccggag tcacgagatc aatagaaacc accgccgttg  1560
accattcgcg atgctctcac tggctgtatg ctgtcgatag ccatggagcc attcaaagta  1620
tggacccttt gggtgaggat ctccctccaa ccccacggga cgtacacgaa caaccgagca  1680
gaggcggggg agggcaaaga ggccggcgct gcaaatcggc tggcagatca gtcgcggctc  1740
agcagagact cccgattttc ccttccgttg cctggctttg cctcgggggtt cgagaggagc  1800
ccgtctgcca taaataagcc tgcacttcaa ctcaaaaaaa agggaga                1847
```

<210> SEQ ID NO 2
<211> LENGTH: 403
<212> TYPE: DNA
<213> ORGANISM: Aspergillus niger

<400> SEQUENCE: 2

```
aatagatggc tctaccaatg tccaaagtac tggtggaaca gaaggatcag aaggattgcg    60
aaagacgggt cggaacatga tgcctaatag agtaagtaag gagttggtgc tgtaactagt   120
```

```
cacaagttac gagttgtgta cataacatca ttagtcatga agatcaattg cctttatgct    180
tccgtaactc tcgcctcccc ggagtcacga gatcaataga aaccaccgcc gttgaccatt    240
cgcgatgctc tcactggctg tatgctgtcg atagccatgg agccattcaa agtatggacc    300
ctttgggtga ggatctccct ccaaccccac gggacgtaca cgaacaaccg agcagaggcg    360
ggggagggca agaggccggc gctgcaaat cggctggcag atc                       403
```

<210> SEQ ID NO 3
<211> LENGTH: 201
<212> TYPE: DNA
<213> ORGANISM: Aspergillus niger

<400> SEQUENCE: 3

```
tagggaaggg aatagatggc tctaccaatg tccaaagtac tggtggaaca gaaggatcag     60
aaggattgcg aaagacgggt cggaacatga tgcctaatag agtaagtaag gagttggtgc    120
tgtaactagt cacaagttac gagttgtgta cataacatca ttagtcatga agatcaattg    180
cctttatgct tccgtaactc t                                              201
```

<210> SEQ ID NO 4
<211> LENGTH: 51
<212> TYPE: DNA
<213> ORGANISM: Aspergillus niger

<400> SEQUENCE: 4

```
actagtcaca agttacgagt tgtgtacata acatcattag tcatgaagat c              51
```

<210> SEQ ID NO 5
<211> LENGTH: 6
<212> TYPE: DNA
<213> ORGANISM: Aspergillus niger

<400> SEQUENCE: 5

```
tagtca                                                                 6
```

<210> SEQ ID NO 6
<211> LENGTH: 531
<212> TYPE: DNA
<213> ORGANISM: Aspergillus niger

<400> SEQUENCE: 6

```
tagggaaggg aatagatggc tctaccaatg tccaaagtac tggtggaaca gaaggatcag     60
aaggattgcg aaagacgggt cggaacatga tgcctaatag agtaagtaag gagttggtgc    120
tgtaactagt cacaagttac gagttgtgta cataacatca ttagtcatga agatcaattg    180
cctttatgct tccgtaactc tcgcctcccc ggagtcacga gatcaataga aaccaccgcc    240
gttgaccatt cgcgatgctc tcactggctg tatgctgtcg atagccatgg agccattcaa    300
agtatggacc ctttgggtga ggatctccct ccaaccccac gggacgtaca cgaacaaccg    360
agcagaggcg ggggagggca agaggccggc gctgcaaat cggctggcag atcagtcgcg    420
gctcagcaga gactcccgat tttcccttcc gttgcctggc tttgcctcgg ggttcgagag    480
gagcccgtct gccataaata agcctgcact tcaactcaaa aaaagggag a               531
```

<210> SEQ ID NO 7
<211> LENGTH: 14
<212> TYPE: DNA
<213> ORGANISM: Aspergillus niger

<400> SEQUENCE: 7

-continued

```
gttgtgtaca taac                                                    14

<210> SEQ ID NO 8
<211> LENGTH: 9
<212> TYPE: DNA
<213> ORGANISM: Aspergillus niger

<400> SEQUENCE: 8 cattagtca                                                           9

<210> SEQ ID NO 9
<211> LENGTH: 51
<212> TYPE: DNA
<213> ORGANISM: Aspergillus niger

<400> SEQUENCE: 9
acaaatcaca agttacgagt tgtgtacata acatcattag tcatgaagat c            51

<210> SEQ ID NO 10
<211> LENGTH: 51
<212> TYPE: DNA
<213> ORGANISM: Aspergillus niger

<400> SEQUENCE: 10
actagaaaca agttacgagt tgtgtacata acatcattag tcatgaagat c            51

<210> SEQ ID NO 11
<211> LENGTH: 51
<212> TYPE: DNA
<213> ORGANISM: Aspergillus niger

<400> SEQUENCE: 11
actagtcaca agttacgagt tgtgtacata acatcataaa tcatgaagat c            51

<210> SEQ ID NO 12
<211> LENGTH: 51
<212> TYPE: DNA
<213> ORGANISM: Aspergillus niger

<400> SEQUENCE: 12
actagtcaca agttacgagt tgtgtacata acatcattag aaatgaagat c            51

<210> SEQ ID NO 13
<211> LENGTH: 51
<212> TYPE: DNA
<213> ORGANISM: Aspergillus niger

<400> SEQUENCE: 13
actagtcaca agttacgagt tgtgtacata acatcattag tcataaagat c            51

<210> SEQ ID NO 14
<211> LENGTH: 51
<212> TYPE: DNA
<213> ORGANISM: Aspergillus niger

<400> SEQUENCE: 14
actagtcaca agttacgagt tgtgtacata acatcatatt aattgaagat c            51

<210> SEQ ID NO 15
<211> LENGTH: 274
<212> TYPE: PRT
<213> ORGANISM: Aspergillus niger
```

<400> SEQUENCE: 15

```
Met Val Ser Phe Lys Ser Leu Leu Thr Ala Thr Thr Leu Ala Thr Ala
1               5                   10                  15

Val Leu Ala Ile Pro His Ser Gly His Gly His Gly Ser His Lys His
            20                  25                  30

Arg Ser Thr His Val Ala Ser Lys Arg Thr Ser Ser Lys Arg Gly
        35                  40                  45

Ala Ala Tyr Asn Ser Ala Ser Ser Val His Thr Leu Thr Ser Gly Ser
    50                  55                  60

Ser Gly Asn Gly Thr Val Ser Trp Ala Tyr Asp Trp Asn Met Tyr Ala
65                  70                  75                  80

Asp Gly Thr Leu Pro Ser Asn Val Glu Tyr Val Pro Met Leu Trp Gly
                85                  90                  95

Ser Lys Met Phe Gly Gly Trp Leu Thr Ala Ile Glu Thr Ala Leu Asp
            100                 105                 110

Ser Gly Ser Asn Tyr Ile Met Gly Phe Asn Glu Pro Asp Ser Ser Ser
        115                 120                 125

Gln Ala Ser Met Thr Ala Ser Glu Ala Ala Ser Ser Tyr Lys Asn Tyr
    130                 135                 140

Ile Thr Pro Tyr Ser Gly Lys Ala Lys Leu Val Thr Pro Ala Val Thr
145                 150                 155                 160

Ser Ser Thr Thr Glu Gly Glu Gly Leu Ser Trp Met Lys Ser Phe Leu
                165                 170                 175

Ser Glu Cys Ser Glu Cys Asp Met Ser Val Leu Ala Val His Trp Tyr
            180                 185                 190

Gly Thr Ser Ala Asp Glu Phe Lys Ser Phe Val Gln Glu Ala Met Gln
        195                 200                 205

Val Ala Asp Asp Asn Gly Leu Asp Glu Thr Trp Val Thr Glu Phe Ala
    210                 215                 220

Leu Thr Ser Asp Glu Ser Ala Gly Gly Asp Glu Ser Ser Ala Ala Asp
225                 230                 235                 240

Phe Leu Asp Glu Gly Val Gly Arg Tyr Ala Tyr Tyr Met Cys Ala Asp
                245                 250                 255

Gly Tyr Leu Leu Ser Gly Glu Glu Leu Ser Ser Ser Gly Lys Val Tyr
            260                 265                 270

Val Ala
```

<210> SEQ ID NO 16
<211> LENGTH: 825
<212> TYPE: DNA
<213> ORGANISM: Aspergillus niger

<400> SEQUENCE: 16

```
atggtctcct tcaagtctct tctgaccgcc accaccctgg ccaccgccgt tctggccatc      60
cctcatagtg gccacggcca tggcagccac aagcaccgtt ccaccatgt cgcctccaag     120
cggacctctt cctccaagcg tggcgctgcc tacaactctg cttccagcgt tcacacgctg     180
acctccggct cctccggcaa cggtaccgtc tcctgggcct acgactggaa catgtacgcc     240
gacggcaccc tccccagtaa cgtcgaatac gtgcccatgc tgtggggcag caagatgttt     300
ggaggctggt tgaccgccat cgagactgcc ctggacagcg gtagcaatta catcatggga     360
ttcaacgagc ctgactcctc ctcccaagcc tcgatgactg cttccgaggc cgccagctcc     420
tacaagaatt acatcactcc ttactctggc aaggctaagc tcgtcacccc ggccgtgacc     480
```

```
agtagcacca cggaaggcga gggtctcagc tggatgaagt ccttcctgtc cgaatgcagc      540
gagtgtgaca tgtcggtgct ggcagtccac tggtacggca cctcggccga tgagttcaag      600
tccttcgtgc aggaggccat gcaggtggcg gacgacaacg gattggacga acctgggtg       660 acagaattcg ccctcaccag cgacgagtct gccggcggcg atgagagttc agcggcggac      720
ttccttgacg aaggcgtggg acggtatgcg tattacatgt gtgcagatgg gtatctgctc      780
agcggggagg agttgagctc gagtggaaag gtctacgttg catag                       825
```

<210> SEQ ID NO 17
<211> LENGTH: 129
<212> TYPE: PRT
<213> ORGANISM: Aspergillus niger

<400> SEQUENCE: 17

```
Asp Ser Ala Glu Ser Arg Phe Ser Leu His Ser Gln Gly Ser Val Pro
1               5                   10                  15
Pro Ala Pro Ser Thr Ala Thr Lys His Met Thr Pro His Asn His Thr
            20                  25                  30
Asn Asn His Gly Gly Pro Leu Pro Ser Lys Pro Gly Ser Glu Gly Ala
        35                  40                  45
Ser Asn Asn Gly Thr Gln Ile Thr Gly Pro His Glu Ser Asn Leu Ile
    50                  55                  60
Glu Gln Phe Arg Glu Arg Glu Asp Lys Leu Trp Ala Tyr Val Arg Ser
65                  70                  75                  80
Val His Glu Glu Leu Asn Gly Leu Arg Thr Glu Val Ala Ala Leu Arg
                85                  90                  95
Ala Gln Leu Ala Ser Ala Asn Val Asn Ala Leu Ala Met Ser Ser Gln
            100                 105                 110
Ser Ala Pro Gln Ser Gln Pro Glu Thr Asn Ala Ala Gly Thr Ser Gln
        115                 120                 125
Arg
```

<210> SEQ ID NO 18
<211> LENGTH: 390
<212> TYPE: DNA
<213> ORGANISM: Aspergillus niger

<400> SEQUENCE: 18

```
gactcggctg aatctcggtt tagccttcac tctcaaggat cagtgccacc ggcgccttcg       60
acggctacca aacacatgac ccctcacaat cacacaaata accacggtgg tccactaccg      120
tcgaaacctg gatcggaagg ggcctcgaat aatggcaccc agatcactgg tcctcatgag      180
tccaatctca tcgagcagtt ccgtgagcgg gaagacaagc tgtgggctta tgtccgctcg      240
gtgcacgaag aattaaatgg acttcggacg gaagttgccg ctctaagggc ccaacttgca      300
tcagctaacg tcaacgcgct agcaatgtca agccaaagtg cacctcagtc tcaacccgag      360
acaaacgctg ctggtacatc ccaacggtga                                       390
```

<210> SEQ ID NO 19
<211> LENGTH: 27
<212> TYPE: DNA
<213> ORGANISM: Artificial
<220> FEATURE:
<223> OTHER INFORMATION: Synthetic

<400> SEQUENCE: 19

```
gcattgaagc tttacatcgg cctgacg                                           27
```

<210> SEQ ID NO 20
<211> LENGTH: 30
<212> TYPE: DNA
<213> ORGANISM: Artificial
<220> FEATURE:
<223> OTHER INFORMATION: Synthetic

<400> SEQUENCE: 20
aagcccaagc ttgagtaagt aaggagttgg                                    30

<210> SEQ ID NO 21
<211> LENGTH: 28
<212> TYPE: DNA
<213> ORGANISM: Artificial
<220> FEATURE:
<223> OTHER INFORMATION: Synthetic

<400> SEQUENCE: 21
ttttccaagc ttccgtaact ctcgcctc                                      28

<210> SEQ ID NO 22
<211> LENGTH: 30
<212> TYPE: DNA
<213> ORGANISM: Artificial
<220> FEATURE:
<223> OTHER INFORMATION: Synthetic

<400> SEQUENCE: 22
cccgttaagc tttttgagtt gaagtgcagg                                    30

<210> SEQ ID NO 23
<211> LENGTH: 27
<212> TYPE: DNA
<213> ORGANISM: Artificial
<220> FEATURE:
<223> OTHER INFORMATION: Synthetic

<400> SEQUENCE: 23
gcaggaattc gatctgcttc ctcaacc                                       27

<210> SEQ ID NO 24
<211> LENGTH: 28
<212> TYPE: DNA
<213> ORGANISM: Artificial
<220> FEATURE:
<223> OTHER INFORMATION: Synthetic

<400> SEQUENCE: 24
ccggaattcg ataagcttga tggggatc                                      28

<210> SEQ ID NO 25
<211> LENGTH: 39
<212> TYPE: DNA
<213> ORGANISM: Artificial
<220> FEATURE:
<223> OTHER INFORMATION: Synthetic

<400> SEQUENCE: 25
aagcagtggt atcaacgcag agtggccatt atggccggg                          39

<210> SEQ ID NO 26
<211> LENGTH: 31
<212> TYPE: DNA
<213> ORGANISM: Artificial
<220> FEATURE:

<223> OTHER INFORMATION: Synthetic

<400> SEQUENCE: 26
tatggatccc tgcagactag tcacaagtta c                                31

<210> SEQ ID NO 27
<211> LENGTH: 35
<212> TYPE: DNA
<213> ORGANISM: Artificial
<220> FEATURE:
<223> OTHER INFORMATION: Synthetic

<400> SEQUENCE: 27
tatggatcca tgcatgatct tcatgactaa tgatg                            35

<210> SEQ ID NO 28
<211> LENGTH: 26
<212> TYPE: DNA
<213> ORGANISM: Artificial
<220> FEATURE:
<223> OTHER INFORMATION: Synthetic

<400> SEQUENCE: 28
ctattcgatg atgaagatac cccacc                                      26

<210> SEQ ID NO 29
<211> LENGTH: 22
<212> TYPE: DNA
<213> ORGANISM: Artificial
<220> FEATURE:
<223> OTHER INFORMATION: Synthetic

<400> SEQUENCE: 29
gtgaacttgc ggggttttc ag                                           22

<210> SEQ ID NO 30
<211> LENGTH: 25
<212> TYPE: DNA
<213> ORGANISM: Artificial
<220> FEATURE:
<223> OTHER INFORMATION: Synthetic

<400> SEQUENCE: 30
cacatacaca atggtctcct tcaag                                       25

<210> SEQ ID NO 31
<211> LENGTH: 24
<212> TYPE: DNA
<213> ORGANISM: Artificial
<220> FEATURE:
<223> OTHER INFORMATION: Synthetic

<400> SEQUENCE: 31
ctgcacacat gtaatacgca tacc                                        24

<210> SEQ ID NO 32
<211> LENGTH: 25
<212> TYPE: DNA
<213> ORGANISM: Artificial
<220> FEATURE:
<223> OTHER INFORMATION: Synthetic

<400> SEQUENCE: 32
ggtttagcct tcactctcaa ggatc                                       25

<210> SEQ ID NO 33
<211> LENGTH: 25
<212> TYPE: DNA
<213> ORGANISM: Artificial
<220> FEATURE:
<223> OTHER INFORMATION: Synthetic

<400> SEQUENCE: 33
gtcgaaaggt gcgattcgat atagg    25

<210> SEQ ID NO 34
<211> LENGTH: 279
<212> TYPE: PRT
<213> ORGANISM: Aspergillus nidulans

<400> SEQUENCE: 34

```
Met Val Ser Phe Lys Ser Leu Ala Ala Leu Ala Leu Leu Ala Ser Ser
1               5                   10                  15

Ala Leu Ala Ala Pro His Gly His Ala His Thr Thr Leu His Lys Leu
            20                  25                  30

Glu Pro Val Lys Arg Ala Ser Asn Thr Thr Thr Ser Ser Lys Arg Gly
        35                  40                  45

Ala Ala Tyr Asn Asp Ala Ser Leu Val Glu Ala Leu Ala Ser Ser Gly
    50                  55                  60

Thr Ile Ser Trp Ala Tyr Asp Trp Asn Met Tyr Thr Met Gly Asp Leu
65                  70                  75                  80

Pro Ser Asn Val Glu Phe Val Pro Met Leu Trp Gly Thr Lys Met Phe
                85                  90                  95

Thr Gly Trp Phe Ala Ala Ile Gln Thr Leu Leu Asn Ser Gly Asn Asn
            100                 105                 110

Tyr Ile Leu Gly Phe Asn Glu Pro Asp Met Ala Ser Gln Ala Ala Met
        115                 120                 125

Ser Ser Ser Asp Ala Ala Lys Tyr Tyr Lys Asn Tyr Ile Ser Thr Phe
    130                 135                 140

Ala Gly Lys Ser Lys Leu Val Ser Pro Ala Val Thr Asn Gly Glu Gly
145                 150                 155                 160

Asp Asp Val Gly Leu Asn Trp Met Arg Asn Phe Leu Asn Ser Cys Thr
                165                 170                 175

Asp Cys Asp Val Asp Ala Leu Ala Val His Trp Tyr Gly Asp Ser Ala
            180                 185                 190

Asp Asp Phe Lys Ala Phe Val Glu Lys Ala Thr Ala Leu Ala Asp Glu
        195                 200                 205

Phe Gly Leu Ser Glu Thr Trp Val Thr Glu Phe Ala Leu Asn Ser Asp
    210                 215                 220

Leu Ser Gly Ser Ala Asp Ala Ser Thr Ser Ala Asp Phe Leu Ser Glu
225                 230                 235                 240

Val Leu Pro Trp Leu Asp Glu His Asp Lys Val Ser Arg Tyr Ala Tyr
                245                 250                 255

Phe Met Cys Ser Asp Gly His Leu Leu Ser Gly Asn Ser Leu Ser Val
            260                 265                 270

Ser Gly Lys Ala Tyr Val Ser
        275
```

<210> SEQ ID NO 35
<211> LENGTH: 840
<212> TYPE: DNA
<213> ORGANISM: Aspergillus nidulans

<400> SEQUENCE: 35

```
atggtctcct tcaagtcgct tgccgctctg gcccttcttg ccagctctgc gctcgccgct      60
ccccatggcc atgctcacac taccttgcac aagctcgagc ccgtcaagcg cgcgtccaac     120
acgacgacct cctccaagcg cggcgccgct tacaacgatg cctccctcgt cgaggccctc     180
gcttcctccg caccatctc ctgggcctac gattggaaca tgtacaccat gggcgatctc     240
cccagcaatg tcgagttcgt gccgatgctc tggggtacaa agatgttcac cggctggttc     300
gccgcgatcc agacgctctt gaactctgga acaactaca tccttggttt caacgagccg     360
gacatggcgt ctcaggccgc gatgtcctcg tccgatgctg ccaaatacta taagaactat     420
atcagcacct tcgccggcaa gtcaaagctc gtctcgcccg cggtcaccaa cggcgaggga     480
gacgacgtcg tctcaactg gatgcgcaac ttcctgaact cctgtacaga ctgcgacgtc     540
gatgctcttg ctgtccactg gtacggtgac tcggcagacg acttcaaggc cttcgttgaa     600
aaggccaccg cgctggctga cgagttcggt ctcagcgaaa cctgggttac ggagtttgcg     660
ctcaactcgg atttgtccgg ctccgcggat gccagcactt cggcggactt cttgagcgag     720
gtgctgcctt ggttggatga acatgacaag gtcagccgct atgcgtactt catgtgctcg     780
gatggccatc tgctcagtgg aaacagcttg agcgtgagtg gaaaggcgta tgtttcttga     840
```

<210> SEQ ID NO 36
<211> LENGTH: 667
<212> TYPE: PRT
<213> ORGANISM: Aspergillus nidulans

<400> SEQUENCE: 36

```
Met Thr Ser Ile Tyr Leu Ala Leu Gly His His Pro Ser Phe Arg
 1               5                  10                  15

Gly Ser Val Lys Asp Pro Val Pro Met Ala Ala Leu Met Gln Ser Asn
                20                  25                  30

Asn Glu Pro Val Ala Ile Ser Thr Pro Leu Thr Ala Ser Ser Asp Pro
            35                  40                  45

Ile Ala Ser Ser Pro Gly Ser Ala Thr Phe Leu Lys Gln Ser Lys
         50                  55                  60

Pro Asp Ser Asn Leu Thr Ser Ile Ala Asn Ala Gly Leu Asn Val Thr
 65                  70                  75                  80

Arg Ser Lys Asp Ser Leu Pro Ala Met Ser Thr Thr Ala Val Pro Asn
                 85                  90                  95

Ser Gly Ser Ala Glu Arg Gln Leu Glu Ser His Arg Asp Ala Asp Gln
            100                 105                 110

Asp Ser Ser Gln Val Ala Arg Glu Ala Leu Gly Ala Ser Glu Lys His
        115                 120                 125

Gln Ser Ser Val Gly Asp Ser Leu Ala Ile His Ser Asp Gln Met
    130                 135                 140

Gln Val Asp Ser His Pro Gly Pro Glu Ala Gly Asp Pro Val Phe
145                 150                 155                 160

Asn Thr Ala Glu Asn Gly Thr Ser Leu Ile Asn Ser Ser Thr Val Ala
                165                 170                 175

Ser Pro Gly Pro Ile Glu Asp Ser Val Ser Gln Asp Gly Asp Gln Pro
            180                 185                 190

Arg His Arg Asp Asp Gly Asp Leu His Gln Glu Asn Asn Asn Lys Ala
        195                 200                 205

Phe Ser Tyr Pro Met Pro Thr Gly Ala Phe Asn Asp Pro Arg Arg Gly
    210                 215                 220
```

```
Leu Ser Leu Pro Ser Ser Gly Leu His Lys Ala Gly Gln Arg Ser Pro
225                 230                 235                 240

Ser Ala Lys Lys His Arg Cys Pro Tyr Cys Ala Thr Glu Phe Thr Arg
            245                 250                 255

His His Asn Leu Lys Ser His Leu Leu Thr His Ser Gln Glu Lys Pro
        260                 265                 270

Phe Val Cys Thr Thr Cys Gln Ser Arg Phe Arg Arg Leu His Asp Leu
            275                 280                 285

Lys Arg His Gln Lys Leu His Thr Gly Glu Arg Pro His Ile Cys Pro
290                 295                 300

Lys Cys Gly Arg Arg Phe Ala Arg Gly Asp Ala Leu Ala Arg His Asn
305                 310                 315                 320

Lys Gly Gln Gly Gly Cys Ala Gly Arg Arg Ala Ser Met Gly Ser Tyr
            325                 330                 335

Ala Pro Glu Asp Glu Tyr Gly Asp Ala Ala Ala Gly Ala Asp Glu
            340                 345                 350

Ala Met Asp Gly Leu Val Tyr Ala Glu Pro Glu Arg Met Asp Glu Asp
            355                 360                 365

Asp Glu Arg Arg Tyr Asn Met Pro Ser Ile Lys Lys His Asp Val Pro
370                 375                 380

Ser Asp Ser Ala Val Arg Ser Asn Ser Val Ser Ser Tyr Gln Ala Arg
385                 390                 395                 400

Gln Pro Ser Thr Tyr Pro Pro Ile Ala Ala Ser Arg Pro Ser Pro Gly
            405                 410                 415

Gly Leu Phe Pro Pro Thr Ser His Gly Gly Ser Ser Ala Ser Pro
            420                 425                 430

Ser Pro Ile Ser Gln Ser Gly Asn Met Ala Phe Pro Ser Thr Asn Gln
        435                 440                 445

Pro Ser Gly Ser Ser Ala Phe Ala Pro Ser Asn Met Ala Glu Ser Pro
450                 455                 460

Arg Pro Leu Ser Pro Asn Ala Leu Ser Ser His Gln Leu Gly His Gly
465                 470                 475                 480

Pro Glu Asn Gly Leu Gln Met His His Arg Ala His Ser Ala Gly Ile
            485                 490                 495

Ser His Pro Phe Pro Gln Gln Ser Tyr Asn Arg Thr Gly Pro Ser Gln
            500                 505                 510

Ala Ser Leu Ser Asn His Thr Ala Pro Ser Leu Gly Leu Pro Pro Pro
            515                 520                 525

Gln Pro Gly Ala Pro Gln Leu Pro Pro Pro Gly Leu Gly Ser Ser
530                 535                 540

Glu Pro Arg Phe Ser Leu His Ser Gln Ser Ser Val Gln Ala Ser Gly
545                 550                 555                 560

Ser Ala Ala Lys His Thr Pro Ser His Ser His Ser Ser Asn His Gly
            565                 570                 575

Gly Ser Leu Thr Ser Lys Thr Ile Pro Glu Ala Ala Ser Thr His Asn
            580                 585                 590

Val His Thr Ser His Asp Pro Ser Val Phe Asp Gln Gln Arg Glu Arg
            595                 600                 605

Glu Glu Lys Leu Trp Glu Tyr Ile Arg Ser Val His Glu Glu Leu Asn
            610                 615                 620

Gly Leu Lys Ser Glu Val Ala Thr Leu Arg Ala Gln Val Ala Ser Ser
625                 630                 635                 640
```

Ser Val Asn Ala Ser Thr Thr Ser Gly Ser Ser Val Thr Gln Ser Ser
                645                 650                 655

Val Glu Thr Gly Thr Thr Asn Thr Val Gln Arg
            660                 665

<210> SEQ ID NO 37
<211> LENGTH: 2004
<212> TYPE: DNA
<213> ORGANISM: Aspergillus nidulans

<400> SEQUENCE: 37

| | |
|---|---|
| atgacttcga tctatctagc tcttggccac catcatccat cgtttcgagg tagcgtgaaa | 60 |
| gacccggtac ccatggccgc gttgatgcag tcaaacaacg agcccgtcgc catctcaacc | 120 |
| cctttgaccg cctcatcgga cccgattgcc tcgagttccc cgggatctgc tacctttta | 180 |
| aaacagtcta aacctgactc gaacctcacc tccattgcca acgcggggtt aaacgtgacg | 240 |
| cgatcaaaag actccttacc ggcgatgtca acaacagcag tgccaaactc tggctccgcg | 300 |
| gagcggcagc tcgaatctca tagagatgcg gaccaggata gctctcaggt tgcgcgcgaa | 360 |
| gcgctcggcg ctagtgagaa acatcagtct agctctgtcg gcgactcact agccatacac | 420 |
| tccgaccaaa tgcaggtcga ctctcatcct ggtcccggtg aagcgggcga tccggttttc | 480 |
| aacactgctg agaacggaac ttctttaata aacagctcga ctgtagcaag ccccggaccc | 540 |
| atagaagatt ctgtctctca ggacggtgac caaccgcgtc atcgagacga cggcgacttg | 600 |
| catcaagaaa ataataacaa agcttttctca taccccatgc ctacaggggc gttcaacgac | 660 |
| ccccggcgtg gtctcagctt accaagctcc ggcctccaca aggctggtca acggtctcca | 720 |
| tccgctaaga agcatagatg cccctattgc gcaacggagt tcacacgaca tcacaacctc | 780 |
| aaaagccacc tcctcacaca tagtcaagag aagccgtttg tatgcacgac ctgtcagtca | 840 |
| cgcttccggc gacttcatga cctcaaaaga caccaaaagc ttcatactgg tgagcgaccc | 900 |
| catatatgtc cgaagtgcgg acgcaggttt gctcgcggtg atgcccttgc gcgtcataat | 960 |
| aagggccaag gtggctgtgc tggtcgtagg gccagcatgg gaagttacgc acccgaagat | 1020 |
| gagtatggtg atgccgcagc tgctggtgcc gacgaggcta tggatgggct agtttacgcc | 1080 |
| gagccggaac gcatggatga agatgatgaa cgacgttaca acatgccgag cataaagaag | 1140 |
| catgatgtgc cctcggattc tgccgttcgc tcaaacagcg taagcagcta tcaagcgcgt | 1200 |
| caacctagca cttaccctcc aattgccgcg agcagaccgt cgcctggcgg gcttttccct | 1260 |
| cctcctacaa gtcatggcgg ttctagtgcc tccccttctc ccatatctca gtccggcaat | 1320 |
| atggcgttcc cctcgacaaa ccagccatct ggctcctctg cttttgcgcc ttcaaacatg | 1380 |
| gctgaaagtc aagaccgct ctcaccgaac gcactatctt cccaccaatt aggacacggg | 1440 |
| ccggaaaacg gtctacaaat gcaccatcgc gcccactctg ctggaatctc acatccattc | 1500 |
| cctcaacaat catacaatcg tacaggcccc tctcaggctt ctctttccaa ccacactgca | 1560 |
| ccgagcttag gccttccacc acctcagccc ggggcccctc aacttccgcc gccacctggc | 1620 |
| ttggggtctt ctgagcctcg tttttccctc cactcgcaaa gctccgtaca ggcttccggt | 1680 |
| tccgccgcta aacatacgcc atcacatagc cactcgagta atcacggtgg ttctttgact | 1740 |
| tccaagacaa tccccgaagc agcatcaacg cataacgtcc atacctctca cgatccgagc | 1800 |
| gtcttcgatc agcaacggga acgggaggaa aagctctggg agtacattcg ctcagttcat | 1860 |
| gaggaactaa atggactcaa gtcggaggta gccacccctca gggcacaagt ggcatcgtcg | 1920 |
| agtgtgaacg catcgactac gtctggttct agtgttacac aatcatcagt tgagacgggc | 1980 |

```
accacaaata cggtgcaacg gtga                                           2004

<210> SEQ ID NO 38
<211> LENGTH: 57
<212> TYPE: DNA
<213> ORGANISM: Artificial
<220> FEATURE:
<223> OTHER INFORMATION: Synthetic

<400> SEQUENCE: 38
attctagagg ccgaggcggc cgacatgttt tttttttttt tttttttttt tttttt          57
```